(12) United States Patent
Huang et al.

(10) Patent No.: US 12,099,042 B2
(45) Date of Patent: Sep. 24, 2024

(54) USE OF LIQUID CHROMATOGRAPHY AND MASS SPECTROMETRY TO CHARACTERIZE OLIGONUCLEOTIDES

(71) Applicant: Regeneron Pharmaceuticals, Inc., Tarrytown, NY (US)

(72) Inventors: Ming Huang, Township of Washington, NJ (US); Haibo Qiu, Hartsdale, NY (US); Xiaobin Xu, Old Greenwich, CT (US); Ning Li, New Canaan, CT (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 883 days.

(21) Appl. No.: 17/161,803

(22) Filed: Jan. 29, 2021

(65) Prior Publication Data
US 2021/0239663 A1 Aug. 5, 2021

Related U.S. Application Data

(60) Provisional application No. 62/968,368, filed on Jan. 31, 2020.

(51) Int. Cl.
*G01N 30/88* (2006.01)
*H01J 49/00* (2006.01)

(52) U.S. Cl.
CPC ............ *G01N 30/88* (2013.01); *H01J 49/004* (2013.01); *G01N 2030/8813* (2013.01)

(58) Field of Classification Search
None
See application file for complete search history.

(56) References Cited

U.S. PATENT DOCUMENTS

| | | |
|---|---|---|
| 5,378,825 A | 1/1995 | Cook et al. |
| 5,585,481 A | 12/1996 | Arnold, Jr. et al. |
| 6,107,623 A | 8/2000 | Bateman et al. |
| 6,124,137 A | 9/2000 | Hutchens et al. |
| 6,204,500 B1 | 3/2001 | Whitehouse et al. |
| 6,268,144 B1 | 7/2001 | Köster |
| 6,949,367 B1 | 9/2005 | Dempcy et al. |
| 7,507,532 B2 | 3/2009 | Chang et al. |
| 8,148,677 B2 | 4/2012 | Zhang et al. |
| 8,278,620 B2 | 10/2012 | Schwartz et al. |
| 8,921,116 B2 | 12/2014 | Shriver et al. |
| 9,512,467 B2 | 12/2016 | Nelson et al. |
| 10,319,573 B2 | 6/2019 | Bern |
| 2005/0120415 A1 | 6/2005 | Aukerman |
| 2005/0144669 A1 | 6/2005 | Reinhart et al. |
| 2007/0123482 A1 | 5/2007 | Stoffel et al. |
| 2007/0213292 A1 | 9/2007 | Stoffel et al. |
| 2019/0055562 A1 | 2/2019 | Pecot et al. |
| 2019/0256854 A1 | 8/2019 | Chatterton et al. |
| 2022/0267862 A1 | 8/2022 | Szyf et al. |

FOREIGN PATENT DOCUMENTS

| | | |
|---|---|---|
| AU | 2012318752 B2 | 8/2017 |
| CA | 2266748 C | 2/2010 |
| WO | WO 93/13121 A1 | 7/1993 |
| WO | WO 95/32305 A1 | 11/1995 |
| WO | WO 2015/175561 A1 | 11/2015 |
| WO | WO 2016/196181 A1 | 12/2016 |
| WO | WO 2020/252292 A1 | 12/2020 |

OTHER PUBLICATIONS

Basiri, et al. (2016) "The Role of Fluorinated Alcohols as Mobile Phase Modifiers for LC-MS Analysis of Oligonucleotides", Journal of the American Society for Mass Spectrometry, 28: 190-99. (Year: 2016).*

Brown, et al. (2018) "Total RNA extraction from tissues for microRNA and target gene expression analysis: not all kits are created equal", BMC Biotechnology, 18:16, 11 pages long. (Year: 2018).*

Ewles, et al. (2014) "Quantification of oligonucleotides by LC-MS/MS: the challenges of quantifying a phosphorothioate oligonucleotide and multiple metabolites", Bioanalysis, 6(4): 447-64 (Abstract Only). (Year: 2014).*

Polo and Limbach (2000) "Analysis of Oligonucleotides by Electrospray Ionization Mass Spectrometry", Current Protocols in Nucleic Acid Chemistry, By John Wiley & Sons, Inc., Unit 10.2, 20 pages. (Year: 2000).*

Birdsall et al., "Reduction of metal adducts in oligonucleotide mass spectra in ion-pair reversed-phase chromatography/mass spectrometry analysis," Rapid Commun. Mass Spectrom., 2016, 30, 1667-1679.

Chen and Bartlett, "A One-Step Solid Phase Extraction Method for Bioanalysis of a Phosphorothioate Oligonucleotide and Its 3' n-1 Metabolite from Rat Plasma by uHPLC-MS/MS," The AAPS Journal, Dec. 2012, vol. 14, No. 4, pp. 772-780.

Easter et al., "Separation and identification of oligonucleotides by hydrophilic interaction liquid chromatography (HILIC)—inductively coupled plasma mass spectrometry (ICPMS)," Analyst, Oct. 2010; 135(10): 2560-2565, 20 pages provided.

Gong and McCullagh, "Analysis of oligonucleotides by hydrophilic interaction liquid chromatography coupled to negative ion electrospray ionization mass spectrometry," Journal of Chromatography A, (2011) 1218: 5480-5486.

Gong and McCullagh, "Comparing ion-pairing reagents and sample dissolution solvents for ion-pairing reversed-phase liquid chromatography/electrospray ionization mass spectrometry analysis of oligonucleotides," Rapid Commun. Mass Spectrom., 2014, 28, 339-350.

Goyon et al., "Characterization of therapeutic oligonucleotides by liquid chromatography," Journal of Pharmaceutical and Biomedical Analysis, (2020) 182: 113105, 17 pages provided.

(Continued)

*Primary Examiner* — Robert M Kelly
(74) *Attorney, Agent, or Firm* — COOLEY LLP

(57) ABSTRACT

The disclosure provides methods of characterizing a sample of oligonucleotides of interest using liquid chromatography and mass spectrometry.

28 Claims, 26 Drawing Sheets
Specification includes a Sequence Listing.

(56) References Cited

OTHER PUBLICATIONS

Lobue et al., "Oligonucleotide analysis by hydrophilic interaction liquid chromatography-mass spectrometry in the absence of ion-pair reagents," Journal of Chromatography A, (2019) 1595: 39-48.
McCarthy et al., "Reversed-phase ion-pair liquid chromatography analysis and purification of small interfering RNA," Analytical Biochemistry (2009) 390: 181-188.
Sharma et al., "Reversed-phase ion-pair liquid chromatography electrospray ionization tandem mass spectrometry for separation, sequencing and mapping of sites of base modification of isomeric oligonucleotide adducts using monolithic column," Journal of Chromatography A, (2012) 1245: 65-74.
Studzińska, S., "Review on investigations of antisense oligonucleotides with the use of mass spectrometry," Talanta (2017) 176: 329-343.
Tretyakova et al., "Mass Spectrometry of Structurally Modified DNA," Chem. Rev. 2013, 113: 2395-2436.
Altschul et al., "Basic Local Alignment Search Tool," J. Mol. Biol. (1990) 215, 403-410.
Atdbio, Solid-Phase Oligonucleotide Synthesis, 2005-2021, 18 pages, retrieved from https://www.atdbio.com/content/17/Solid-phase-oligonucleotide-synthesis.
Carrillo and Lipman, "The Multiple Sequence Alignment Problem in Biology," SIAM Journal on Applied Math 48:1073-1082 (1988).
Integrated DNA Technologies, Locked nucleic acids-Affinity Plus modified bases, 2021, 6 pages, retrieved from https://www.idtdna.com/site/Catalog/Modifications/Category/7.
McLuckey et al., "Tandem Mass Spectrometry of Small, Multiply Charged Oligonucleotides," J Am Soc Mas. Spectrom, 1992, 3: 60-70.
Rossor et al., "Antisense oligonucleotides and other genetic therapies made simple," Pract Neurol. Apr. 2018;18(2):126-131.
Shen and Corey, "Chemistry, mechanism and clinical status of antisense oligonucleotides and duplex RNAs," Nucleic Acids Research, 2018, vol. 46, No. 4, pp. 1584-1600.
Silva et al., "Antisense oligonucleotide therapeutics in neurodegenerative diseases: the case of polyglutamine disorders," Brain, 2020, 143: 407-429.
Smith and Zain, "Therapeutic Oligonucleotides: State of the Art," Annual Review of Pharmacology and Toxicology, Jan. 2019, 59: 605-630.
Vester et al., "LNA (locked nucleic acid): high-affinity targeting of complementary RNA and DNA," Biochemistry 2004, 43(42): 13233-13241.
Yamakawa et al., "Development and Clinical Trials of Nucleic Acid Medicines for Pancreatic Cancer Treatment," Int J Mol Sci., 2019, 20:4224, 12 pages.
Basiri, B., et al., "Bioanalytical LC-MS Of Oligonucleotides", A Dissertation Submitted to the Graduate Faculty of The University of Georgia in Partial Fulfillment of the Requirements for the Degree, Doctor of Philosophy, Athens, Georgia (2017); 61 pages.
Chen, B., et al., "Evaluation of mobile phase composition for enhancing sensitivity of targeted quantification of oligonucleotides using ultrahigh performance liquid chromatography and mass spectrometry: application to phosphorothioate deoxyribonucleic acid", Journal of Chromatography A (2013); 1288: 73-81.
Vallejos-Almirall, A., et al., "Development of liquid chromatography tandem mass spectrometry method to quantify cyclobutane pyrimidine dimer photolyase activity by detection of 15mer oligonucleotide as reaction product", Journal of Chromatography A (2020); 1611(460577); 8 pages.

* cited by examiner

Unmodified sequence:
TCTCCCAGCGTGCGCCAT
(SEQ ID NO: 4)

Oxygen
MW: 15.999405
EM: 15.99491

Sulfur
MW: 32.064787
EM: 31.97207

Oblimersen

T*C*T*C*C*C*A*G*C*G*T*G*C*G*C*C*A*T
(SEQ ID NO: 5)

$a_x\text{-B (PS)} = a_x\text{-B (unmodified)} + (x-1)*(-15.9994+32.0648)$ $w_x \text{ (PS)} = w_x \text{ (unmodified)} + (x)*(-15.9994+32.0648)$ $y_x \text{ (PS)} = y_x \text{ (unmodified)} + (x-1)*(-15.9994+32.0648)$ $d_x\text{-H}_2\text{O (PS)} = d_x\text{-H}_2\text{O (unmodified)} + (x)*(-15.9994+32.0648)$ Unmodified sequence:
TCTCCCAGCGTGCGCCAT
(SEQ ID NO: 4)

Oblimersen

T*C*T*C*C*C*A*G*C*G*T*G*C*G*C*C*A*T
(SEQ ID NO: 5)

| Charge | Unmodified sequence | | | | Full PS-modified sequence | | | |
|---|---|---|---|---|---|---|---|---|
| | a-B | w | y | d-H₂O | a-B | w | y | d-H₂O |
| -1 | | 321.05 | 241.08 | 303.04 | | | | 319.10 |
| -2 | 401.07 | 634.11 | 554.14 | 592.08 | | 337.11 | 241.08 | 559.95 |
| -3 | 690.12 | 923.15 | 843.19 | 896.13 | 352.88 | 601.97 | 505.94 | 847.93 |
| -4 | 994.17 | 1212.20 | 1132.23 | 1185.18 | 625.86 | 874.95 | 778.92 | 1120.91 |
| -5 | 1283.21 | 1541.25 | 1461.28 | 1474.22 | 913.84 | 1147.94 | 1051.90 | 1393.89 |
| -6 | 1572.26 | 1830.30 | 1750.33 | 1763.27 | 1186.82 | 1460.92 | 1364.89 | 1666.87 |
| -7 | 1861.30 | 2159.35 | 2079.38 | 2076.32 | 1459.80 | 1733.90 | 1637.87 | 1963.87 |
| -8 | 2174.36 | 2463.39 | 2383.43 | 2405.38 | 1732.78 | 2046.89 | 1950.86 | 2276.85 |
| -9 | 2503.41 | 2792.45 | 2712.48 | 2694.42 | 2029.77 | 2334.87 | 2238.84 | 2549.83 |
| -10 | 2792.46 | 3081.49 | 3001.53 | 3023.48 | 2342.76 | 2647.86 | 2551.83 | 2862.82 |
| -11 | 3121.51 | 3410.54 | 3330.58 | 3327.52 | 2615.74 | 2920.84 | 2824.81 | 3150.80 |
| -12 | 3425.56 | 3723.60 | 3643.63 | 3656.57 | 2928.73 | 3233.82 | 3137.79 | 3463.79 |
| -13 | 3754.61 | 4012.65 | 3932.68 | 3945.62 | 3216.71 | 3530.82 | 3434.78 | 3736.77 |
| -14 | 4043.66 | 4301.69 | 4221.73 | 4274.67 | 3529.69 | 3803.80 | 3707.76 | 4049.76 |
| -15 | 4372.71 | 4590.74 | 4510.77 | 4563.72 | 3802.67 | 4076.78 | 3980.75 | 4322.74 |
| | | | | | 4115.66 | 4349.76 | 4253.73 | |

FIG. 19C

USE OF LIQUID CHROMATOGRAPHY AND MASS SPECTROMETRY TO CHARACTERIZE OLIGONUCLEOTIDES

CROSS REFERENCE TO RELATED APPLICATIONS

This application claims the benefit of priority to U.S. Provisional Patent Application Ser. No. 62/968,368 filed on Jan. 31, 2020, the contents of which are hereby incorporated by reference in their entirety.

TECHNICAL FIELD

The disclosure relates the fields of molecular biology and therapeutics.

INCORPORATION BY REFERENCE OF SEQUENCE LISTING

The contents of the text file submitted electronically herewith are incorporated herein by reference in their entirety: A computer readable format copy of the Sequence Listing (filename: REGE-020-001US_SeqList_ST25.txt, date recorded: Jan. 27, 2021, file size 6 kilobytes).

BACKGROUND

Therapeutic oligonucleotides such as antisense oligonucleotides and double stranded RNAs (dsRNA) have been under clinical development for approximately the past thirty years. Recently, a number of therapeutic oligonucleotides have been approved by the Food and Drug administration for administration to patients. However, active pharmaceutical ingredients (APIs) and drug products, including therapeutic oligonucleotides, must meet certain quality thresholds in order be suitable for administration to subjects. There is thus a need in the art for methods to characterize oligonucleotide compositions. This disclosure provides additional methods for characterizing oligonucleotide compositions with a high degree of sensitivity and precision.

SUMMARY

The disclosure provides methods of characterizing a sample comprising a population of oligonucleotides of interest, comprising (a) providing a sample comprising a population of oligonucleotides of interest of identical sequence; (b) subjecting the sample to liquid chromatography and mass spectrometry, thereby generating at least one mass spectrogram corresponding to the population of oligonucleotides of interest; and (c) determining a percentage of total oligonucleotides in the sample corresponding to the population of oligonucleotides of interest.

In some embodiments of the methods of the disclosure, the sample further comprises at least one impurity comprising at least one additional population of oligonucleotides. In some embodiments, the additional population of oligonucleotides comprises a fragmentation product of or synthesis byproduct of the oligonucleotides of interest.

In some embodiments of the methods of the disclosure, the methods further comprise generating a mass spectrogram corresponding to the at least one additional population of oligonucleotides and determining the percentage of total oligonucleotides in the sample corresponding to the at least one additional population of oligonucleotides.

In some embodiments of the methods of the disclosure, the oligonucleotides of interest are deoxyribonucleic acids (DNA), ribonucleic acids (RNA), or DNA-RNA hybrids. In some embodiments, the oligonucleotides of interest are single stranded. In some embodiments, the oligonucleotides of interest are double stranded. In some embodiments, the oligonucleotides of interest comprise a hairpin or stem-loop structure. In some embodiments, the oligonucleotides of interest are between 15 and 100 nucleotides in length.

In some embodiments of the methods of the disclosure, the oligonucleotides of interest are therapeutic oligonucleotides. In some embodiments, the therapeutic oligonucleotides comprise antisense oligonucleotides (ASO), dsRNAs, siRNAs, aptamers or microRNAs.

In some embodiments of the methods of the disclosure, the oligonucleotide of interest comprise at least one modification. In some embodiments, the at least one modification is at the 5' end, the 3' end, or both, of the oligonucleotide of interest. In some embodiments, the at least one modification comprises a modification to at least one internal nucleobase of the oligonucleotide of interest. In some embodiments the at least one modification affects binding affinity, binding specificity, stability, pharmacokinetics or toxicity of the oligonucleotides of interest. In some embodiments, the at least one modification comprises a locked nucleic acid (LNA), a phosphorothioate (PS) linkage, a terminal 5' or 3' phosphate (PO), a 5' methyl (5-Me) modification, a 2'-O-Methyl (2'-O-Me) modification, a 2'-O-methoxyethyl (2'-MOE) modification, a constrained ethyl (CET) nucleoside analog, polyethylene glycol (PEG) or a combination thereof.

In some embodiments of the methods of the disclosure, the liquid chromatography comprises hydrophilic interaction liquid chromatography (HILIC). In some embodiments, the HILIC comprises a mobile phase buffer comprising ammonium acetate. In some embodiments, the mobile phase comprises a first buffer comprising 15 mM ammonium acetate in 70% acetonitrile (ACN) and a second buffer comprising 15 mM ammonium acetate in 30% (ACN). In some embodiments, the HILIC comprises a mobile phase buffer comprising ammonium formate. In some embodiments, the mobile phase comprises a first buffer comprising 15 mM ammonium formate in 70% acetonitrile (ACN) and a second buffer comprising 15 mM ammonium formate in 30% (ACN). In some embodiments, HILIC separation comprises a column temperature of between 23 and 50° C. In some embodiments, HILIC separation comprises a column temperature of 30° C. In some embodiments, the HILIC comprises a column with a solid phase with a mean nominal particle size of 3 µm, a median particle pore size of 200 Å, a 2 mm inner diameter, and a 150 mm length column.

In some embodiments of the methods of the disclosure, the liquid chromatography comprises Ion-pairing Reversed-Phase Liquid Chromatography (IP-RPLC). In some embodiments, the IP-RPLC comprises mobile phase buffer comprising Hexafluoroisopropanol (HFIP) and 5 mM N,N-Diisopropylethylamine (DIEA). In some embodiments, the mobile phase comprises a first buffer comprising 50 mM HFIP and 5 mM DIEA in water and a second buffer comprising 50 mM HFIP and 5 mM DIEA in acetonitrile. In some embodiments, the IP-RPLC comprises a column with a mean nominal particle size of 1.7 µm, a median particle pore size of 130 Å, a column length 100 mm and a 2.1 mm inner diameter. In some embodiments, the IP-RPLC comprises a 1.7 µm, Oligo-XT 100 Å, 50×2.1 mm column.

In some embodiments of the methods of the disclosure, the mass spectrometry comprises electrospray ionization (ESI). In some embodiments, the ESI comprises nano-flow ESI.

In some embodiments of the methods of the disclosure, the liquid chromatography further comprises ultraviolet (UV) detection of the sample.

In some embodiments of the methods of the disclosure, the mass spectrometry is tandem mass spectrometry (MS/MS). In some embodiments, the MS/MS comprises Data Dependent Acquisition (DDA). In some embodiments, the MS/MS comprises fragmentation of the population of oligonucleotides of interest, the at least additional population of oligonucleotides, or a combination thereof. In some embodiments, the fragmentation comprises higher-energy collisional dissociation (HCD). In some embodiments, the HCD comprises a normalized collision energy (NCE) of 15% to 35%. In some embodiments, the HCD comprises and NCE of 20%.

In some embodiments of the methods of the disclosure, step (c) comprises determining the intact mass of the oligonucleotides of interest. In some embodiments, step (c) further comprises determining the intact mass of the at least one additional population of oligonucleotides. In some embodiments, step (c) comprises determining the structure of the oligonucleotides of interest using mass spectrometry. In some embodiments, step (c) further comprises determining the structure of the at least one additional population of oligonucleotides. In some embodiments, the structure includes nucleotide sequence, modification or a combination thereof.

The disclosure provides methods of making a composition comprising an oligonucleotide of interest comprising: (a) synthesizing the oligonucleotide of interest; and (b) characterizing the oligonucleotide of interest using the methods of the disclosure.

In some embodiments of the methods of the disclosure, at least 90%, at least 91%, at least 92%, at least 93%, at least 94%, at least 95%, at least 96%, at least 97%, at least 98%, at least 98.5%, at least 99%, at least 99.5%, at least 99.6%, at least 99.7%, at least 99.8% or at least 99.9% of the total oligonucleotides in the composition are the oligonucleotide of interest. In some embodiments, the method further comprises adding a pharmaceutically acceptable carrier, diluent or excipient.

The disclosure provides compositions comprising oligonucleotides of interest made or characterized using the methods described herein.

The disclosure provides methods of treating a subject in need thereof, comprising administering the compositions of the disclosure.

The composition of claim 46 for use in a method of treating a subject in need thereof.

The composition of claim 46 for use in the manufacture of a medicament for treating a subject in need thereof.

The disclosure provides methods of characterizing a sample, comprising: (a) providing a sample comprising a population of oligonucleotides of interest of identical sequence and/or modification, and at least one impurity comprising an additional population of oligonucleotides; (b) subjecting the sample to liquid chromatography and tandem mass spectrometry (MS/MS), wherein the liquid chromatography comprises: (i) hydrophilic interaction liquid chromatography (HILIC) comprising a mobile phase, wherein a first buffer comprises 15 mM ammonium formate or ammonium acetate in 70% acetonitrile (ACN), and a second buffer comprises 15 mM ammonium formate or ammonium acetate in 30% ACN, or (ii) Ion-pairing Reversed-Phase Liquid Chromatography (IP-RPLC) comprising a mobile phase, wherein a first buffer comprises 50 mM Hexafluoroisopropanol (HFIP) and 5 mM N,N-Diisopropylethylamine (DIEA) in water and a second buffer comprises 50 mM HFIP and 5 mM DIEA in acetonitrile; wherein the MS/MS comprises fragmentation of the population of oligonucleotides of interest and the additional population of oligonucleotides in the sample using higher-energy collisional dissociation (HCD) comprising a normalized collisional energy (NCE) of 15% to 35%, thereby generating at least one mass spectrogram corresponding to the population oligonucleotides of interest and the additional population of oligonucleotides; and (c) determining a percentage of total oligonucleotides in the sample corresponding to the population of oligonucleotides of interest.

In some embodiments of the methods of the disclosure, the additional population of oligonucleotides comprises a fragmentation product of or synthesis byproduct of the oligonucleotides of interest.

In some embodiments of the methods of the disclosure, the oligonucleotides of interest are deoxyribonucleic acids (DNA), ribonucleic acids (RNA), or DNA-RNA hybrids. In some embodiments, the oligonucleotides of interest are single stranded, double stranded, or a combination thereof. In some embodiments, the oligonucleotides of interest comprise a hairpin or stem-loop structure. In some embodiments, the oligonucleotides of interest are between 15 and 100 nucleotides in length.

In some embodiments of the methods of the disclosure, the oligonucleotides of interest are therapeutic oligonucleotides. In some embodiments, the therapeutic oligonucleotides comprise antisense oligonucleotides (ASO), dsRNAs, siRNAs, aptamers or microRNAs.

In some embodiments of the methods of the disclosure, the oligonucleotides of interest comprise at least one modification. In some embodiments, the at least one modification is at the 5' end, the 3' end, or both, of the oligonucleotide of interest. In some embodiments, the at least one modification comprises a modification to at least one internal nucleobase of the oligonucleotides of interest. In some embodiments, the at least one modification affects binding affinity, binding specificity, stability, pharmacokinetics or toxicity of the oligonucleotides of interest. In some embodiments, the at least one modification comprises a locked nucleic acid (LNA), a phosphorothioate (PS) linkage, a terminal 5' or 3' phosphate (PO), a 5' methyl (5-Me) modification, a 2'-O-Methyl (2'-O-Me) modification, a 2?-O-methoxyethyl (2'-MOE) modification, a constrained ethyl (cET) nucleoside analog, polyethylene glycol (PEG) or a combination thereof.

In some embodiments of the methods of the disclosure, the HILIC chromatography comprises a column temperature of 30° C. In some embodiments, the HILIC chromatography comprises a column with a solid phase with a mean nominal particle size of 3 μm, a median particle pore size of 200 Å, a 2 mm inner diameter, and a 150 mm length column. In some embodiments, the IP-RPLC comprises a 1.7 μm, Oligo-XT 100 Å, 50×2.1 mm column.

In some embodiments of the methods of the disclosure, the MS/MS comprises electrospray ionization (ESI). In some embodiments, the ESI comprises nano-flow ESI. In some embodiments, the MS/MS comprises Data Dependent Acquisition (DDA).

In some embodiments of the methods of the disclosure, the liquid chromatography further comprises ultraviolet (UV) detection of the sample.

In some embodiments of the methods of the disclosure, step (c) comprises determining the intact mass and/or structure of the population of oligonucleotides of interest and the additional population of oligonucleotides.

The disclosure provides compositions for use in a method of treating a subject in need thereof, comprising administering the compositions of the disclosure.

The disclosure provides compositions for use in the manufacture of a medicament for a method of treating a subject in need thereof, comprising administering the compositions of the disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 19A-19C show the conversion of fragment ions based on phosphorothioate (PS) oligonucleotide modification. In FIG. 19C, charge states and corresponding masses of unmodified and modified Oblimersen fragments are shown.

DETAILED DESCRIPTION

Figure 1:
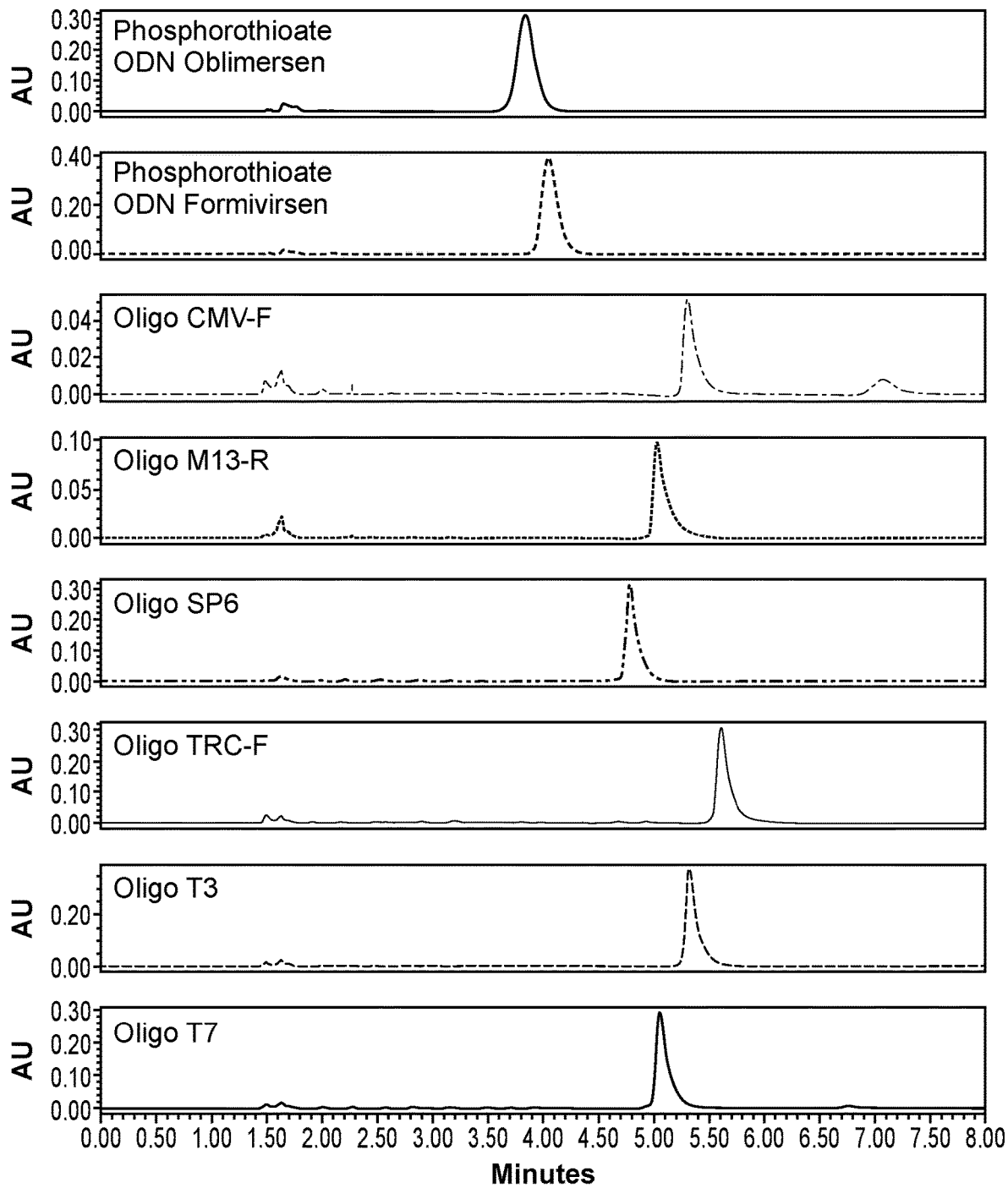
FIG. 1 is a series of chromatograms showing hydrophilic interaction liquid chromatography with ultraviolet detection (HILIC-UV) of phosphorothioate (PS) modified oligonucleotides and unmodified oligonucleotides using a Phenomenex Luna-HILIC column and ammonium acetate in the mobile phase.

The inventors have found that oligonucleotide compositions, including compositions comprising modified oligonucleotides, can be characterized with a high degree of accuracy using liquid chromatography and mass spectrometry. Oligonucleotide compositions can contain impurities, such as degradation products of full-length oligonucleotides, that are introduced by storage conditions, or additional products stemming from oligonucleotide synthesis that have errors in nucleotide sequence or modifications. The methods described herein can be used to determine the identity and abundance of these impurities in oligonucleotide compositions described herein.

Accordingly, the disclosure provides methods of characterizing a sample comprising a population of oligonucleotides of interest, comprising: (a) providing a sample comprising a population of oligonucleotides of interest of identical sequence; (b) subjecting the sample to liquid chromatography and mass spectrometry, thereby generating at least one mass spectrogram corresponding to the oligonucleotides of interest; and (c) determining a percentage of total oligonucleotides in the sample corresponding to the population of oligonucleotides of interest.

In some embodiments, the sample further comprises at least one impurity, for example comprising an additional population of oligonucleotides, and this additional population is also analyzed using the methods described herein. In some embodiments, the methods further comprise generating a mass spectrogram corresponding to the at least one impurity and determining the percentage of total oligonucleotides in the sample corresponding to the at least one impurity.

In some embodiments, the methods of characterizing the sample comprise (a) providing a sample comprising a population of oligonucleotides of interest of identical sequence and at least one impurity comprising an additional population of oligonucleotides that differ in sequence from the oligonucleotides of interest; (b) subjecting the sample to liquid chromatography and mass spectrometry, thereby generating at least one mass spectrogram; and (c) determining a percentage of total oligonucleotides in the sample corresponding to the population of oligonucleotides of interest. In some embodiments, the additional population of oligonucleotides comprises one or fragmentation products of or synthesis byproducts of the oligonucleotides of interest.

In some embodiments, step (c) comprises determining the intact mass of the oligonucleotides of interest, and optionally the oligonucleotides corresponding to the at least one impurity. In some embodiments, determining a percentage of total oligonucleotides in the sample corresponding to the population of oligonucleotides of interest comprises determining the structure of the oligonucleotides of interest, and optionally the oligonucleotides corresponding to the at least one impurity, using mass spectrometry. In some embodiments, the structure includes nucleotide sequence, modification or a combination thereof.

The disclosure further provides methods of making a composition comprising an oligonucleotide of interest comprising (a) synthesizing the oligonucleotide of interest using any suitable methods known in the art thereby providing a sample comprising a population of the oligonucleotides of interest; and (b) characterizing the sample comprising the population the oligonucleotide of interest using the methods of described herein. In some embodiments, the methods comprise selecting a sample comprising a population of the oligonucleotides of interest with desired characteristics, as determined by the methods described herein. For example, the methods can include selecting a sample with desired purity of the oligonucleotides of interest.

The disclosure further provides pharmaceutical compositions comprising oligonucleotides of interest, and methods of making and using same to treat a disease or disorder in a subject. In some embodiments, the subject is human.

Definitions

As used herein, the terms "oligonucleotide," "oligo," "polynucleotide," "nucleotide sequence" and "nucleic acid" are used interchangeably and encompass both RNA and DNA, including cDNA, genomic DNA, mRNA, and synthetic (e.g., chemically synthesized) DNA or RNA, and chimeras or mimetics of RNA and DNA. The terms refer to a chain of nucleotides without regard to length of the chain. The nucleic acid can be double-stranded or single-stranded. Where single-stranded, the nucleic acid can be a sense strand or an antisense strand. The present invention further provides a nucleic acid that is the complement (which can be either a full complement or a partial complement) of a nucleic acid, nucleotide sequence, or polynucleotide of the disclosure.

These terms also include oligonucleotides comprising modified nucleosides or nucleotides, for example those that have nitrogenous heterocyclic bases or base analogs, covalently linked by standard phosphodiester bonds or other linkages. In a nucleic acid, the backbone may be made up of a variety of linkages, including one or more of sugar-phosphodiester linkages, peptide-nucleic acid (PNA) linkages (PCT No. WO 95/32305), phosphorothioate linkages, methylphosphonate linkages, or combinations thereof. Sugar moieties in a nucleic acid may be ribose, deoxyribose, or similar compounds with substitutions, e.g., 2' methoxy and 2' halide (e.g., 2'-F) substitutions. Nitrogenous bases may be conventional bases (A, G, C, T, U), analogs thereof (e.g., inosine; The Biochemistry of the Nucleic Acids 5-36, Adams et al., ed., 11$^{th}$ ed., 1992), derivatives of purine or pyrimidine bases (e.g., N$^4$-methyl deoxyguanosine, deaza- or aza-purines, deaza- or aza-pyrimidines, pyrimidines or purines with altered or replacement substituent groups at any of a variety of chemical positions, e.g., 2-amino-6-methyl-aminopurine, O$^6$-methylguanine, 4-thio-pyrimidines, 4-amino-pyrimidines, 4-dimethylhydrazine-pyrimidines, and O$^4$-alkyl-pyrimidines, or pyrazolo-compounds, such as unsubstituted or 3-substituted pyrazolo[3,4-d]pyrimidine (e.g. U.S. Pat. Nos. 5,378,825, 6,949,367 and PCT No. WO 93/13121). Nucleic acids may include "abasic" positions in which the backbone does not have a nitrogenous base at one or more locations (U.S. Pat. No. 5,585,481), e.g., one or more abasic positions may form a linker region that joins separate oligonucleotide sequences together. A nucleic acid may comprise only conventional sugars, bases, and linkages as found in conventional RNA and DNA, or may include conventional components and substitutions (e.g., conventional bases linked by a 2' methoxy backbone, or a polymer containing a mixture of conventional bases and one or more analogs).

"Oligonucleotide" may refer to nucleic acid polymers of any length. In some embodiments, oligonucleotides are made of less than 1,000 nucleotides (nt), including those in a size range from about 5-200 nucleotides in length those having lower limit of about 2 to 5 nt and an upper limit of about 500 to 900 nt, or a lower limit of 5 to 15 nt and an upper limit of 50 to 500 nt, or a 10 to 20 nt lower limit and a 25 to 150 nt upper limit.

An "isolated oligonucleotide" refers to a nucleotide sequence (e.g., DNA or RNA) that is not immediately contiguous with nucleotide sequences with which it is immediately contiguous (one on the 5' end and one on the 3' end) in the naturally occurring genome of the organism from which it is derived. The term therefore includes, for example, a recombinant DNA that is incorporated into a vector or which exists as a separate molecule (e.g., an oligonucleotide produced by chemical synthesis), independent of other sequences. It also includes a recombinant DNA that is part of a hybrid nucleic acid encoding an additional polypeptide or peptide sequence. "Isolated" does not mean that the preparation is technically pure (homogeneous), but it is sufficiently pure to provide the nucleic acid in a form in which it can be used for the intended purpose.

The term "fragment," as applied to an oligonucleotide, will be understood to mean a nucleotide sequence of reduced length relative to a reference nucleic acid or nucleotide sequence and comprising, consisting essentially of, and/or consisting of a nucleotide sequence of contiguous nucleotides identical or almost identical (e.g., 90%, 92%, 95%, 98%, 99% identical) to the reference nucleic acid or nucleotide sequence. Such a nucleic acid fragment according to the invention may be, where appropriate, included in a larger polynucleotide of which it is a constituent. In some embodiments, such fragments can comprise, consist essentially of, and/or consist of oligonucleotides having a length of at least about 3, 4, 5, 6, 7, 8, 9, 10, 11, 12, 13, 14, 15, 20, 25, 30, 35, 40, 45, 50, 75, 100, 150, 200, or more consecutive nucleotides of a nucleic acid or nucleotide sequence.

As used herein, the term "gene" refers to a nucleic acid molecule capable of being used to produce mRNA, antisense RNA, miRNA, and the like. Genes may or may not be capable of being used to produce a functional protein. Genes can include both coding and non-coding regions (e.g., introns, regulatory elements, promoters, enhancers, termination sequences and 5' and 3' untranslated regions).

As used herein, "messenger RNA" or "mRNA" refers to a single-stranded molecule of RNA that corresponds to the genetic sequence of a gene, and is read by a ribosome in the process of synthesizing a protein.

As used herein, "complementary" oligonucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. For example, the sequence "A-G-T" binds to the complementary sequence "T-C-A." It is understood that two oligonucleotides may hybridize to each other even if they are not completely complementary to each other, provided that each has at least one region that is substantially complementary to the other.

The terms "complementary" or "complementarity," as used herein, refer to the natural binding of oligonucleotides under permissive salt and temperature conditions by base-pairing. Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands. As used herein, the terms "substantially complementary" or "partially complementary" mean that two nucleic acid sequences are complementary at least about 50%, 60%, 70%, 80% or 90% of their nucleotides. The terms "substantially complementary" and "partially complementary" can also mean that two nucleic acid sequences can hybridize under high stringency conditions and such conditions are well known in the art.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part* 1 (Griffin, A. M, and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

Optimal alignment of sequences for aligning a comparison window are well known to those skilled in the art. Percent sequence identity is represented as the identity fraction multiplied by 100. The comparison of one or more polynucleotide sequences may be to a full-length polynucleotide sequence or a portion thereof, or to a longer polynucleotide sequence. For example, percent identity may be determined using BLASTX version 2.0 for translated nucleotide sequences and BLASTN version 2.0 for polynucleotide sequences. Useful methods for determining sequence identity are also disclosed in Guide to Huge Computers (Martin J. Bishop, ed., Academic Press, San Diego (1994)), and Carillo, H., and Lipton, D., (*Applied Math* 48:1073(1988)). Computer programs for determining sequence identity include but are not limited to the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; (Altschul et al., *J. Mol. Biol.* 215:403-410 (1990)); version 2.0 or higher of BLAST programs allows the introduction of gaps (deletions and insertions) into alignments; for peptide sequence BLASTX can be used to determine sequence identity; and, for polynucleotide sequence BLASTN can be used to determine sequence identity.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps). In some embodiments, "percent identity" can refer to the percentage of identical amino acids in an amino acid sequence.

As used herein, the term "substantially identical" or "corresponding to" means that two nucleic acid sequences have at least 60%, 70%, 80% or 90% sequence identity. In some embodiments, the two nucleic acid sequences can have at least 85%, 90%, 95%, 96%, 97%. 98%, 99% or 100% of sequence identity.

All publications, patents, and patent applications mentioned in this specification are herein incorporated by reference to the same extent as if each individual publication, patent, or patent application was specifically and individually indicated to be incorporated by reference.

Oligonucleotides of Interest

The disclosure provides oligonucleotides of interest, and compositions comprising populations of oligonucleotides of interest, that have been characterized using the liquid chromatography and mass spectrometry methods described herein. Characterization of oligonucleotides of interest includes, inter alia, determining the intact mass, structure and sequence of nucleotides of interest, and the percentage of total oligonucleotides in a composition that are the oligonucleotide of interest.

In some embodiments, the oligonucleotide of interest is a therapeutic oligonucleotide. Therapeutic oligonucleotides include, but are not limited to, messenger RNAs (mRNAs), antisense oligonucleotides (ASO), double stranded RNAs (dsRNAs) such as small interfering RNAs (siRNAs), and microRNAs. Therapeutic oligonucleotides are administered to a subject to modulate expression of a target gene, thereby treating a disease or disorder of the subject. Subjects can include mammals, such as rats, mice, primates and humans. In some embodiments, the subject is human.

As used herein "antisense oligonucleotides" are oligonucleotides that target mRNAs in cells as substrates for the cellular enzyme RNase H, and thereby cause specific degradation of the targeted mRNA. In some embodiments, the antisense oligonucleotide comprises a single stranded DNA molecule. Without wishing to be bound by theory, it is thought that this single stranded DNA molecule hybridizes to a target RNA, inducing RNase H cleavage of the DNA/RNA hybrid. Both phosphodiester and phosphorothioate-linked DNA can activate endogenous RNase H, thereby cleaving the targeted RNA. Alternatively, antisense oligonucleotides can act through steric hindrance, i.e. by physically blocking translation or splicing of the target mRNA.

Antisense oligonucleotides of the disclosure comprise a nucleotide complementary to, or substantially complementary to a sequence of a target RNA (e.g., mRNA or non-coding RNA produced by a target gene). In some embodiments, antisense oligonucleotides are between 5 and 50 nucleotides in length, between 8 and 50 nucleotides in length, between 10 and 40 nucleotides in length, between 15 and 40 nucleotides in length, between 20 and 30 nucleotides in length or between 18 and 30 nucleotides in length.

In some embodiments, the therapeutic oligonucleotide is a dsRNA or siRNA. RNA interference (RNAi) is a process by which double-stranded RNA (dsRNA) is used to silence gene expression. While not wishing to be bound by theory, RNAi begins with the cleavage of longer dsRNAs into small interfering RNAs (siRNAs) by an RNaseIII-like enzyme, dicer. siRNAs are dsRNAs that are usually about 19 to 28 nucleotides, or 20 to 25 nucleotides, or 21 to 22 nucleotides in length, and often contain 2-nucleotide 3' overhangs, and 5' phosphate and 3' hydroxyl termini. One strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. Therefore, the siRNA strand that is incorporated into RISC is known as the guide strand or the antisense strand. The other siRNA strand, known as the passenger strand or the sense strand, is eliminated from the siRNA and is at least partially homologous to the target mRNA. Those of skill in the art will recognize that, in principle, either strand of an siRNA can be incorporated into RISC and function as a guide strand. However, siRNA design (e.g., decreased siRNA duplex stability at the 5' end of the antisense strand) can favor incorporation of the antisense strand into RISC.

RISC-mediated cleavage of mRNAs having a sequence at least partially complementary to the guide strand leads to a decrease in the steady state level of that mRNA and of the corresponding protein encoded by this mRNA. Alternatively, RISC can also decrease expression of the corresponding protein via translational repression without cleavage of the target mRNA. Other RNA molecules and RNA-like molecules can also interact with RISC and silence gene expression Examples of other RNA molecules that can interact with RISC include short hairpin RNAs (shRNAs), single-stranded siRNAs, microRNAs (miRNAs), and dicer-substrate 27-mer duplexes. The term "siRNA" as used herein refers to a double-stranded interfering RNA unless otherwise noted. Examples of RNA-like molecules that can interact with RISC include RNA molecules containing one or more chemically modified nucleotides, one or more deoxyribonucleotides, and/or one or more non-phosphodiester linkages.

In some embodiments, the therapeutic oligonucleotide comprises an siRNA or dsRNA. In some embodiments, the siRNA or dsRNA has a sense strand and an antisense strand, and the sense and antisense strands comprise a region of at least near-perfect contiguous complementarity of at least 19 nucleotides. In some embodiments, the siRNA or dsRNA has a sense strand and an antisense strand, and the antisense strand comprises a region of at least near-perfect contiguous complementarity of at least 19 nucleotides to a target sequence in a gene, and the sense strand comprises a region of at least near-perfect contiguous identity of at least 19 nucleotides with a target sequence of the gene, respectively. In some embodiments, the siRNA or dsRNA comprises a region of at least 13, 14, 15, 16, 17, or 18 contiguous nucleotides having percentages of sequence complementarity to or, having percentages of sequence identity with the penultimate 13, 14, 15, 16, 17, or 18 nucleotides, respectively, of the 3' end of the corresponding target sequence within an mRNA.

Techniques for selecting target sequences for siRNAs and dsRNAs are known in the art, and provided as web-based design tools at, for example, the Invitrogen, Dharmacon, Integrated DNA Technologies, Genscript, or Proligo web sites. Initial search parameters can include G/C contents between 35% and 55% and siRNA lengths between 19 and 27 nucleotides. The target sequence may be located in the coding region or in the 5' or 3' untranslated regions of the target mRNA.

In some embodiments, the therapeutic oligonucleotide is a microRNA. MicroRNAs (miRNAs) are non-protein coding RNAs, generally of between about 18 to about 25 nucleotides in length. These miRNAs direct cleavage in trans of target transcripts, negatively regulating the expression of target genes involved in various regulation and development pathways. Many microRNA genes (MIR genes) have been identified and made publicly available in a database (miRBase; microrna.sanger.ac.uk/sequences). miRNAs are also described in U.S. Patent Publications 2005/0120415 and 2005/144669A1, the entire contents of which are incorporated by reference herein.

Genes encoding miRNAs yield primary miRNAs (termed a "pri-miRNA") of 70 to 300 bp in length that can form imperfect stemloop structures. A single pri-miRNA may contain from one to several miRNA precursors. In animals, pri-miRNAs are processed in the nucleus into shorter hairpin RNAs of about 65 nt (pre-miRNAs) by the RNaseIII enzyme Drosha and its cofactor DGCR8/Pasha. The pre-miRNA is then exported to the cytoplasm, where it is further processed by another RNaseIII enzyme, Dicer, releasing a miRNA/miRNA* duplex of about 22 nt in size.

Exemplary, but non-limiting, therapeutic RNAs include therapeutic antisense RNAs such as Fomivirsen (also known as Vitravene™), which can be used to treat cytomegalovirus retinitis; Mipomersen (Kynamro™) which can be used to treat homozygous familial hypercholesterolemia; Nusinersen (Spinraza®), which is used to treat spinal muscular atrophy; Patisiran (Onpattro®), which is used to treat polyneuropathy; Inotersen (Tegsedi®), which is used to treat nerve damage in adults with heredityar transthyretin-mediated amyloidosis; Eteplirsen (Exondys 51®), which is used to treat Duchenne Muscular Dystrophy; Golodirsen (Vyondys 53®), which is used to treat Duchenne Muscular Dystrophy; Givosiran (Givlaari®), and which is used to treat acute hepatic porphyria. Additional therapeutic RNAs include Pegaptanib (Mucagen®), which can be used to treat age-related macular degeneration, In some embodiments, the therapeutic RNA is personalized, i.e. has been developed for a single patient. An exemple of a unique, personalized therapeutic RNA includes Milasen, developed to treat a specific CLN7 mutation.

Exemplary, but non-limiting RNA therapies include cancer vaccines, as well as vaccines for infectious diseases. For example, Heblisav-B® is a recombinant Hepatitis B vaccine, and both Moderna, and Pfizer and BioNTech, have developed mRNA vaccines for severe acute respiratory syndrome 2 (SARS-CoV-2), the virus causing COVID-19. mRNAs can also be used in mRNA-based gene therapies.

"Modulating mRNA expression" as used herein, includes administering an amount of therapeutic oligonucleotide sufficient reduce translation of the target mRNA into protein, for example through mRNA cleavage and degradation or through direct inhibition of translation. The reduction in expression of the target mRNA or the corresponding protein is commonly referred to as "knock-down" and is reported relative to levels present following administration or expression of a non-targeting control RNA (e.g., a non-targeting control siRNA). Knock-down or reduction can be complete or partial, and any degree of knock-down is envisaged as within the scope of the oligonucleotides of the disclosure.

The term "inhibit" or "reduce" or grammatical variations thereof as used herein refers to a decrease or diminishment in the specified level or activity of at least about 15%, 25%, 35%, 40%, 50%, 60%, 75%, 80%, 90%, 95% or more. In some embodiments, the inhibition or reduction results in little or essentially no detectible activity (at most, an insignificant amount, e.g., less than about 10% or even 5%).

In some embodiments, the oligonucleotide of interest is not therapeutic. For example, the oligonucleotides of interest of the disclosure include oligonucleotides of interest used for in vitro manipulation or labeling of cells.

Oligonucleotide Modifications

Provided herein are oligonucleotides of interest comprising one or more modified nucleobases. This modified nucleobase can be at the 5' end of the oligonucleotide, the 3' end of the oligonucleotide, an internal nucleobase, or any combination thereof. The modification can be to a purine or a pyrimidine. The modification can be to any one of adenine (A), cytosine (C), thymine (T), guanine (G) or uracil (U) or any combination thereof.

As used herein, the term "nucleobase" refers to a compound (e.g., adenosine) commonly found in DNA or RNA, consisting of a purine or pyrimidine base linked to a sugar. A nucleoside comprises a nitrogenous base covalently attached to a sugar (ribose or deoxyribose) but without the phosphate group. A nucleotide comprises a nitrogenous base, a sugar (ribose or deoxyribose) and one to three phosphate groups.

In some embodiments, at least 1, 2, 3, 4, 5, 6, 7, 8, 9, 10, 11, 12, 13, 14, 15, 16, 17, 18, 19, 20, 21, 22, 23, 24, 25, 26 27, 28, 29 or 30 nucleobases of the oligonucleotide of interest are modified. In some embodiments, for example those embodiments where the oligonucleotide of interest is greater than 30 nucleotides in length, more than 30 nucleobases of the oligonucleotide of interest can be modified. In some embodiments, all nucleobases of the oligonucleotide of interest are modified. In some embodiments, one nucleobase of the oligonucleotide of interest is modified, for example the terminal 5' or 3' nucleobase, commonly referred to as the 5' or 3' end.

In some embodiments, modification of one or more nucleobases of the oligonucleotide of interest affects binding affinity, binding specificity (e.g. to a target mRNA), stability, pharmacokinetics or toxicity of the oligonucleotide of interest. In some embodiments, the toxicity is hepatotoxicity. Binding affinity refers to the strength of the binding interaction between a single biomolecule (e.g. protein or DNA) to its ligand/binding partner, while binding specificity refers to the ability of the oligonucleotide of interest to bind one molecule in preference over other molecules.

In some embodiments, the modified oligonucleotides of interest are substantially nontoxic and non-mutagenic. In some embodiments, the modified oligonucleotides of interest are non-hepatotoxic.

In some embodiments, a modified oligonucleotide introduced to a cell may exhibit reduced degradation in the cell, as compared to an unmodified polynucleotide, i.e. increased stability.

The oligonucleotides of the disclosure can include any useful modification, such as to the sugar, the nucleobase, or the internucleoside linkage (e.g. to a linking phosphate, to a phosphodiester linkage, to the phosphodiester backbone). For example, the major groove of a polynucleotide, or the major groove face of a nucleobase may comprise one or more modifications. One or more atoms of a pyrimidine nucleobase (e.g. on the major groove face) may be replaced or substituted with optionally substituted amino, optionally substituted thiol, optionally substituted alkyl (e.g., methyl or ethyl), or halo (e.g., chloro or fluoro). In certain embodiments, modifications (e.g., one or more modifications) are present in each of the sugar and the internucleoside or nucleotide linkage. Modifications according to the present invention may be modifications of ribonucleic acids (RNAs) to deoxyribonucleic acids (DNAs), e.g., the substitution of the 2'OH of the ribofuranosyl ring to 2'H, threose nucleic acids (TNAs), glycol nucleic acids (GNAs), peptide nucleic acids (PNAs), locked nucleic acids (LNAs) or hybrids thereof). Additional modifications are described herein.

In some embodiments, the at least one modification of the oligonucleotide of interest comprises a nucleobase analog or derivative (e.g., inosine or phosphorothioate nucleotides). Such oligonucleotides can be used, for example, to prepare nucleic acids that have altered base-pairing abilities or increased resistance to nucleases. When dsRNA is produced synthetically, less common bases, such as inosine, 5-methylcytosine, 6-methyladenine, hypoxanthine and others can also be used for antisense, dsRNA, and ribozyme pairing. For example, oligonucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of an RNA can also be made.

In some embodiments, the at least one modification of the oligonucleotide of interest is located on the sugar moiety of the nucleotide.

In some embodiments, the at least one modification of the oligonucleotide of interest is located on the phosphate backbone of the nucleic acid. In some embodiments, oligonucleotides of interest can include nucleotide sequences wherein at least one, or all, of the internucleotide bridging phosphate residues are modified phosphates, such as methyl phosphonates, methyl phosphonothioates, phosphoromorpholidates, phosphoropiperazidates and phosphoramidates. For example, every other one of the internucleotide bridging phosphate residues can be modified as described. In another non-limiting example, the oligonucleotide of interest is double stranded RNA is a nucleotide sequence in which one, or all, of the nucleotides contain a 2' lower alkyl moiety (e.g., $C_1$-$C_4$, linear or branched, saturated or unsaturated alkyl, such as methyl, ethyl, ethenyl, propyl, 1-propenyl, 2-propenyl, and isopropyl).

In some embodiments, the at least one modification of the oligonucleotide of interest comprises a locked nucleic acid (LNA). The term "locked nucleic acids" (LNA) includes nucleic acids which contain one or more LNA nucleotide monomers with a bicyclic furanose unit locked in an RNA mimicking sugar conformation, which enhances hybridization affinity for complementary sequences in ssRNA, ssDNA, or dsDNA (see Vester et al., 2004, Biochemistry 43(42): 13233-41, the contents of which are incorporated herein by reference).

In some embodiments, the at least one modification of the oligonucleotide of interest comprises a constrained ethyl nucleoside analog (CET), for example a 2'-4' cET analog. As used herein, a "constrained ethyl nucleotide" or "cEt" is a locked nucleic acid comprising a bicyclic sugar moiety comprising a 4'-CH(CH3)-O-2' bridge. In some embodiments, a constrained ethyl nucleotide is in an S conformation (an "S-constrained ethyl nucleotide" or "S-cEt"). In some embodiments, a constrained ethyl nucleotide is in an R conformation (an "R-constrained ethyl nucleotide" or "R-cEt").

In some embodiments, the at least one modification of the oligonucleotide of interest comprises a 2'-O-methoxy-ethyl (2'-MOE) modification. 2'-MOE bases are often used for antisense oligonucleotides (ASO), aptamers, and siRNA. Compared to standard RNA bases, 2'-MOE bases may offer increased resistance to nuclease degradation, reduced toxicity, and increased affinity for binding to complimentary RNA.

In some embodiments, the at least one modification of the oligonucleotide of interest comprises a 2'-O-Methyl (2'-O-Me) modification. 2'-O-Me RNA is a naturally occurring modification of RNA found in tRNA and other small RNAs that arises as a post-transcriptional modification. In some embodiments, oligonucleotides can be directly synthesized that contain 2'-O-Methyl RNA. This modification can increase the melting temperature or binding affinity (Tm) of RNA:RNA duplexes, but results in only small changes in RNA:DNA stability. It increases stability with respect to attack by single-stranded ribonucleases, and can be 5 to 10-fold less susceptible to DNases than DNA. In some embodiments, 2'O-Me is used in antisense oligonucleotides as a means to increase stability and binding affinity to the cognate mRNA.

In some embodiments, the at least one modification of the oligonucleotide of interest comprises a 2' Fluoro modification. 2' Fluoro bases have a fluorine modified ribose which increases binding affinity (Tm) and also confers increased nuclease resistance when compared to native RNA. These modifications can be employed in ribozymes and siRNAs to improve stability in serum or other biological fluids.

In some embodiments, the at least one modification of the oligonucleotide of interest comprises a 5-Bromo-deoxyuridine modification. 5-Bromo-deoxyuridine is a photoreactive halogenated base that can be incorporated into oligonucleotides to crosslink them to DNA, RNA or proteins with exposure to UV light. Crosslinking is maximally efficient with light at 308 nm.

In some embodiments, the at least one modification of the oligonucleotide of interest comprises a deoxyUridine modification. DeoxyUridine (dU) can be substituted for deoxy Thymine (dT) in DNA oligonucleotides. The base can be removed by the enzyme uracil-N-deglycosylase (UNG) which renders the oligo susceptible to strand scission. One common use of this strategy is to eliminate amplified DNA and prevent cross-contamination.

In some embodiments, the at least one modification of the oligonucleotide of interest comprises a 2,6-Diaminopurine (2-Amino-dA) modification. This modified base can form three hydrogen bonds when base-paired with dT, and can increase the melting temperature of short oligonucleotides by as much as 1-2° C. per insertion, depending on sequence context.

In some embodiments, the at least one modification of the oligonucleotide of interest comprises a Dideoxy-C modification. Dideoxycytidine (ddC) is a 3' chain terminator that prevents 3' extension by DNA polymerases.

In some embodiments, the at least one modification of the oligonucleotide of interest comprises a deoxyInosine (dI) modification. 2'-DeoxyInosine is a naturally occurring base that, while not truly universal, is less destabilizing than mismatches involving the four standard bases. Hydrogen bond interactions between dI and deoxy Adenosine (dA), deoxgyGuanosine (dG), deoxyCytidine (dC) and dT are weak and unequal, with the result that some base-pairing bias does exist with dI:dC>dI:dA>dI:dG>dI:dT. When present in a DNA template, deoxyInosine preferentially directs incorporation of dC in the growing nascent strand by DNA polymerase.

In some embodiments, the at least one modification of the oligonucleotide of interest comprises a Hydroxymethyl dC modification. Without wishing to be bound by theory, it is thought that Hydroxymethyl dC plays a role in epigenetic regulation.

In some embodiments, the at least one modification of the oligonucleotide of interest comprises an inverted dT. Inverted dT can be incorporated at the 3'-end of an oligo, leading to a 3'-3' linkage which inhibits both degradation by 3' exonucleases and extension by DNA polymerases.

In some embodiments, the at least one modification of the oligonucleotide of interest comprises a 5-Methyl deoxyCytidine (5-Methyl dC) modification. 5-Methyl deoxyCytidine when substituted for dC will increase the Tm by as much as 0.5° C. per insertion. In addition, the presence of 5-Methyl dC in CpG motifs can prevent or limit unwanted immune responses that otherwise occur if oligos are administered in vivo.

In some embodiments, the at least one modification of the oligonucleotide of interest comprises a 5-Nitroindole modification. 5-Nitroindole is a universal base. It does not favor any particular base-pairing (i.e., it does not support base-specific hydrogen bond formation), but does contribute to duplex stability through base-stacking interactions. Therefore, it is not as destabilizing to the duplex as mismatches between the standard bases. 5-Nitroindole directs random incorporation of any specific base when used as a template for DNA polymerase and partially blocks enzyme processivity.

In some embodiments, the at least one modification of the oligonucleotide of interest comprises a 5-hydroxybutynl-2'-deoxyuridine modification. 5-hydroxybutynl-2'-deoxyuridine is a duplex-stabilizing modified base that increases oligonucleotide melting temperature. Oligonucleotides containing 5-hydroxybutynl-2'-deoxyuridine can be extended normally by polymerases, including Taq polymerase, making 5-hydroxybutynl-2'-deoxyuridine a useful modified base for designing short primers or probes for low-complexity, A-T rich sequences.

In some embodiments, the at least one modification of the oligonucleotide of interest comprises an 8-aza-7-deazaguanosine modification. 8-aza-7-deazaguanosine is a modified base that eliminates naturally occurring, non-Watson-and-Crick secondary structures associated with guanine-rich sequences. Oligonucleotides containing 8-aza-7-deazaguanosine can be extended normally by polymerases, including Taq polymerase, making 8-aza-7-deazaguanosine a useful modified base for designing guanine-rich primers and probes. In addition, unlike standard guanine bases, 8-aza-7-deazaguanosine does not quench fluorophores, potentially improving probe performance.

In some embodiments, the at least one modification of the oligonucleotide of interest comprises a 2-Aminopurine modification. 2-Aminopurine can substitute for dA in an oligonucleotide. It is a naturally fluorescent base that is sensitive to the local environment making it a useful probe for monitoring the structure and dynamics of DNA hairpins and for detecting the base stacking state of a duplex.

In some embodiments, the at least one modification of the oligonucleotide of interest comprises a phosphorothioate linkage (PS). The phosphorothioate (PS) bond substitutes a sulfur atom for a non-bridging oxygen in the phosphate backbone of an oligonucleotide. This modification renders the internucleotide linkage resistant to nuclease degradation. In some embodiments, phosphorothioate bonds can be introduced between the last 3-5 nucleotides at the 5'- or 3'-end, or both, of the oligonucleotide to inhibit exonuclease degradation. Alternatively, including phosphorothioate bonds throughout the entire oligo can also reduce attack by endonucleases. PS linkages can be included in DNA or RNA oligonucleotides, and can be combined with other modifications such as LNA or 2'-O-methyl modifications.

In some embodiments, the at least one modification of the oligonucleotide of interest comprises a phosphate, such as a 5' or 3' terminal phosphate (sometimes referred to as a phosphorylated oligonucleotide). 5' Phosphorylation is needed if an oligo is used as a substrate for DNA ligase. 3' Phosphorylation will inhibit degradation by some 3'-exonucleases and can be used to block extension by DNA polymerases.

In some embodiments, the at least one modification of the oligonucleotide of interest comprises polyethylene glycol (PEG). Without wishing to be bound by theory, it is thought that attachment of short PEG chains to oligonucleotides can affect their gene silencing ability.

Any therapeutic oligonucleotide comprising one or modifications is envisaged as within the scope of the instant disclosure. As a representative but non-limiting example of therapeutic oligonucleotides, a summary of chemical modifications in FDA approved oligonucleotide-based drugs is shown in Table 1 below.

TABLE 1

Overview of Chemical Modifications of FDA Approved Oligonucleotide Drugs

| Drug | Type | Modification | Pharma |
| --- | --- | --- | --- |
| Vitravene | ASO | Phosphorothioated | Ionis Pharmaceuticals |
| Macugen | Aptamer | PEGylation, 2'-F, 2'-OMe | Valeant Pharmaceuticals |
| Kynamro | ASO | Phosphorothioated, 2'-MOE | Kastle Therapeutics |
| Exondys 51 | ASO | Morpholino nucleic acid | Sarepta Therapeutics |
| Spinraza | ASO | Phosphorothioated, 2'-MOE | Biogen |
| Heplisav-B | CpG oligo | Phosphorothioated | Dynavax Technologies |
| Tegsedi | ASO | Phosphorothioated, 2'-MOE | Akcea Therapeutics |
| Onpattro | siRNA | 2'-MOE | Alnylam Pharmaceuticals |

Table 2 provides an expanded library of codes for modified nucleobases incorporated into the modified oligonucleotides described herein.

TABLE 2

Expanded library of codes for modified nucleotides

| Deoxynucleoside monophosphate | Codes | Molecular formula |
| --- | --- | --- |
| *C | C | C9 H12 O5 N3 P S |
| *T | T | C10 H13 O6 N2 P S |
| *A | A | C10 H12 O4 N5 P S |
| *G | G | C10 H12 O5 N5 P S |
| *C(5me) + MOErC | B | C13 H20 O7 N3 P S |
| *T + MOErT | D | C13 H19 O8 N2 P S |
| *A + MOErA | E | C13 H18 O6 N5 P S |
| *G + MOErG | F | C13 H18 O7 N5 P S |
| *C(5me) | H | C10 H14 O5 N3 P S |
| *C + LNA | I | C12 H17 O6 N3 P S |
| *T + LNA | J | C12 H15 O7 N2 P S |
| *A + LNA | K | C12 H15 O5 N5 P S |
| *G + LNA | L | C12 H15 O6 N5 P S |
| *C + cEt | M | C13 H19 O6 N3 P S |
| *T + cEt | N | C13 H17 O7 N2 P S |
| *A + cEt | O | C13 H17 O5 N5 P S |
| *G + cEt | P | C13 H17 O6 N5 P S |

5me: 5-methyl
MOEr: 2'-O-methoxy-ethyl
LNA: Locked Nucleic Acid
cEt: constrained ethyl nucleoside analog
(*): modified phosphorothioate linkage Synthesizing Oligonucleotides The disclosure provides methods of making oligonucleotides of interest, and compositions comprising said oligonucleotides of interest, comprising (a) synthesizing the oligonucleotide of interest; and (b) characterizing the oligonucleotide of interest using the liquid chromatography and mass spectrometry methods of the disclosure. In some embodiments, the methods comprise selecting oligonucleotides of interest with particular characteristics, such as purity, determined by the methods described herein.

In some embodiments of the oligonucleotides of interest and compositions comprising oligonucleotides of interest of the disclosure, the composition comprising the oligonucleotides of interest is sufficiently pure for further downstream applications, such as administration to a subject for the treatment of a disease or disorder. Sufficient purity can be achieved, for example, by synthesizing oligonucleotides of interest using any suitable method known in the art to produce a composition comprising oligonucleotides of interest, assaying the percentage of the total oligonucleotides in the composition that are the oligonucleotides of interest, and either discarding or further purifying the composition if the composition is not sufficiently pure. In some embodiments, the oligonucleotides of interest comprise at least one modification as described herein.

Impurities in compositions comprising oligonucleotides of interest that can be characterized using the methods described herein include, but are not limited to, fragments of the oligonucleotides of interest and incorrect synthesis products. For example, the abundance of degradation products or truncated products produced by oligonucleotide synthesis can be detected using the methods described herein. Further, the methods described herein can be used to determine the presence and/or abundance of oligonucleotides with one or sequence mismatches, insertions or deletions relative to the sequence of the desired synthesis product, and oligonucleotides with modifications that differ from the desired modifications.

Without wishing to be bound by theory, liquid chromatography separates types of oligonucleotides in the sample by type, as can be seen by UV visualization of an electropherogram (see FIGS. 2A-2B for an example), and the peaks correspond to the oligonucleotides of interest and different types of oligonucleotide impurities in the sample, such as truncation or degradation products of the oligonucleotides of interest, or other oligonucleotides produced by the synthesis process. Intact mass analysis of the liquid chromatography peak corresponding to the oligonucleotides of interest and one or more peaks corresponding to impurities will allow the ordinarily skilled artisan determine the abundance of types of oligonucleotides corresponding to these peaks, such as the oligonucleotides of interest, in the sample. For further resolution and characterization of differences in sequence, mass and modification of oligonucleotides not readily apparent from intact mass analysis, the types of oligonucleotides in the sample determined from liquid chromatography can be fragmented using methods such as HCD, and analyzed via tandem mass spectrometry to determine structural characteristics, including sequence and modification.

Accordingly the disclosure provides methods of making a composition comprising oligonucleotides of interest where at least 90%, at least 95%, at least 96%, at least 97%, at least 98%, at least 98.5%, at least 99%, at least 99.5%, at least 99.6%, at least 99.7%, at least 99.8% or at least 99.9% of the oligonucleotides in the composition are the oligonucleotide of interest. In some embodiments, at least 98% of the oligonucleotides in the composition are the oligonucleotides of interest. In some embodiments, at least 99% of the oligonucleotides in the composition are the oligonucleotides of interest. In some embodiments, at least 98.5% of the oligonucleotides in the composition are the oligonucleotides of interest. In some embodiments, at least 99.9% of the oligonucleotides in the composition are the oligonucleotides of interest. Percentages of types of oligonucleotides in the composition can be described as percentage by mass. Alternatively, percentages of types of oligonucleotides in the composition can be determined by numbers of molecules.

In some embodiments, the method of making a composition comprising oligonucleotides of interest further comprises adding a pharmaceutically acceptable carrier, diluent or excipient.

All suitable methods of synthesizing oligonucleotides of the disclosure are envisaged as within the scope of the instant disclosure. These methods include, but are not limited to, solid phase synthesis, chemical synthesis and enzymatic reactions.

In some embodiments, the synthesis comprises solid phase synthesis. Solid phase oligonucleotide synthesis methods, such as the phosphoramidite method, typically synthesize oligonucleotides in the 3' to 5' direction attached to a solid surface through a cycle of chemical reactions that sequentially add nucleotides to the growing oligonucleotide. For example, for DNA, a 3' nucleoside with a 5' DMT (4,4' dimethoxytrityl) protecting group is attached to the solid support and is detritylated. Following detritylation, the support bound nucleoside is reacted with the next base to form a nucleoside phosphoramidite monomer, which is mixed with an activator (tetrazole or a derivative). The diisopropylamino group of the nucleoside phosphoramidite is protonated by the activator, and is thereby converted to a good leaving group. This leaving groups is displaced by the 5'-hydroxyl group of the support-bound nucleoside on its neighbouring phosphorus atom, and a new phosphorus-oxygen bond is formed, creating a support-bound phosphite triester. Next the nucleoside is capped to block the unreacted 5' hydroxyl groups using acetic anhydride and N-methylimidazole (NMI) to acetylate the 5' hydroxyl groups. The phosphite-triester is converted to a stable (P(V)) species by iodine oxidation in the presence of water and pyridine by iodine oxidation in the presence of water and pyridine, and the cycle is repeated.

RNA can also be synthesized using standard solid phase oligonucleotide synthesis protocols. See, for example US20070123482A1 and US20070213292A1, the contents of which are hereby incorporated by reference in their entirety.

Modifications to oligonucleotides of interest can be incorporated during synthesis, or added after synthesis, depending on the modification. For example, phosphorothioate derivatives of nucleotides can be incorporated during synthesis to produce phosphorothioate linkages, while terminal phosphates can be added to a synthesized oligonucleotide through an enzymatic reaction (phosphorylation) after synthesis of the oligonucleotide.

Liquid Chromatography

The disclosure provides methods for characterizing a composition comprising oligonucleotides of interest, the methods comprising liquid chromatography. Liquid chromatography can be used alone or in combination with other methods to separate analytes (e.g., oligonucleotides that differ in sequence and/or modification) in a sample. For example, when a sample comprises oligonucleotides of interest, and one or more impurities, the liquid chromatography may be used to separate the oligonucleotides of interest from the impurities. Representative impurities detected using these methods include degradation products of the oligonucleotides of interest, and byproducts from synthesizing the oligonucleotides of interest. Liquid chromatography separation can be combined with detection, such as ultraviolet detection or mass spectrometry, thereby providing an assay system for characterizing oligonucleotide of interest in a composition.

In some embodiments, types of oligonucleotides in a sample, including inter alia, oligonucleotides of interest and one or more impurities as described herein, are separated using liquid chromatography.

As used herein, the term "chromatography" refers to a process in which a chemical mixture comprising a liquid or gas is separated into components as a result of differential distribution of the chemical entities as they flow around, over, and/or through a stationary liquid or solid phase. "Liquid chromatography" or "LC" refers to a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Liquid chromatography includes, but is not limited to, normal phase liquid chromatography (NPLC), hydrophilic interaction liquid chromatography (HILIC), reversed phase liquid chromatography (RPLC), including ion-pairing reversed phase liquid chromatography (IP-RPLC), high performance liquid chromatography (HPLC), high turbulence liquid chromatography (HTLC) and ultra performance liquid chromatography (UPLC).

"Retention time" refers to length of time for which a particular analyte, such as an oligonucleotide, is retained by a liquid chromatography substrate prior to elution.

"High performance liquid chromatography" or "HPLC" refers to liquid chromatography in which the degree of separation is increased by forcing the mobile phase under pressure through a stationary phase, typically a densely packed column.

"Ultra performance liquid chromatography" or "UPLC" refers to liquid chromatography methods with enhanced speed, sensitivity and resolution as compared to HPLC. Generally, UPLC is applicable for particles of less than 2 μm in diameter. Separation and quantification in UPLC is done under extremely high pressure (up to 100 MPa).

Gas chromatography (GC) refers to a separation technique that uses gas flow through a column, such as a glass or metal column, to separate compounds based on volatility and interaction with a liquid stationary phase. The mobile phase, a carrier gas, is usually an inert gas such as helium or an unreactive gas such as nitrogen.

One of skill in the art may select HPLC instruments and columns that are suitable for use in the methods. The chromatographic column typically includes a medium (i.e., a packing material) to facilitate separation of chemical moieties (i.e., fractionation). The medium may include minute particle, which include a bonded surface that interacts with the various chemical moieties to facilitate separation of the chemical moieties.

In certain embodiments, an analyte, for example the oligonucleotides of interest, may be purified by applying a sample to a column under conditions where the analyte is reversibly retained by the column packing material, while one or more other materials are not retained. In these embodiments, a first mobile phase condition can be employed where the analyte is retained by the column and a second mobile phase condition can subsequently be employed to remove retained material from the column, once the non-retained materials are washed through. Alternatively, an analyte may be purified by applying a sample to a column under mobile phase conditions where the analyte elutes at a differential rate in comparison to one or more other materials. Such procedures may enrich the amount of one or more analytes of interest relative to one or more other components of the sample.

In some embodiments, the sample to be analyzed is applied to the column at the inlet port, eluted with a solvent or solvent mixture, and discharged at the outlet port. Different solvent modes may be selected for eluting the analytes, such as the oligonucleotides of interest or impurities in the sample. For example, liquid chromatography may be performed using a gradient mode, an isocratic mode, or a polytypic (i.e. mixed) mode. In some embodiments, HPLC is performed on an analytical HPLC system with a C18 solid phase using a first mobile phase of 50 mM HFIP and 5 mM DIEA in water, and a second mobile phase of 50 mM HFIP and 5 mM DIEA in acetonitrile. In some embodiments, the first mobile phase comprises 40-60 mM HFIP and 3-15 mM DIEA in water, and the second mobile phase comprises 40-60 mM HFIP and 3-15 mM DIEA in acetonitrile. In some embodiments, HPLC is performed on an analytical HPLC system with a cross-linked diol solid phase with a first mobile phase of 15 mM buffer in 70% acetonitrile, and a second mobile phase of 15 mM buffer in 30% acetonitrile. In some embodiments, first mobile phase comprises 3-25 mM buffer in 70% acetonitrile, and the second mobile phase comprises 3-25 mM buffer in 20-40% acetonitrile. In some embodiments, the buffer is selected from the group consisting of ammonium acetate and ammonium formate. In some embodiments, the buffer is ammonium acetate.

Numerous column packings are available for chromatographic separation of samples and selection of an appropriate separation protocol is an empirical process that depends on the sample characteristics, analytes of interest, presence of interfering substances and their characteristics, etc. Commercially available HPLC columns include, but are not limited to, polar, ion exchange (both cation and anion), hydrophobic interaction, phenyl, C-2, C-8, C-18, and polar coating on porous polymer columns.

In some embodiments, the liquid chromatography comprises hydrophilic interaction liquid chromatography (HILIC). HILIC can be used to separate small polar compounds on polar stationary phases. HILIC uses hydrophilic stationary phases with reversed-phase type eluents, and elutes analytes in order of increasing polarity. Suitable mobile phases for HILIC include acetonitrile (ACN), however any aprotic solvent miscible with water can be used. Ionic additives, such as ammonium acetate and ammonium formate, can be used to modulate mobile phase pH and ion strength.

In some embodiments, the column dimensions are 1-3 mm inner diameter (ID)×50-300 mm length. In some embodiments, the liquid chromatography comprises HILIC. In some embodiments, the column has a cross-linked diol solid phase with a mean particle size of 3 μm (nominal), and a median particle pore size of 200 Å. In some embodiments, the column dimensions are 2 mm inner diameter (ID)×100 mm length. In some embodiments, the column dimensions are 2 mm ID×150 mm length. In some embodiments, the column is a Phenomenex Luna® 3 μm HILIC 200 Å, LC Column 150×2 mm or equivalent (see, e.g., Phenomenex Cat. No. 00D-4449-B0 or equivalent).

In some embodiments, the HILIC comprises a mobile phase comprising a buffer comprising ammonium acetate. In some embodiments, the mobile phase comprises a first buffer comprising 3-25 mM ammonium acetate in 50-80% acetonitrile (ACN) and a second buffer comprising 3-25 mM ammonium acetate in 20-40% (ACN). In some embodiments, the mobile phase comprises a first buffer comprising 15 mM ammonium acetate in 70% acetonitrile (ACN) and a second buffer comprising 15 mM ammonium acetate in 30% (ACN). In some embodiments, the HILIC comprises a mobile phase comprising a buffer comprising ammonium formate. In some embodiments, the mobile phase comprises a first buffer comprising 3-25 mM ammonium formate in 50-80% acetonitrile (ACN) and a second buffer comprising 3-25 mM ammonium formate in 20-40% (ACN). In some embodiments, the mobile phase comprises a first buffer comprising 15 mM ammonium formate in 70% acetonitrile (ACN) and a second buffer comprising 15 mM ammonium formate in 30% (ACN).

In some embodiments, the liquid chromatography comprises ion-pairing reversed-phase liquid chromatography (IP-RPLC). IP-RPLC is a technique for separation of organic ions an partly ionized organic analytes. IP-RPLC uses the same types of stationary and mobile phases as RPLC, with the addition of an ion pair reagent to the mobile phase. The ion pair reagent can be, for example, alkylsulfonate, an alkylsulfate or an alkylammonium salt, and it can change the retention time of ionic analytes. IP-RPLC can be used to separate classes of biomolecules, including amino acids, peptides and nucleic acids.

In some embodiments, the HPLC column has a C18 solid phase with a median particle size of 1.3-2.0 µm (nominal) and a median particle pore size of 100-200 Å. In some embodiments, the HPLC column has a C18 solid phase with a median particle size of 1.7 µm (nominal) and a median particle pore size of 130 Å. In some embodiments, the column dimensions are 2.1 mm ID×100 mm length. (Waters ACQUITY UPLC Oligonucleotide BEH C18 Column, 130 Å, 1.7 µm, 2.1 mm×100 mm, Waters Cat. No. 186003950 or equivalent).

In some embodiments, the liquid chromatography comprises ion-pairing reversed-phase liquid chromatography (IP-RPLC). In some embodiments, the IP-RPLC comprises mobile phase comprising buffer comprising Hexafluoroisopropanol (HFIP) and 5 mM N,N-Diisopropylethylamine (DIEA). In some embodiments, the mobile phase comprises a first buffer comprising 40-60 mM HFIP and 3-15 mM DIEA in water and a second buffer comprising 40-60 mM HFIP and 3-15 mM DIEA in acetonitrile. In some embodiments, the mobile phase comprises a first buffer comprising 50 mM HFIP and 5 mM DIEA in water and a second buffer comprising 50 mM HFIP and 5 mM DIEA in acetonitrile.

In some embodiments, the IP-RPLC comprises an HPLC column that has a C18 solid phase with a median particle size of 1.3-2.0 µm (nominal) and a median particle pore size of 100-200 Å. In some embodiments, the IP-RPLC comprises an HPLC column that has a C18 solid phase with a median particle size of 1.7 µm (nominal) and a median particle pore size of 130 Å. In some embodiments, the column dimensions are 2.1 mm ID×100 mm length (see, for example, Waters ACQUITY UPLC Oligonucleotide BEH C18 Column, 130 Å, 1.7 µm, 2.1 mm×100 mm, Waters Cat. No. 186003950 or equivalent). In some embodiments, the IP-RPLC comprises a 1.7 µm, Oligo-XT 100 Å, 50×2.1 mm column.

In some embodiments, liquid chromatographic separation, e.g. via HILIC or IP-LPRC, may be carried out at a specific temperature. This temperature can be, for example, between 15° C. and 75° C. In some embodiments, the separation is carried out at between 20° C. and 50° C. In a preferred embodiment, the separation is carried out at about 23° C., about 30° C., about 40° C., or about 50° C. In some embodiments, HILIC separation comprises a column temperature of between 23 and 50° C. In some embodiments, HILIC separation comprises a column temperature of 30° C.

Liquid Chromatography UV-Visible Spectroscopy

The disclosure provides methods of detecting analytes in a sample, for example oligonucleotides of interest and one or more impurities, that have been separated via liquid chromatography.

In some embodiments, the analytes separated by the liquid chromatography methods described herein are detected using ultraviolet and/or visible light. In some embodiments, the detection system is Ultraviolet-visible spectroscopy (UV-Vis). UV-Vis probes the electronic transitions of molecules as they absorb light in the UV and visible regions of the electromagnetic spectrum. Any species with an extended system of alternating double and single bonds will absorb UV light, and anything with color absorbs visible light, making UV-vis spectroscopy applicable to a wide range of samples. With regard to instrumentation, the light source is usually a hydrogen or deuterium lamp for UV measurements and a tungsten lamp for visible measurements. The wavelengths of these continuous light sources are selected with a wavelength separator, such as a prism or grating monochromator. Spectra are obtained by scanning the wavelength separator and quantitative measurements can be made from a spectrum or at a single wavelength. A variety of UV-vis spectroscopy methods exist. These methods include, but are not limited to, molecular Ultraviolet/Visible, Absorption Spectroscopy, Ultraviolet spectroscopy, Ultraviolet/Visible Absorption Spectroscopy. Any suitable UV-vis detection system is envisaged as within the scope of the instant disclosure.

Mass Spectrometry

The disclosure provides methods of detecting analytes in a sample, for example oligonucleotides of interest and one or more impurities such as truncated oligonucleotides, that have been separated via liquid chromatography. These methods include mass spectrometry. Mass spectrometry, and tandem mass spectrometry (MS/MS) can be used to annotate and successful identify sequences and modifications of oligonucleotides used for therapeutic applications.

In some embodiments, the detection system is Mass Spectrometry (MS). Liquid chromatography-mass spectrometry (LC-MS) is an analytical chemistry technique that combines the physical separation capabilities of liquid chromatography (for example, high performance liquid chromatography, or HPLC) with the mass analysis capabilities of mass spectrometry (MS). Liquid chromatography separates mixtures with multiple components (analytes), while mass spectrometry provides structural identity and levels of the individual components with high molecular specificity and detection sensitivity.

Liquid chromatography and mass spectrometry are described in EP3143392, the contents of which are incorporated herein by reference.

Mass spectrometry is performed using a mass spectrometer, which includes an ion source for ionizing a sample and creating charged molecules for further analysis. In various embodiments, compositions comprising oligonucleotides of interest and components thereof such additional synthesis or degradation products may be ionized by any method known to the skilled artisan. Ionization sources used in various MS techniques include, but are not limited to, electron ionization, chemical ionization, electrospray ionization (ESI), photon ionization, atmospheric pressure chemical ionization (APCT), photoionization, atmospheric pressure photoionization (APPI), fast atom bombardment (FAB)/liquid secondary ionization (LSIMS), matrix assisted laser desorption ionization (MALDI), field ionization, field desorption, thermospray/plasmaspray ionization, surface enhanced laser desorption ionization (SELDI), inductively coupled plasma (ICP), particle beam ionization and ion-mobility separation (IMS). The skilled artisan will understand that the choice of ionization method may be determined based on the analyte to be measured, type of sample, the type of detector, the choice of positive versus negative mode, etc.

As used herein, the term "mass spectrometry" or "MS" refers to an analytical technique to identify compounds by their mass. MS refers to methods of filtering, detecting, and measuring ions based on their mass to charge ratio (m/z). MS technology generally includes ionizing the compounds to form charged species (e.g., ions) and detecting the exact mass of the ions divided by their charge, known as m/z. The compounds may be ionized and detected by any suitable means.

A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. Nos. 6,204,500; 6,107,623; 6,268,144; and 6,124,137.

MS can generate and detect both positive and negative ions. As used herein, the term "ionization" or "ionizing" refers to the process of generating an analyte ion having a net electrical charge equal to one or more electron units. Positive ions are those having a net positive charge of one or more electron units. Negative ions are those having a net negative charge of one or more electron units. In "electron ionization" or "EI" methods, analytes in a gaseous or vapor phase interact with a flow of electrons. Impact of the electrons with the analyte produces analyte ions, which may then be subjected to mass spectrometry techniques. EI can be combined with gas chromatography (GC) or liquid chromatography methods. In "chemical ionization" or "CI," a reagent gas (e.g. ammonia) is subjected to electron impact, and analyte ions are formed by the interaction of reagent gas ions and analyte molecules. In "fast atom bombardment" or "FAB," a beam of high energy atoms (often Xe or Ar) impacts a non-volatile sample, desorbing and ionizing molecules contained in the sample. In some embodiments, test samples are dissolved in a viscous liquid matrix such as glycerol, thioglycerol, m-nitrobenzyJ alcohol, 18-crown-6 crown ether, 2-nitropheiiyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules. MALDI-TOF refers to Matrix-Assisted Laser Desorption/Ionization-Time Of Flight (MALDI-TOF) mass spectrometry (MS). MALDI-TOF is useful for compounds up to about 15,000 daltons.

"Surface enhanced laser desorption ionization" or "SELDI" refers to another method in which a non-volatile sample is exposed to laser irradiation, which desorbs and ionizes analytes in the sample by various ionization pathways, including photoionization, protonation, deprotonation, and cluster decay. For SELDI, the sample is typically bound to a surface that preferentially retains one or more analytes of interest. As in MALDI, this process may also employ an energy-absorbing material to facilitate ionization.

In some embodiments, the mass spectrometry comprises electrospray ionization (ESI). In some embodiments, the ESI comprises nano-flow ESI. Nano-flow ESI refers to flow rates that can be in the nanoliter/min range (as opposed to high microliter/min to low milliliter/min range for regular HPLC). It can be used for sensitive detection of minute sample concentrations.

"Electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

"Atmospheric pressure chemical ionization" or "APCI," refers to mass spectroscopy methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated N2 gas may be used to improve removal of solvent. The gas-phase ionization in APCI can be more effective than ESI for analyzing less-polar species.

The term "Atmospheric Pressure Photoionization" or "APPI" as used herein refers to the form of mass spectroscopy where the mechanism for the photoionization of molecule M is photon absorption and electron ejection to form the molecular M+. Because the photon energy typically is just above the ionization potential, the molecular ion is less susceptible to dissociation.

As used herein, the term "inductively coupled plasma' or "ICP" refers to methods in which a sample is interacted with a partially ionized gas at a sufficiently high temperature to atomize and ionize most elements.

As used herein, "ion-mobility spectrometry," sometimes also referred to as "ion-mobility separation" or "IMS" refers to an analytical chemistry method that separates gas phase ions based on their interaction with a collision gas and their masses. In the first step, the ions are separated according to their mobility through a buffer gas on a millisecond timescale using an ion mobility spectrometer. The separated ions are then introduced into a mass analyzer in a second step where their mass to charge ratios can be determined on a microsecond timescale.

As used, herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase.

After the oligonucleotide composition or components thereof have been ionized, the charged ions thereby created may be analyzed to determine m/z. Suitable analyzers for determining m/z include quadrupole analyzers, ion trap analyzers, time-of-flight analyzers, Fourier-transform ion cyclotron resonance (FTICR) analyzers and Orbitrap spectrometers. The ions may be detected using one of several detection modes. For example, only selected ions may be detected using a selective ion monitoring mode (SIM), or alternatively, multiple ions may be detected using a scanning mode, e.g., multiple reaction monitoring (MRM) or selected reaction monitoring (SRM).

In some embodiments, m/z is determined using a quadrupole analyzer (instrument). In a "quadrupole" or "quadrupole ion trap" instrument, ions in an oscillating radio frequency field experience a force proportional to the DC potential applied between electrodes, the amplitude of the RF signal, and m/z. The voltage and amplitude may be selected so that only ions having a particular m/z travel the length of the quadrupole, while all other ions are deflected. Thus, quadrupole instruments may act as both a "mass filter" and as a "mass detector" for the ions injected into the instrument. In Time-of-Flight (ToF), the ions are accelerated in a homogenous electrostatic field using ground and repeller electrodes. The kinetic energy is held constant, and the ion travel down the field-free ToF tube. Because kinetic energy is constant ($KE=\frac{1}{2}MV^2$) those with smaller m/z will have a greater speed compared to larger m/z. "Quadrupole time-of-flight" or "QTof" mass spectrometry refers to a type of mass spectrometry using mass spectrometers that pair a quadrupole that functions as a collision cell with a time-of-flight analyzer. This allows for high-resolution, high mass accuracy analysis of all ions simultaneously. In an exemplary QTof system, a sample is delivered by an online liquid chromatography system and ionized. The particle beam then travels through an ion guide and into the quadrupole, before passing to a ToF analyzer.

In some embodiments, the MS technique can employ "tandem mass spectrometry," or "MS/MS." In this technique, a precursor ion (also called a parent ion) generated from a molecule of interest can be filtered in an MS instrument, and the precursor ion subsequently fragmented to yield one or more fragment ions (also called daughter ions or product ions) that are then analyzed in a second MS procedure. By careful selection of precursor ions, only ions produced by certain analytes are passed to the fragmentation chamber, where collision with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples.

In some embodiments, fragmentation is achieved using a high-energy collision-induced dissociation (HCD) method, in which the precursor ions are accelerated to high velocities into a gas-filled collision cell. HCD is described in U.S. Pat. No. 8,148,677, the contents of which are incorporated herein by reference.

In general, as collision energy is increased from a low value, a threshold or onset collision energy will be observed at which the number of observed fragment ions rapidly increases from an initial value of nil. This yield of fragment ions is further observed to increase, with increasing collision energy, up to some maximum value. Further increase in collision energy beyond that corresponding to the maximum corresponds to diminishing fragment yield, which decreases back to essentially zero yield at some energy. The "normalized collision energy" (NCE) is an expression of the collision energy compared to the optimum collision energy for a given m/z ratio. NCE is described in U.S. Pat. No. 8,278,620, the contents of which are incorporated herein by reference.

As used herein "maximal HCD" refers to the HCD energy at which the maximum number of fragments are produced. HCD energies can be calculated as percentages of the maximal HCD (NCE), e.g. 5%, 10%, 15%, 20%, 25%, 30%, 35%, 40%, 45% HCD and the like.

In some embodiments, tandem mass spectrometry may involve fragmentation using HCD. In some embodiments, HCD is achieved using a specific NCE, for example between 0% and 75%. In some embodiments, the NCE is between 10% and 50%, for example between 10% and 25%, or between 15% and 20%. In some embodiments, the NCE is 20%.

In some embodiments, the HPLC-MS/MS system can be controlled by data dependent acquisition (DDA). In tandem mass spectrometry, data-independent acquisition (DIA) is a method of molecular structure determination in which all ions within a selected m/z range are fragmented and analyzed in the second stage. Tandem mass spectra are acquired either by fragmenting all ions that enter the mass spectrometer at a given time (called broadband DIA) or by sequentially isolating and fragmenting ranges of m/z. Alternatively, in data-dependent acquisition (DDA), a fixed number of precursor ions are selected and analyzed by tandem mass spectrometry. DDA can select ions for MS/MS acquisition in real time, as components elute from a chromatographic system. Embedded algorithms can rapidly interrogate MS survey spectra and co-eluting precursor ions can be selected for MS/MS analysis based on threshold intensity, charge state, pre-defined exact mass include/exclude lists, or combinations thereof. The collision energy for each spectrum can be optimized according to precursor charge state and m/z.

The mass spectrometer typically provides the user with an ion scan or mass spectrum; that is, the relative abundance of each ion with a particular m/z over a given range (e.g., 400 to 1600 m/z). The mass spectrum may be related to the amount of the analyte, e.g. a component of an oligonucleotide composition, in the sample by numerous methods known in the art. For example, given that sampling and analysis parameters are carefully controlled, the relative abundance, sometimes referred to as relative intensity, of a given ion may be compared to a table that converts that relative abundance to an absolute amount of the original molecule. Alternatively, molecular standards may be run with the samples and a standard curve constructed based on ion signal generated from those standards. Methods of generating and using such standard curves are well known in the art and one of ordinary skill is capable of selecting an appropriate internal standard. Numerous other methods for relating the amount of an ion to the amount of the original molecule will be well known to those of ordinary skill in the art.

As ions collide with the detector, they produce a pulse of electrons that are converted to a digital signal. The acquired data is relayed to a computer, which plots ion counts per unit time. The areas under the peaks corresponding to particular ions, or the amplitude of such peaks, are measured and the area or amplitude is correlated to the amount of the component of interest, or marker, in the oligonucleotide composition. In certain embodiments, the area under the curves, or amplitude of the peaks, for fragment ion(s) and/or precursor ions are measured to determine the amount of analytes with a given m/z. As described above, the relative abundance, sometimes referred to as relative intensity, or the response of a given ion may be converted into an absolute amount of the original analyte using calibration standard curves based on peaks of one or more ions of an internal molecular standard. The absolute amount of an oligonucleotide composition component detected by LC-MS can then be converted into an absolute amount of the component that was present in the original sample.

Methods for determining the relative abundance of analytes in a sample such as oligonucleotides of interest include, but are not limited to, intact mass analysis. Intact mass analysis is the assessment of an analyte's total molecular weight by mass spectrometry (MS) without prior digestion or fragmentation of the analyte. The intensity of each peak as determined by liquid chromatography gives an indication of the relative abundance the corresponding analyte. Methods of carrying out intact mass analysis will be known in the art, and include Protein Metrics Intact Mass™ software.

In some embodiments, the m/z (mass divided by charge) spectrum may be deconvoluted to a neutral mass (i.e. mass of species without any charge) spectrum. Deconvolution methods transform an m/z spectrum to a neutral mass spectrum by deducing the charges of the ions in the m/z spectrum, and then multiplying m/z values by the appropriate values of z (charge) and subtracting the masses of the charge carriers (typically protons) to determine neutral mass. Charge is deduced by relationships among peaks in the m/z spectrum. Deconvolution of m/z spectra is described in U.S. Pat. No. 10,319,573, the contents of which are incorporated herein by reference.

Suitable LC-MS instruments and systems will be known to persons of skill in the art.

Pharmaceutical Compositions

The disclosure provides compositions comprising oligonucleotides of interest that have been characterized using the methods described herein. In some embodiments, the composition is a pharmaceutical composition.

In some embodiments of pharmaceutical compositions comprising oligonucleotides of interest, the composition is suitable for further administration to a subject for the treatment of a disease or disorder. In some embodiments, the subject is human. In some embodiments of the pharmaceutical compositions, the oligonucleotides of interest comprise at least one modification as described herein.

Accordingly the disclosure provides pharmaceutical compositions comprising oligonucleotides of interest where at least 80%, at least 85%, at least 90%, at least 95%, at least 96%, at least 97%, at least 98%, at least 98.5%, at least 99%, at least 99.5%, at least 99.6%, at least 99.7%, at least 99.8% or at least 99.9% of the oligonucleotides in the composition are the oligonucleotide of interest. In some embodiments, at least 95% of the oligonucleotides in the pharmaceutical composition are the oligonucleotides of interest. In some embodiments, at least 98% of the oligonucleotides in the pharmaceutical composition are the oligonucleotides of interest. In some embodiments, at least 99% of the oligonucleotides in the pharmaceutical composition are the oligonucleotides of interest. In some embodiments, at least 99.5% of the oligonucleotides in the pharmaceutical composition are the oligonucleotides of interest. In some embodiments, at least 99.9% of the oligonucleotides in the pharmaceutical composition are the oligonucleotides of interest. Percentages of types of oligonucleotides in the composition can be described as percentage by mass. Alternatively, or in addition, percentages of types of oligonucleotides in the composition can be determined by numbers of molecules.

In some embodiments, the method of making a composition comprising oligonucleotides of interest further comprises adding a pharmaceutically acceptable carrier, diluent or excipient.

By "pharmaceutically acceptable" it is meant a material that is not biologically or otherwise undesirable, i.e., the material can be administered to a subject without causing any undesirable biological effects such as toxicity.

Pharmaceutical compositions of the disclosure can optionally comprise additional medicinal agents, pharmaceutical agents, carriers, adjuvants, dispersing agents, and the like.

Compositions comprising oligonucleotides of interest can be formulated for administration in a pharmaceutical carrier in accordance with known techniques. See, e.g., Remington, *The Science And Practice of Pharmacy* ($9^{th}$ Ed. 1995) In the manufacture of a pharmaceutical composition according to the disclosure, the oligonucleotide of interest (including the physiologically acceptable salts thereof) is typically admixed with, inter alia, an acceptable carrier. The carrier can be a solid or a liquid, or both, and can be formulated with the oligonucleotide of interest as a unit-dose formulation, for example, a tablet, which can contain from 0.01 or 0.5% to 95% or 99% by weight of the oligonucleotide of interest. One or more oligonucleotides of interest can be incorporated in the formulations of the invention, which can be prepared by any of the well-known techniques of pharmacy.

Non-limiting examples of pharmaceutical compositions of the disclosure include those suitable for oral, rectal, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intracranial, intrathecal, and inhalation administration, administration to the liver by intraportal delivery, as well as direct organ injection (e.g., into the liver, into a limb, into the brain or spinal cord for delivery to the central nervous system, into the pancreas, or into a tumor or the tissue surrounding a tumor). The most suitable route in any given case will depend on the nature and severity of the condition being treated and on the nature of the particular pharmaceutical composition which is being used. In some embodiments, it may be desirable to deliver the composition locally to avoid any side effects associated with systemic administration. For example, local administration can be accomplished by direct injection at the desired treatment site, by introduction intravenously at a site near a desired treatment site (e.g., into a vessel that feeds a treatment site). In some embodiments, the composition can be delivered locally to ischemic tissue. In certain embodiments, the composition can be a slow release formulation, e.g., in the form of a slow release depot.

For injection, the carrier will typically be a liquid, such as sterile pyrogen-free water, pyrogen-free phosphate-buffered saline solution, bacteriostatic water, or Cremophor EL[R] (BASF, Parsippany, N.J.). For other methods of administration, the carrier can be either solid or liquid.

For oral administration, the pharmaceutical composition can be administered in solid dosage forms, such as capsules, tablets, and powders, or in liquid dosage forms, such as elixirs, syrups, and suspensions. Pharmaceutical compositions can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Liquid dosage forms for oral administration can contain coloring and flavoring to increase patient acceptance.

Pharmaceutical compositions suitable for buccal (sublingual) administration include lozenges comprising the compound in a flavored base, usually sucrose and acacia or tragacanth; and pastilles comprising the compound in an inert base such as gelatin and glycerin or sucrose and acacia.

Pharmaceutical compositions can be formulated for nasal administration or otherwise administered to the lungs of a subject by any suitable means, e.g., administered by an aerosol suspension of respirable particles comprising the compound, which the subject inhales. The respirable particles can be liquid or solid. The term "aerosol" includes any gas-borne suspended phase, which is capable of being inhaled into the bronchioles or nasal passages Pharmaceutical compositions of the present disclosure suitable for parenteral administration comprise sterile aqueous and non-aqueous injection solutions of the compound, which preparations are preferably isotonic with the blood of the intended recipient. These preparations can contain antioxidants, buffers, bacteriostats and solutes which render the composition isotonic with the blood of the intended recipient. Aqueous and non-aqueous sterile suspensions can include suspending agents and thickening agents. The compositions can be presented in unit/dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets comprising oligonucleotides of interest. For example, an injectable, stable, sterile composition comprising oligonucleotides of interest, can be provided in a unit dosage form in a sealed container. The oligonucleotides of interest can be provided as a salt, in the form of a lyophilizate which is capable of being reconstituted with a suitable pharmaceutically acceptable carrier to form a liquid composition suitable for injection thereof into a subject.

Methods of Treatment

The disclosure provides methods of treating a disease or disorder in a subject, comprising administering an effective amount of a composition comprising oligonucleotides of interest characterized using the methods described herein.

Any disease or disorder that can be treated by administration of therapeutic oligonucleotide, such as an antisense oligonucleotide, dsRNA, siRNA, aptamer, microRNA or mRNA as described herein, is envisaged as within the scope of the instant disclosure. In some embodiments, the therapeutic oligonucleotides comprise at least one modification as described herein.

Diseases or disorders that can be treated using therapeutic nucleotides include diseases or disorders that can be treated through the modulation or reduction of a target gene. These include genetic diseases, and cancers. Exemplary diseases and disorders that can be treated using therapeutic oligonucleotides include, but are not limited to, retinitis, macular degeneration, homozygous familial hypercholesterolemia, Duchenne muscular dystrophy, severe hepatic veno-occlusive disease (sVOD) occurring after high dose chemotherapy and autologous bone marrow transplantation and spinal muscular atrophy (SMA), amyotrophic lateral sclerosis (ALS), Parkinson's disease, and Ataxia-telangiectasia. As a further example, additional diseases thought to be treatable with therapeutic oligonucleotides include cancers (including, for example, lung cancer, colorectal carcinoma, pancreatic carcinoma, malignant glioma and malignant melanoma), diabetes, and inflammatory diseases such as asthma, arthritis and pouchitis with an inflammatory component.

The disclosure provides methods of preventing, or reducing the severity, of a disease or disorder in a subject, comprising administering an effective amount of a composition comprising oligonucleotides of interest characterized using the methods described herein. For example, oligonucleotide vaccines characterized using the methods described herein can be administered to the subject to reduce, or prevent the severity of infectious diseases or cancers.

A "therapeutically effective" amount as used herein is an amount that provides some improvement or benefit to the subject. Alternatively stated, a "therapeutically effective" amount is an amount that will provide some alleviation, mitigation, or decrease in at least one clinical symptom in the subject (e.g., in the case of cancer, reduction in tumor burden, prevention of further tumor growth, prevention of metastasis, or increase in survival time) Those skilled in the art will appreciate that the therapeutic effects need not be complete or curative, as long as some benefit is provided to the subject.

By the terms "treat," "treating." or "treatment of," it is intended that the severity of the subject's condition is reduced or at least partially improved or modified and that some alleviation, mitigation or decrease in at least one clinical symptom is achieved Kits and Articles of Manufacture The disclosure provides kits and articles of manufacture for characterizing oligonucleotides and compositions comprising same using the methods described herein.

In some embodiments, the kit comprises buffers, reagents, control samples and instructions for methods of use.

In some embodiments, the kit comprises dosage forms comprising the oligonucleotides of interest for the treatment of a disease or disorder, and instructions for use.

The following examples are not intended to limit the scope of the claims to the invention, but are rather intended to be exemplary of certain embodiments. Any variations in the exemplified methods that occur to the skilled artisan are intended to fall within the scope of the present invention. As will be understood by one skilled in the art, there are several embodiments and elements for each aspect of the claimed invention, and all combinations of different elements are hereby anticipated, so the specific combinations exemplified herein are not to be construed as limitations in the scope of the invention as claimed. If specific elements are removed or added to the group of elements available in a combination, then the group of elements is to be construed as having incorporated such a change.

EXAMPLES

Example 1: HILIC-UV Detection of Modified and Unmodified Oligonucleotides

The ability of hydrophobic interaction liquid chromatography and ultraviolet detection (HILIC-UV) to resolve small unmodified and modified oligonucleotides was assayed.

FIG. 1 shows HILIC-UV analysis of representative unmodified and modified oligonucleotides, the sequences and modifications of which are described in Table 3 below. Custom oligonucleotides in Table 3 were ordered from IDTDNA.

HILIC-UV was carried out using a Phenomenex Luna 3 μm HILIC 200 Å, LC Column, 150×2 mm. Chromatography was carried out with a flow rate of 0.25 mL/min. Mobile Phase solvent A (MPA) was 15 mM ammonium acetate in 70% acetonitrile (ACN). Mobile Phase solvent B (MPB) was 15 mM ammonium acetate in 30% ACN. FIG. 1 shows that HILIC-UV can resolve representative modified and unmodified oligonucleotides.

TABLE 3

Custom oligonucleotides used in the Examples

| SEQ ID NO: | Name | Sequence (5' to 3') | Molecular Weight (Da) |
|---|---|---|---|
| 1 | M13 Reverse (M13-R) | CAGGAAACAGCTATGAC (SEQ ID NO: 1) | 5212.5 |
| 2 | SP6 | ATTTAGGTGACACTATAG (SEQ ID NO: 6) | 5537.7 |
| 3 | T7 | TAATACGACTCACTATAGGG (SEQ ID NO: 3) | 6125.1 |
| 4 | T3 | GCAATTAACCCTCACTAAAGG (SEQ ID NO: 7) | 6383.2 |
| 5 | CMV Forward (CMV-F) | CGCAAATGGGCGGTAGGCGTG (SEQ ID NO: 8) | 6552.3 |
| 6 | TRC-F | CAAGGCTGTTAGAGAGATAATTGGA (SEQ ID NO: 2) | 7794.2 |
| 7 | Oblimersen | T*C*T*C*C*C*A*G*C*G*T*G*C*G*C*C*A*T (SEQ ID NO: 5) | 5684.6 |
| 8 | Formivirsen sodium | G*C*G*T*T*T*G*C*T*C*T*T*C*T*T*G*C*G (SEQ ID NO: 9) | 6682.4 |

(*) indicates phosphorothioate linkages (PS)

Figure 2A:
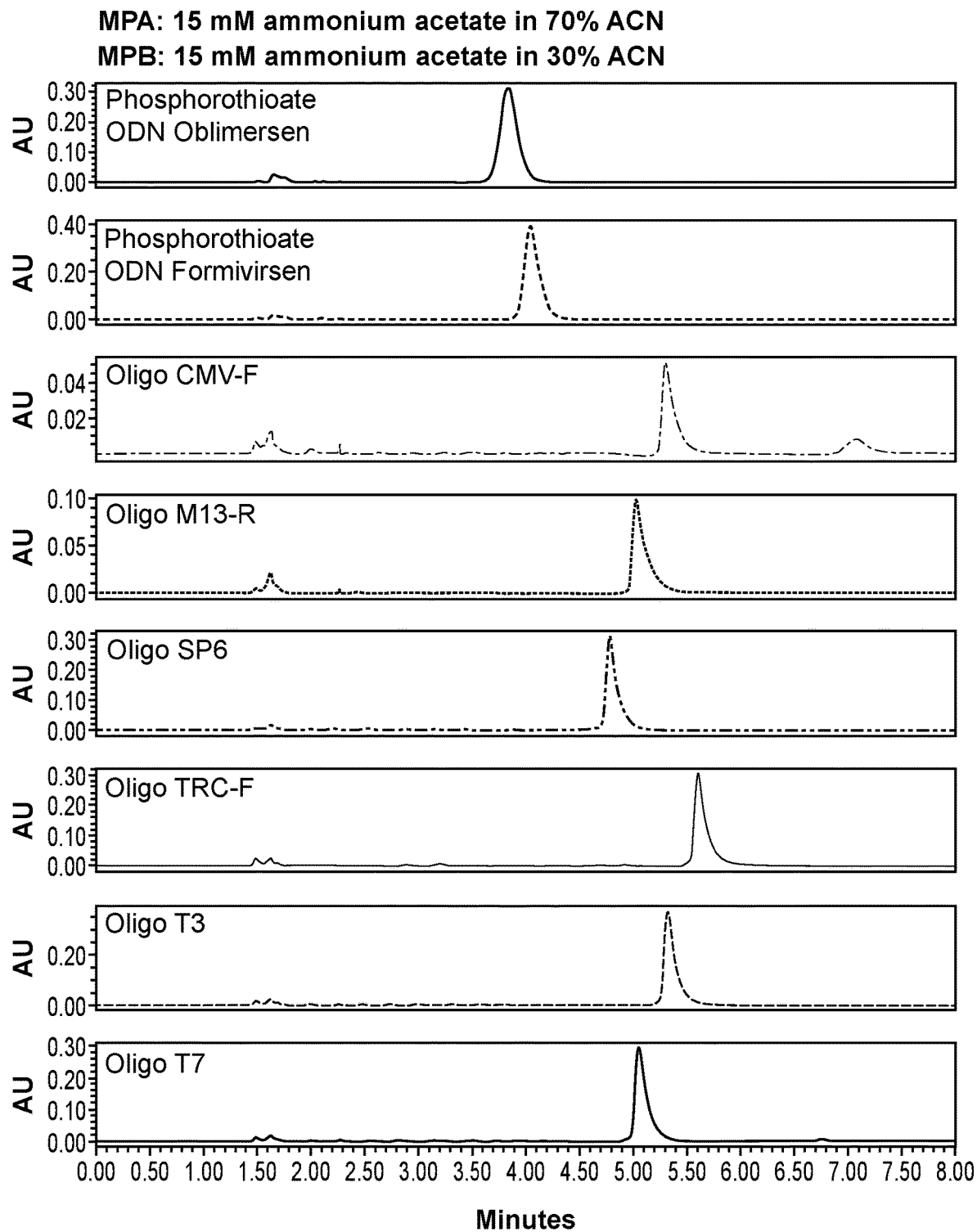
FIG. 2A is a series of chromatograms showing, from top to bottom, Phosphorothioate oligonucleotide (ODN) Oblimersen, Phosphorothioate ODN Fomivirsen, Oligo CMV-F, Oligo M13-R, Oligo SP6, Oligo TRC-F, Oligo T3 and Oligo T7 using HILIC-UV detection. MPA: 15 mM ammonium acetate in 70% ACN; MPB: 15 mM ammonium acetate in 30% ACN.
Figure 2B:
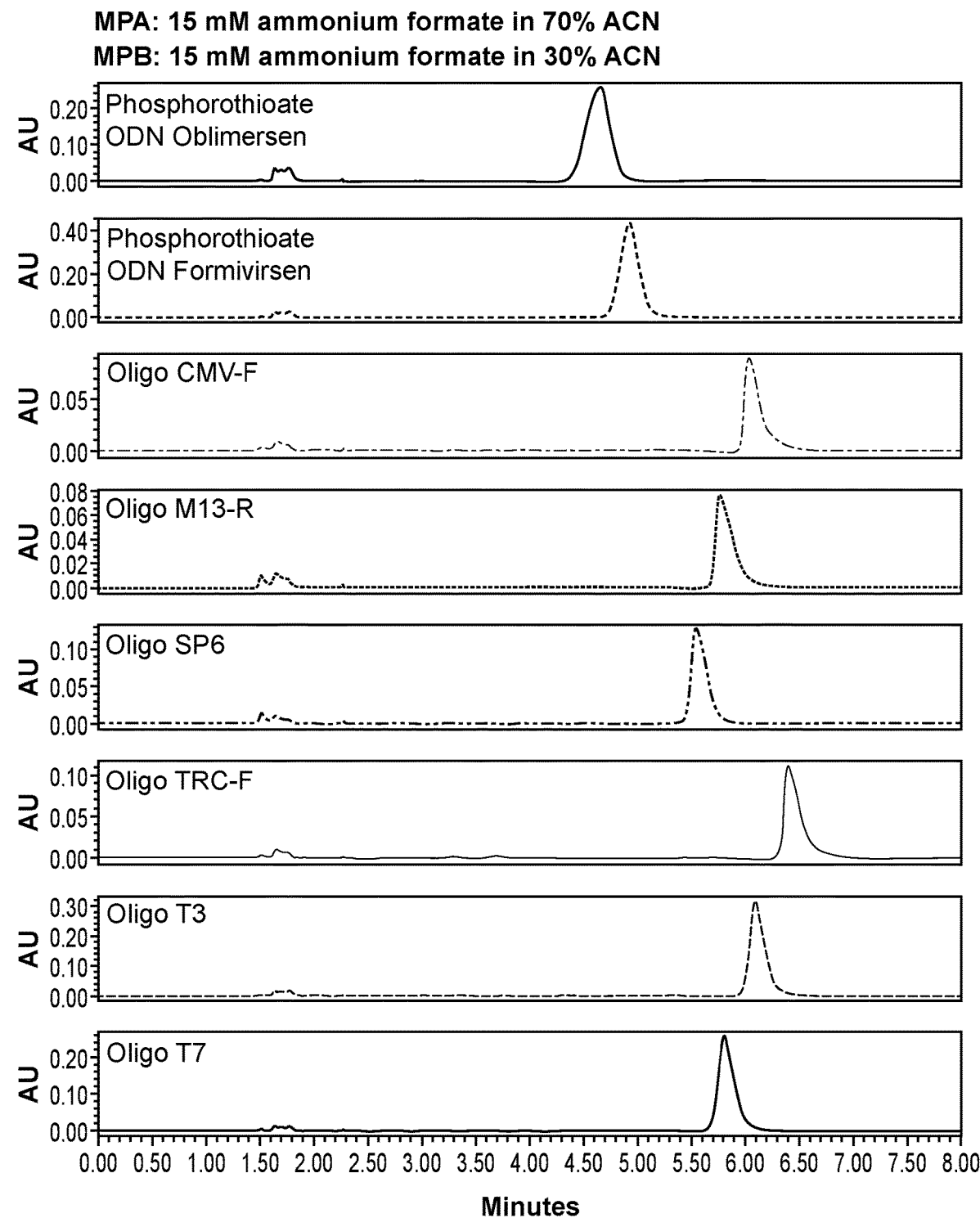
FIG. 2B is a series of chromatograms showing, from top to bottom, Phosphorothioate ODN Oblimersen, Phosphorothioate ODN Fomivirsen, Oligo CMV-F, Oligo M13-R, Oligo SP6, Oligo TRC-F, Oligo T3 and Oligo T7 using HILIC-UV detection. MPA: 15 mM ammonium formate in 70% ACN; MPB: 15 mM ammonium formate in 30% ACN.

FIGS. 2A and 2B show a comparison of the analytical performance between two HILIC buffer systems using representative unmodified and modified oligonucleotides from Table 3. In FIG. 2A, MPA and MPB were carried out with 15 mM ammonium acetate in 70% and 30% ACN, respectively. In FIG. 2B, MPA and MPB were carried out with 15 mM ammonium formate in 70% and 30% ACN, respectively. 15 mM ammonium acetate was chosen as the buffer.

Figures 3A, 3B:
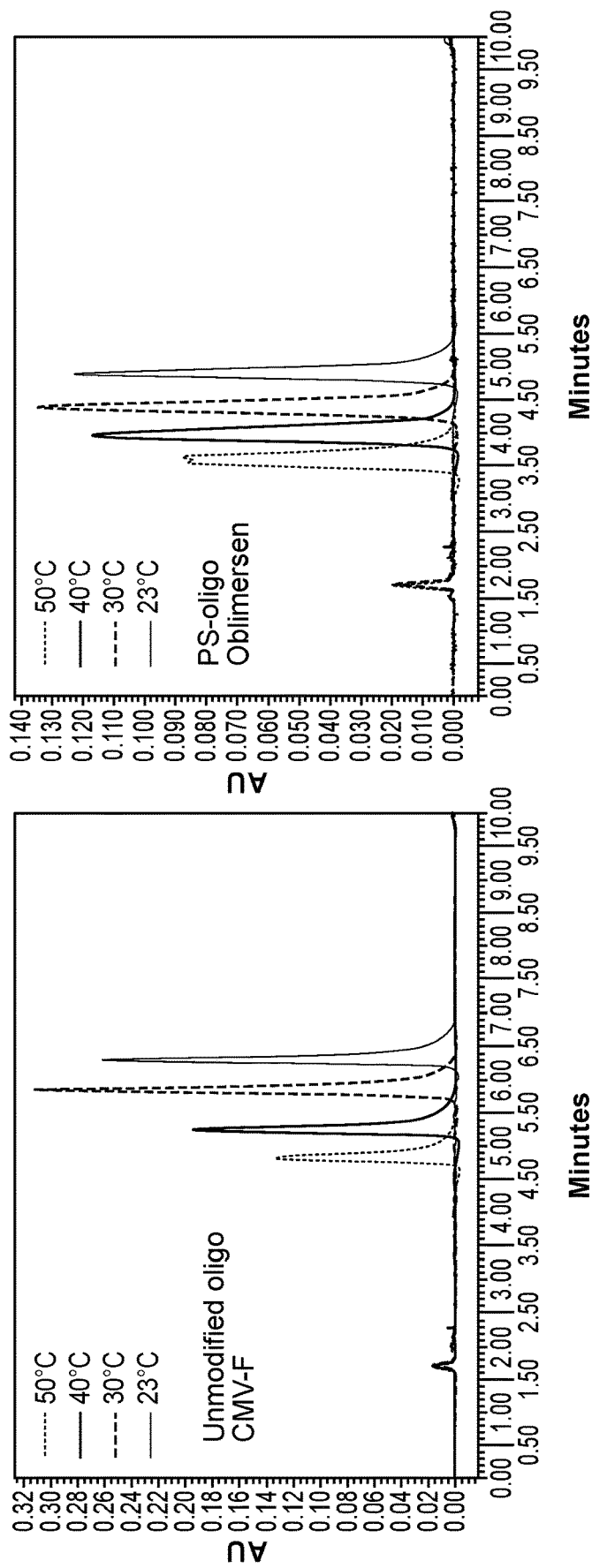
FIG. 3A is a chromatogram comparing analytical performance of the HILIC-UV system at 50° C., 40° C., 30° C. and 23° C. (major peaks ordered from left to right) using the unmodified oligo CMV-F and a 15 mM ammonium acetate buffer system.
FIG. 3B is a chromatogram comparing analytical performance of the HILIC-UV system at 50° C., 40° C., 30° C. and 23° C. (major peaks ordered from left to right) using the PS-oligo Oblimersen and a 15 mM ammonium acetate buffer system.

FIGS. 3A and 3B show a comparison of the analytical performance of different column temperatures using oligonucleotides unmodified CMV-F and phosphorothioate (PS) modified Oblimersen. Column temperatures of 23° C., 30° C., 40° C. and 50° C. were assayed. 30° C. was selected as the column temperature.

Example 2: IP-RPLC-UV Detection of Modified and Unmodified Oligonucleotides

The ability of Ion-pairing Reversed-Phase Liquid Chromatography and ultraviolet detection (IP-RPLC-UV) to resolve small unmodified and modified oligonucleotides was assayed.

Figure 4:
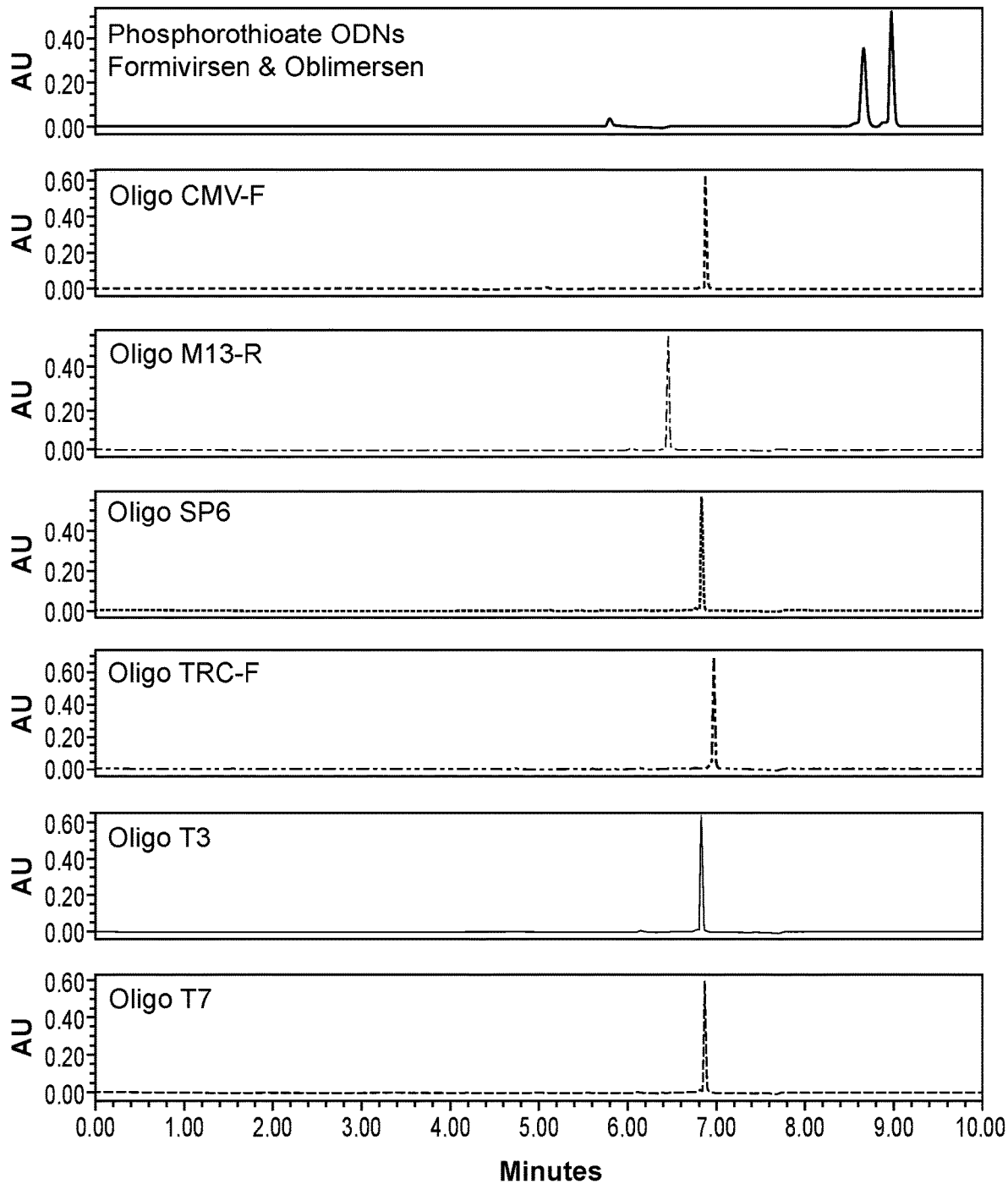
FIG. 4 is a series of chromatograms that show Ion-pairing Reversed-Phase Liquid Chromatography and ultraviolet (IP-RPLC-UV) detection of PS-modified oligonucleotides and unmodified oligonucleotides on a Waters Acquity Oligonucleotide BEH column. Oligonucleotides, from top to bottom, are: Phosphorothioate ODNs Fomivirsen and Oblimersen, Oligo CMV-F, M13-R, Oligo SP6, Oligo TRC-F, Oligo T3 and Oligo T7.

FIG. 4 shows IP-RPLC-UV analysis of representative unmodified and modified oligonucleotides, the sequences and modifications of which are described in Table 3 below. IP-RPLC-UV detection was carried out using a Waters Acquity Oligonucleotide BEH column. FIG. 4 shows that IP-RPLC-UV can resolve representative modified and unmodified oligonucleotides.

Figure 5:
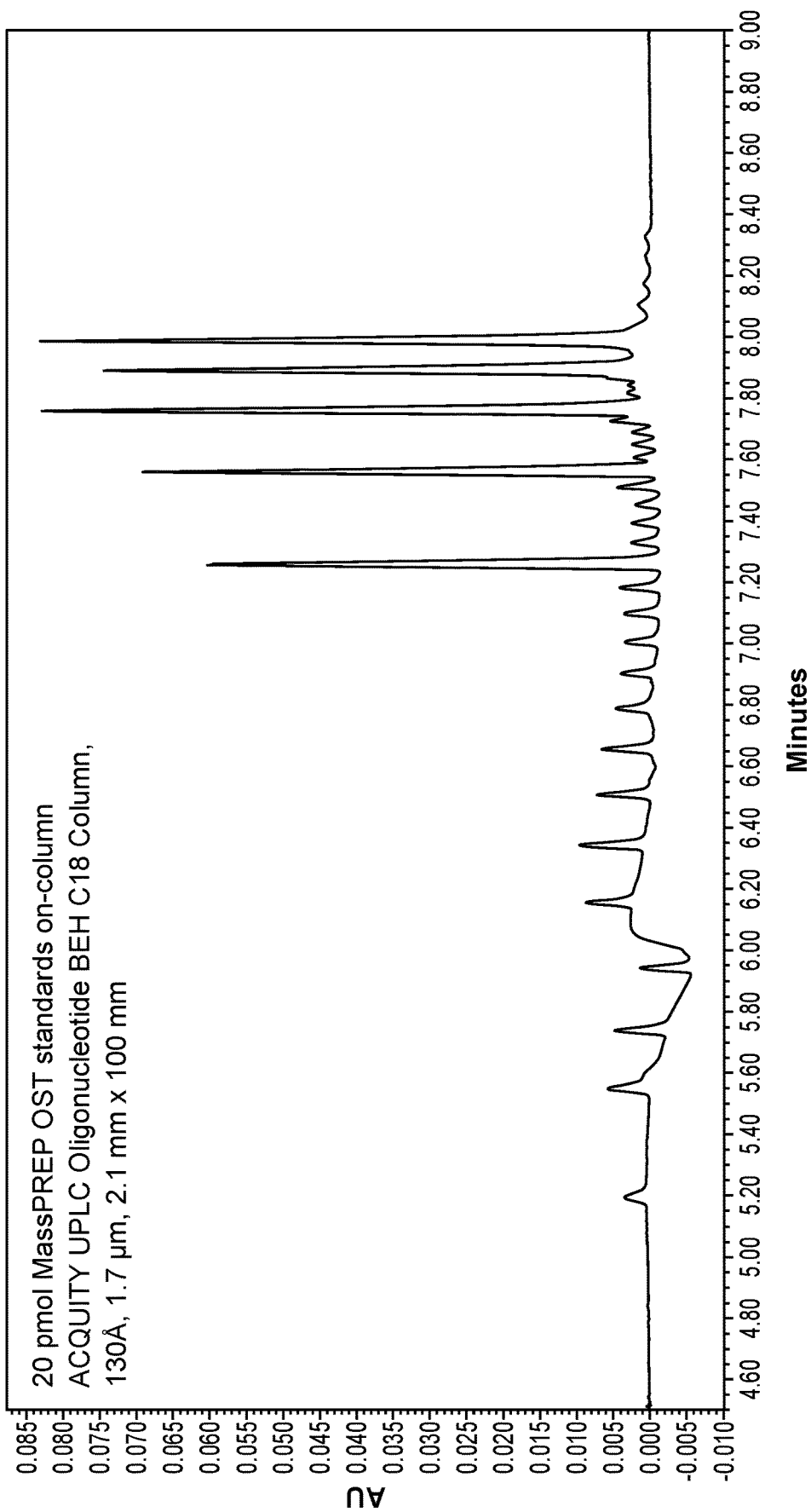
FIG. 5 is a chromatogram showing Ion-Pairing Reversed-Phase Liquid Chromatography with UV detection (IP-RPLC-UV) separation of 20 pmol MassPrep OST standard oligos on a Waters Acquity UPLC Oligonucleotide BEH C18 column, 130 Å, 1.7 μm, 2.1 mm×100 mm.
Figure 6:
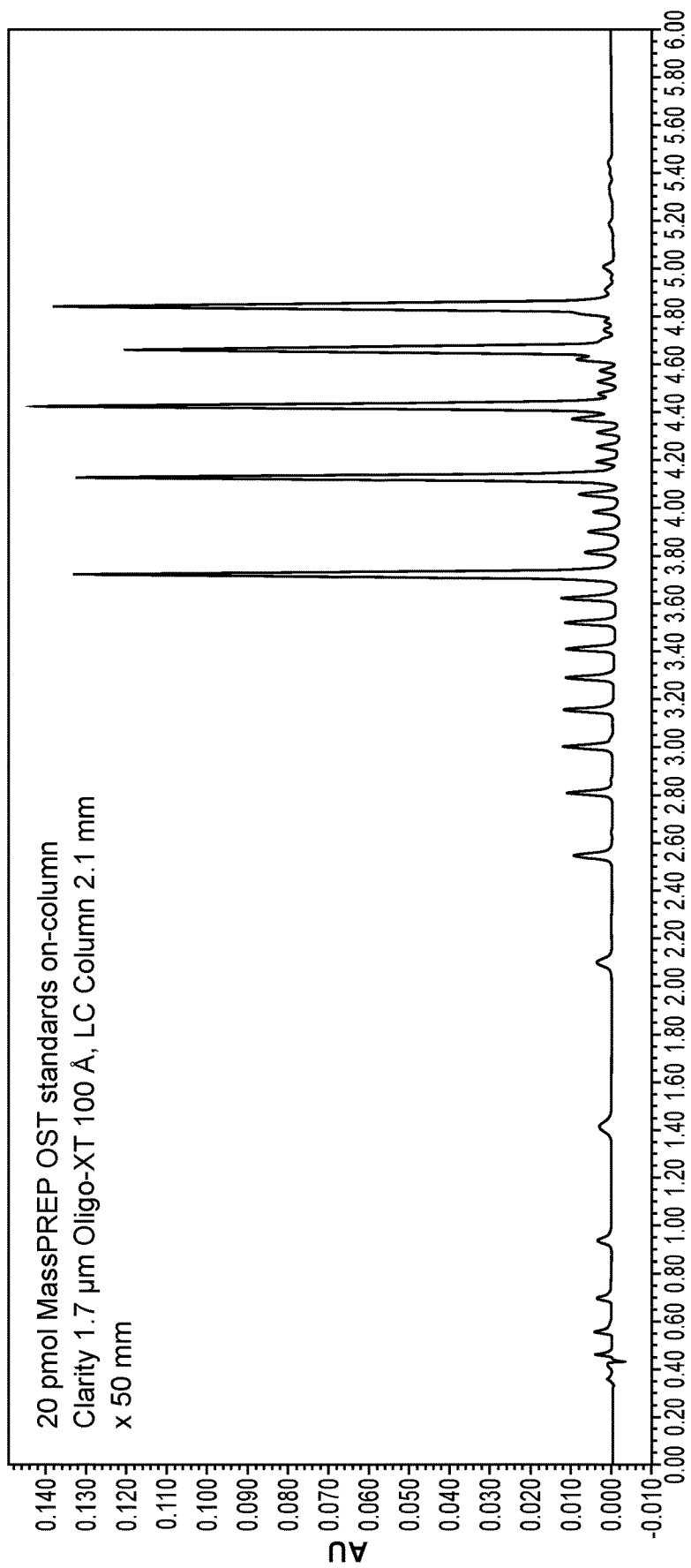
FIG. 6 is a chromatogram showing IP-RPLC-UV separation of 20 pmol MassPrep OST standard oligos on a Clarity 1.7 μm Oligo-XT 100 Å, LC Column, 2.1 mm×50 mm.

IP-RPLC-UV can also resolve a sample of mixed oligonucleotides, as shown in FIGS. 5 and 6. IP-RPLC-UV was used to analyze MassPrep OST standards (sequences provided in Table 4 below).

In FIG. 5, mixed MassPrep OST standards were run on a Waters Acquity Oligonucleotide BEH column. Flow and Column Temperature were 0.25 mL/minute (60° C.). MPA was 50 mM Hexafluoroisopropanol (HFIP) and 5 mM N,N-Diisopropylethylamine (DIEA) in water. MPB was 50 mM HFIP and 5 mM DIEA in acetonitrile. The column was an ACQUITY UPLC Oligonucleotide BEH C18 Column, 130 Å, 1.7 μm, 2.1 mm×100 mm.

In FIG. 6, mixed MassPrep OST standards were run on a Phenomenex Oligo-XT column using IP-RPLC-UV. Flow and Column Temperature were 0.25 mL/min (60° C.). MPA was 50 mM HFIP and 5 mM DIEA in water. MPB was 50 mM HFIP and 5 mM DIEA in acetonitrile. The column was a Clarity® 1.7 μm Oligo-XT 100 Å, LC Column 2.1 mm×50 mm.

TABLE 4

Waters MassPrep OST oligonucleotide standard mixture

| SEQ ID NO: | Name | Sequence (5' to 3') | Molecular Weight (Da) |
|---|---|---|---|
| 9 | 15-nt | TTTTT TTTTT TTTTT (SEQ ID NO: 10) | 4500.99 |
| 10 | 20-nt | TTTTT TTTTT TTTTT TTTTT (SEQ ID NO: 11) | 6021.98 |
| 11 | 25-nt | TTTTT TTTTT TTTTT TTTTT TTTTT (SEQ ID NO: 12) | 7542.96 |
| 12 | 30-nt | TTTTT TTTTT TTTTT TTTTT TTTTT TTTTT (SEQ ID NO: 13) | 9063.95 |
| 13 | 35-nt | TTTTT TTTTT TTTTT TTTTT TTTTT TTTTT TTTTT (SEQ ID NO: 14) | 10584.93 |

Example 3: Liquid Chromatography and Tandem Mass Spectrometry Characterization of Oligonucleotides Liquid chromatography (HILIC or IP-RPLC) and tandem mass spectrometry (MS/MS) was used to detect precursor ions with different charges (z) in samples of unmodified oligonucleotide M13-R following ionization.

Figure 7:
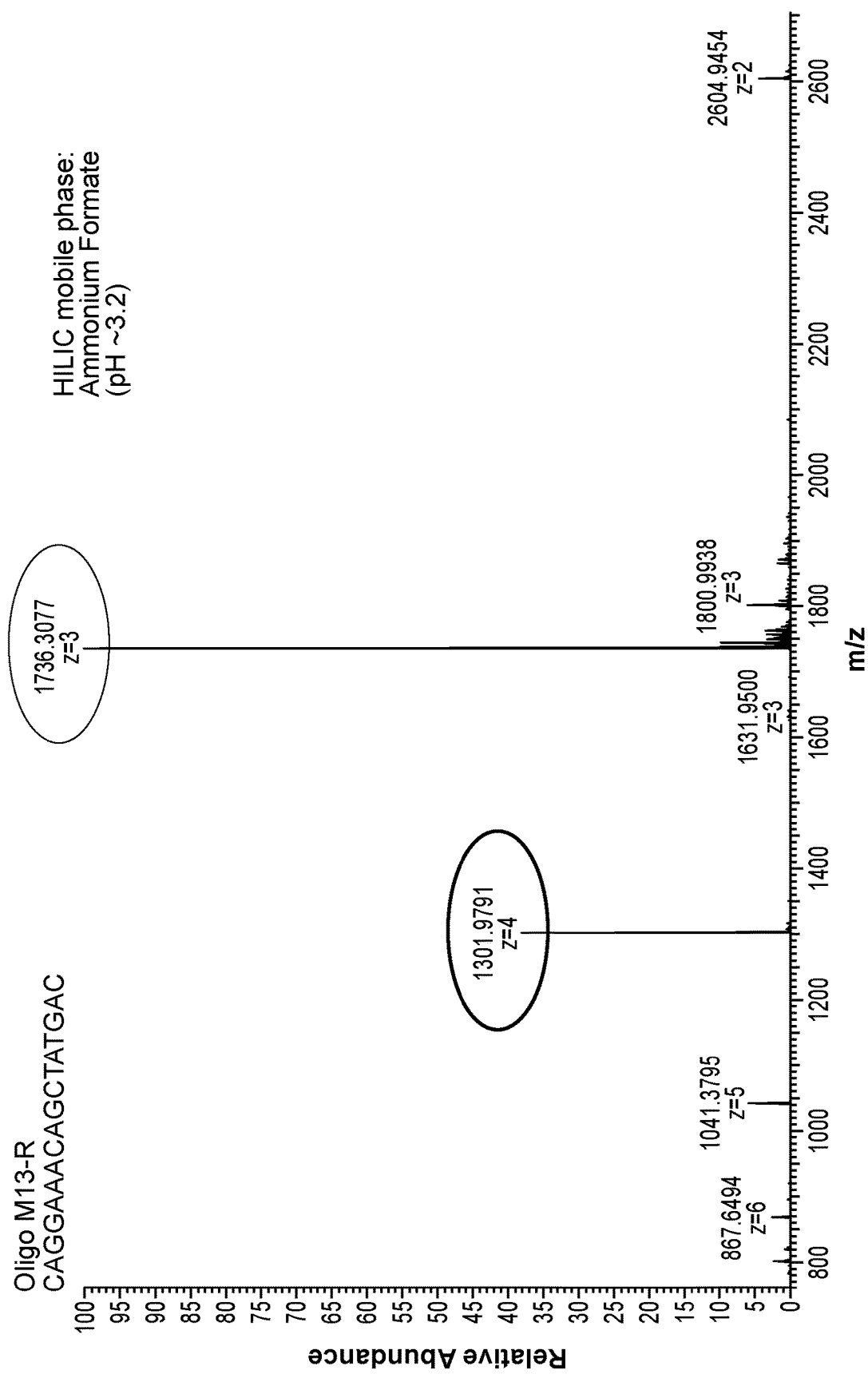
FIG. 7 is a mass spectrum showing m/z (mass to charge) ratio (x-axis) versus relative abundance (y-axis) of a sample of M13-R oligonucleotide that was analyzed with HILIC-DDA (Hydrophilic Interaction Liquid Chromatography and Data Dependent Acquisition mode of tandem mass spectrometry). HILIC mobile phase was buffered with ammonium formate, pH approximately 3.2.

FIG. 7 shows HILIC with an ammonium formate mobile phase, pH approximately 3.2 followed by Data Dependent Acquisition (DDA) MS/MS. As can be seen from FIG. 7, under these conditions the z=4- and z=3-oligo precursor ions predominate.

Figure 8:
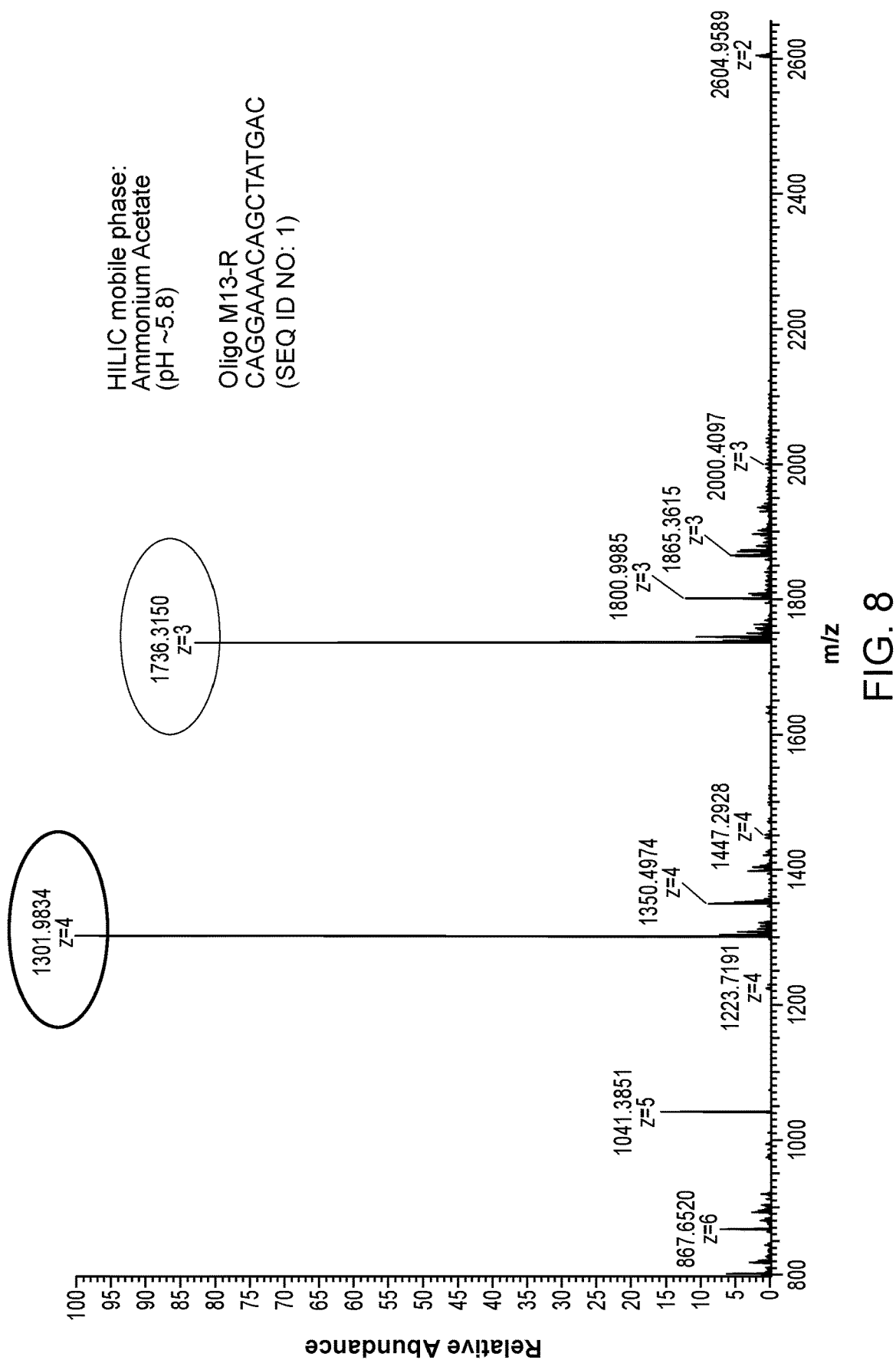
FIG. 8 is a mass spectrum showing m/z ratio (x-axis) versus relative abundance (y-axis) of a sample of M13-R oligonucleotide (SEQ ID NO: 1), that was analyzed with HILIC-DDA. HILIC mobile phase was buffered with ammonium acetate, pH approximately 5.8.

FIG. 8 shows HILIC with an ammonium acetate mobile phase, pH approximately 5.8 followed by DDA MS/MS. As can be seen from FIG. 8 under these conditions the z=4- and z=3-oligo precursor ions predominate.

Figure 9:
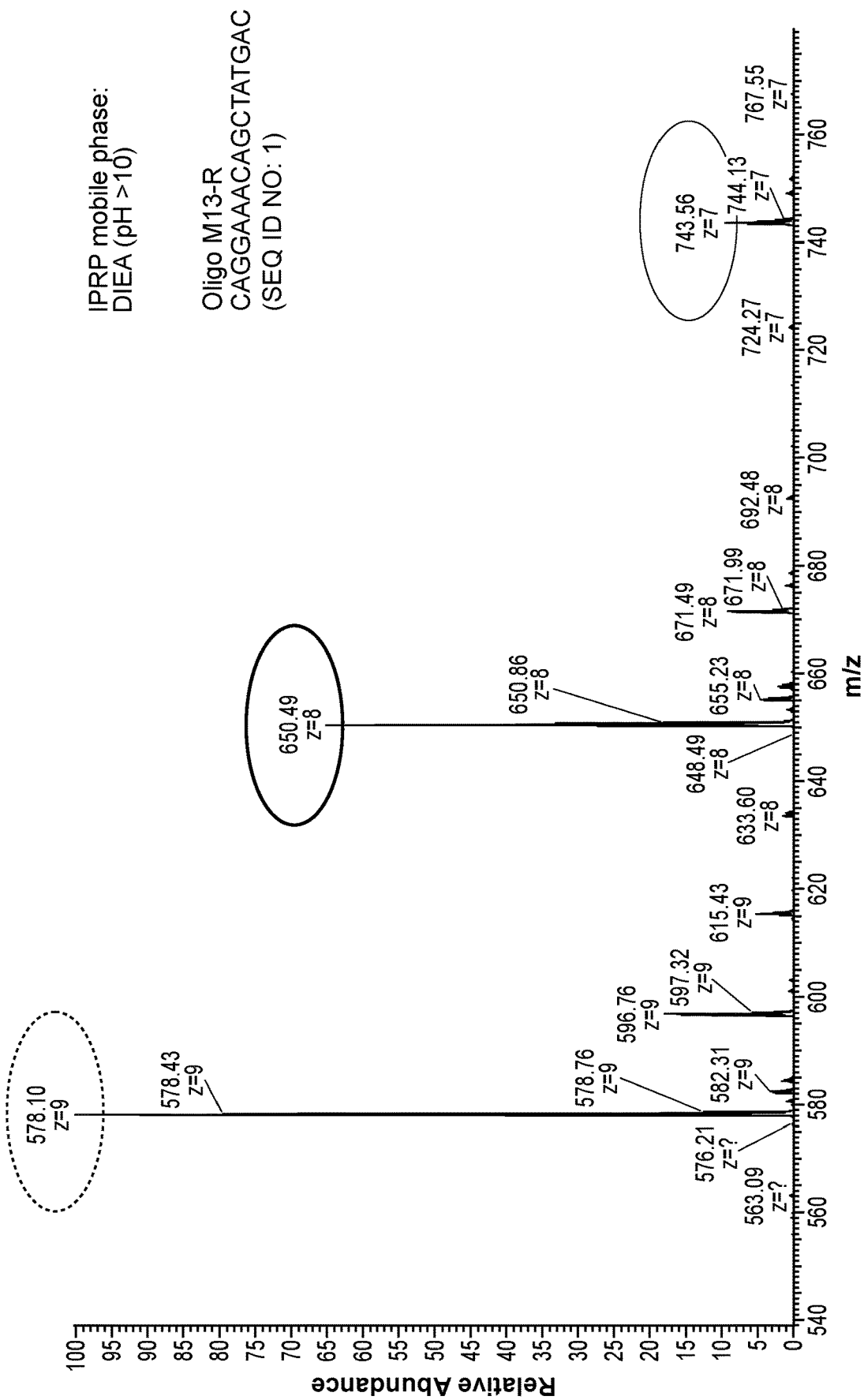
FIG. 9 is a plot showing m/z ratio (x-axis) versus relative abundance (y-axis) of a sample of M13-R oligonucleotide of SEQ ID NO: 1 that was analyzed with IPRP-LC-DDA (Ion-pairing Reversed-Phase Liquid Chromatography and Data Dependent Acquisition mode of tandem mass spectrometry). The IPRP mobile phase comprised DIEA (N,N-Diisopropylethylamine), with a pH greater than 10.

FIG. 9 shows IP-RPLC with a DIEA mobile phase (pH greater than 10), followed by DDA MS/MS. As can be seen in FIG. 9, under these conditions the z=9-, 8- and 7-precursor ions of M13-R predominate.

Example 4: Intact Mass Analysis of Unmodified Oligonucleotides

Figures 10A, 10B:
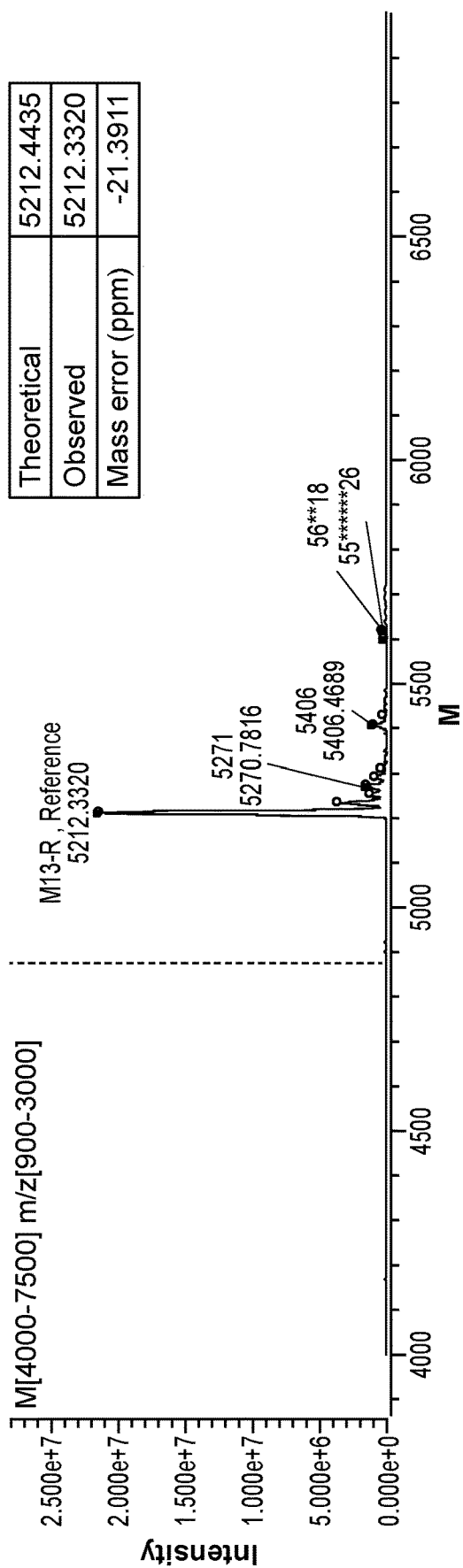
FIG. 10A is a plot showing mass versus intensity of a sample of M13-R oligonucleotide. Inset table provides the theoretical and observed mass of full-length M13-R and the mass error in parts per million (ppm).
FIG. 10B is a table showing relative abundance of full-length M13-R (reference) and M13-R truncated at nucleotides 4-17. Relative abundance of truncation impurities was calculated by intact mass analysis. The sample was 0.09% 4-17 nucleotide truncation product and 99.91% reference M13-R.
Figures 11A, 11B:
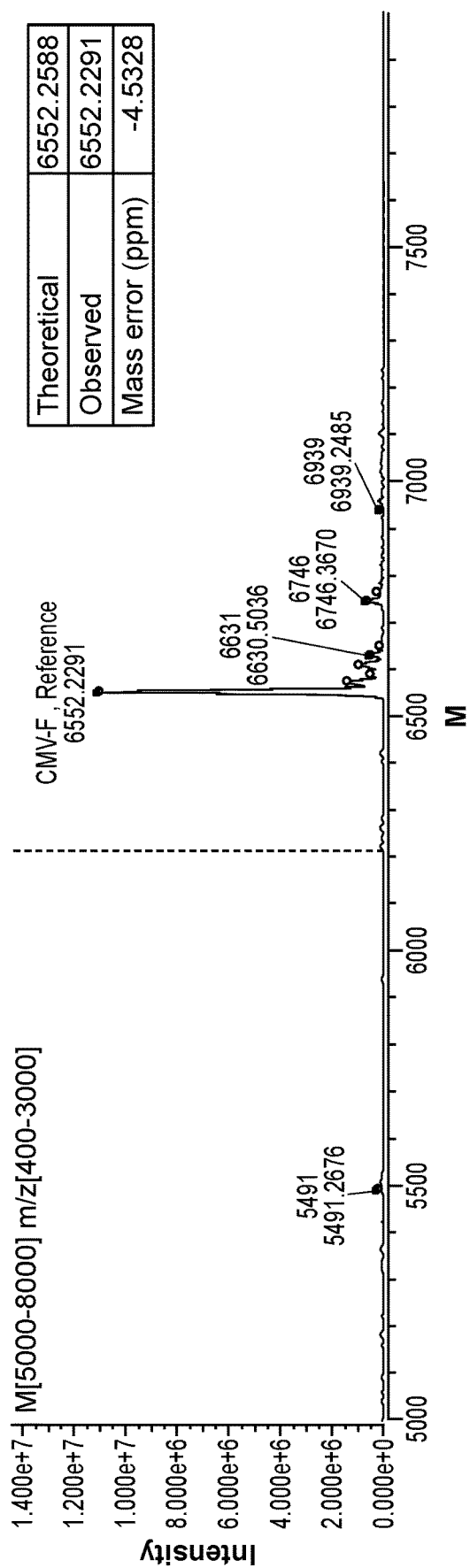
FIG. 11A is a plot showing mass versus intensity of a sample of unmodified CMV-F oligonucleotide. Inset table provides the theoretical and observed mass of full-length CMV-F and the mass error in ppm.
FIG. 11B is a table showing relative abundance of full-length CMV-F (CMV-F Reference) and CMV-F truncated at nucleotides 5-21 and 1-19. Relative abundance of truncation impurities was calculated by intact mass analysis. The sample was 1.19% 5-21 nucleotide truncation product, 7.49% 1-19 nucleotide truncation product, and 91.31% Reference.

PMI Intact software was used to calculate the intact mass of unmodified oligonucleotide M13-R (FIGS. 10A and 10B) and unmodified oligonucleotide CMV-F (FIGS. 11A and 11B) and the percentage of intact M13-R and CMV-F oligonucleotides versus truncation purities in oligonucleotide samples.

Figure 13:
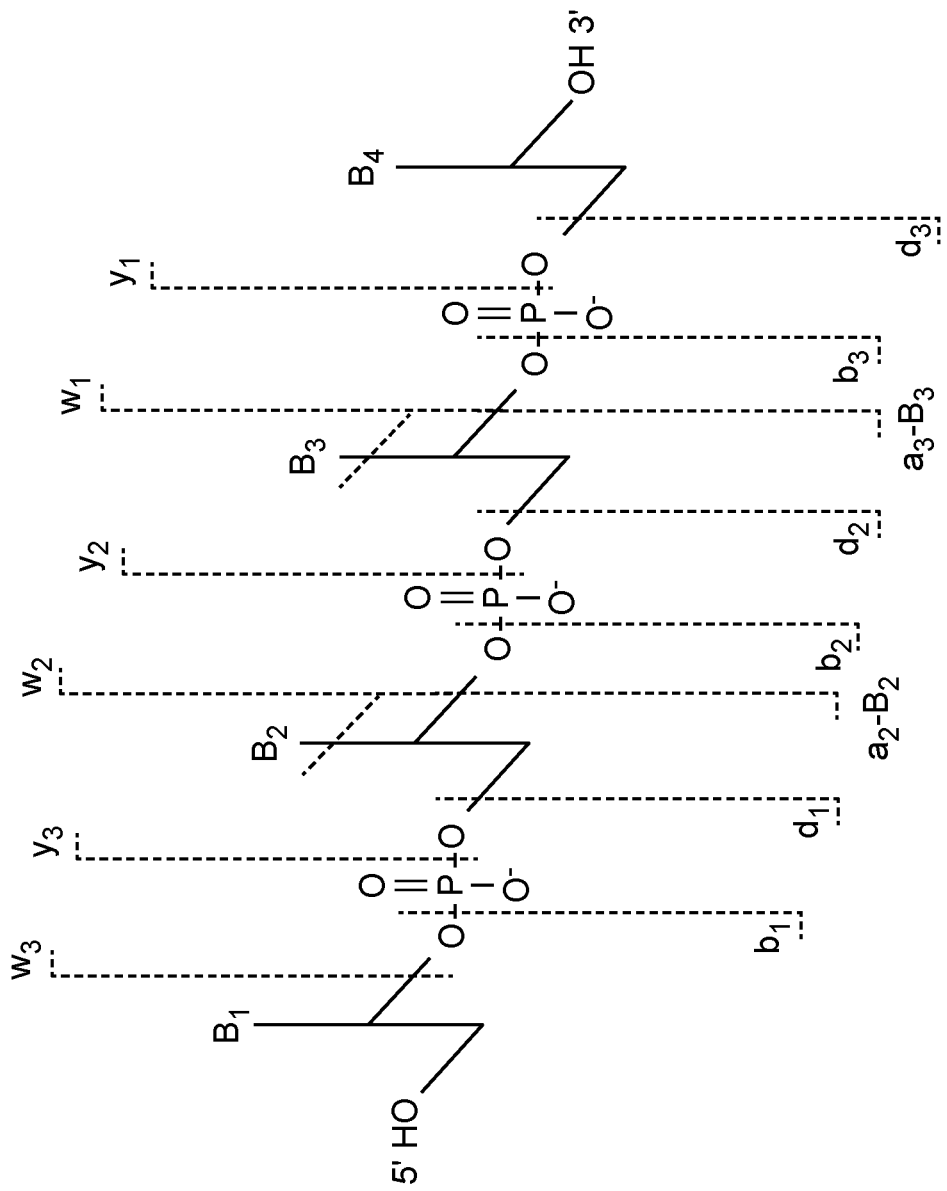
FIG. 13 is a diagram showing a tandem mass spectrometry (MS/MS) fragmentation scheme of oligonucleotides.

This same approach can be used to characterize modified oligonucleotides, such as the commercial oligonucleotide drugs whose sequences are shown in Table 5.

y). DNA oligos produce a-B and w ions as the most abundant fragments. RNA oligos favor the production of y and d-H2O ions. (See McLuckey et al. JASMS, 1992, 3: 60-70 and FIG. 13).

Figure 14A:
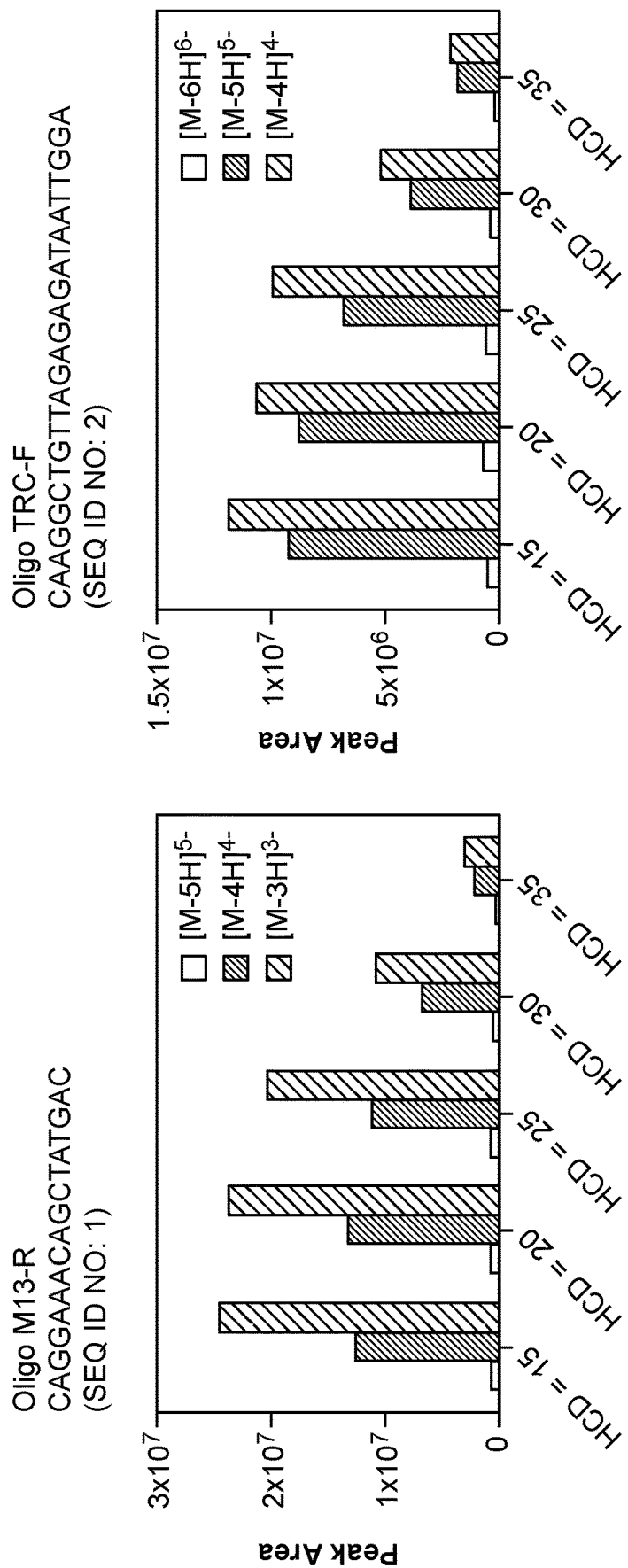
FIG. 14A is a pair of plots showing peak areas (y-axis) for different Higher-energy Collisional Dissociation (HCD) collisional energies for HILIC-MS/MS (tandem mass spectrometry) with two representative oligonucleotides M13-R and TRC-F (left and right panels, respectively).
Figure 14B:
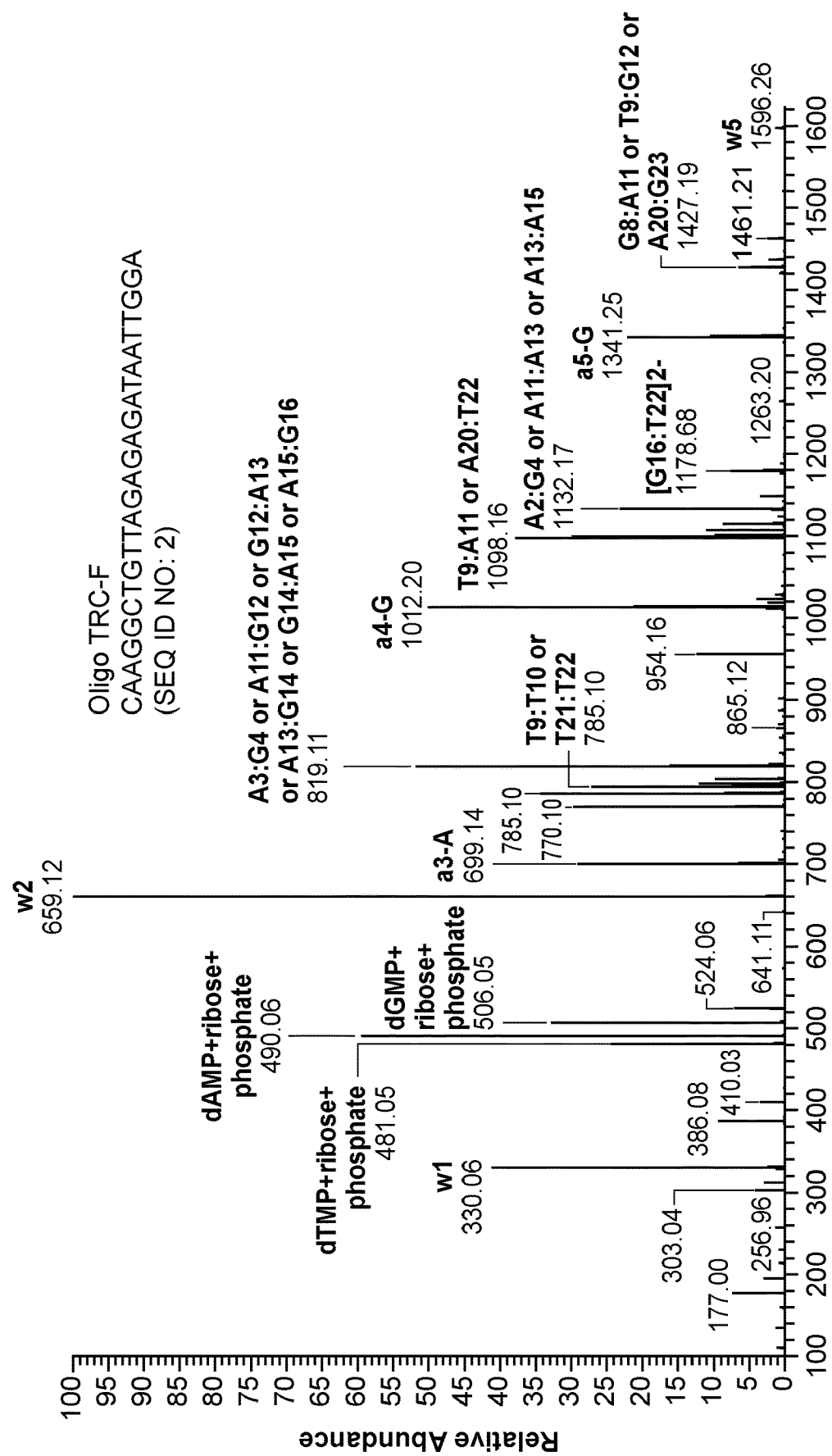
FIG. 14B is a representative HILIC-MS/MS plot showing m/z (x-axis) and relative abundance with a representative oligonucleotide TRC-F.

HCD collisional energies for HILIC-MS/MS were optimized, as shown in FIGS. 14A and 14B. HCD NCE of 15-20% were determined as the optimal collisional energies for most oligonucleotide sequences.

Figure 15:
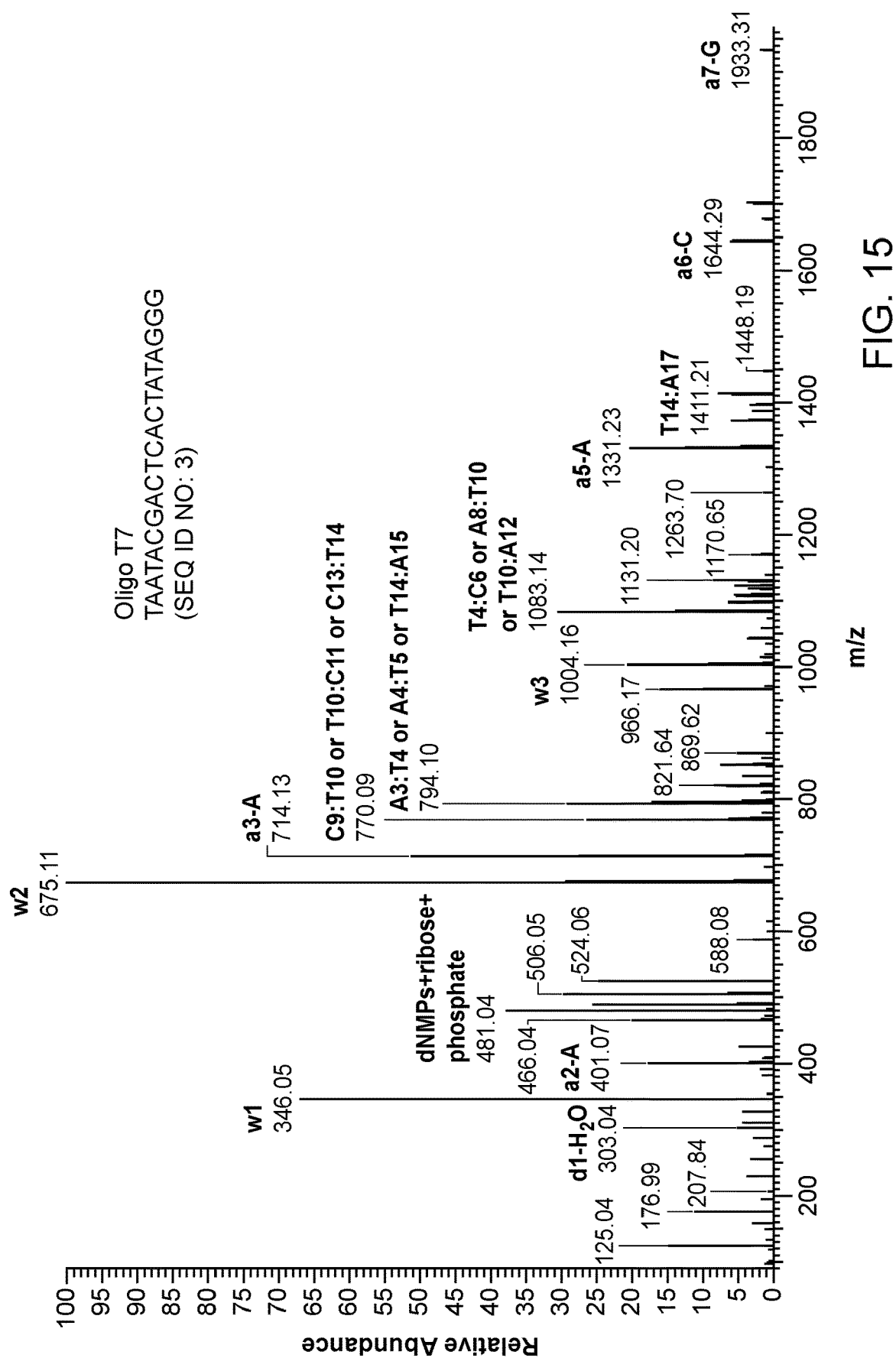
FIG. 15 is a plot showing fragmentation of the $[M-4H]^{4-}$ (m/z 1530.2549) precursor of oligonucleotide T7 with HCD at 20.
Figure 18:
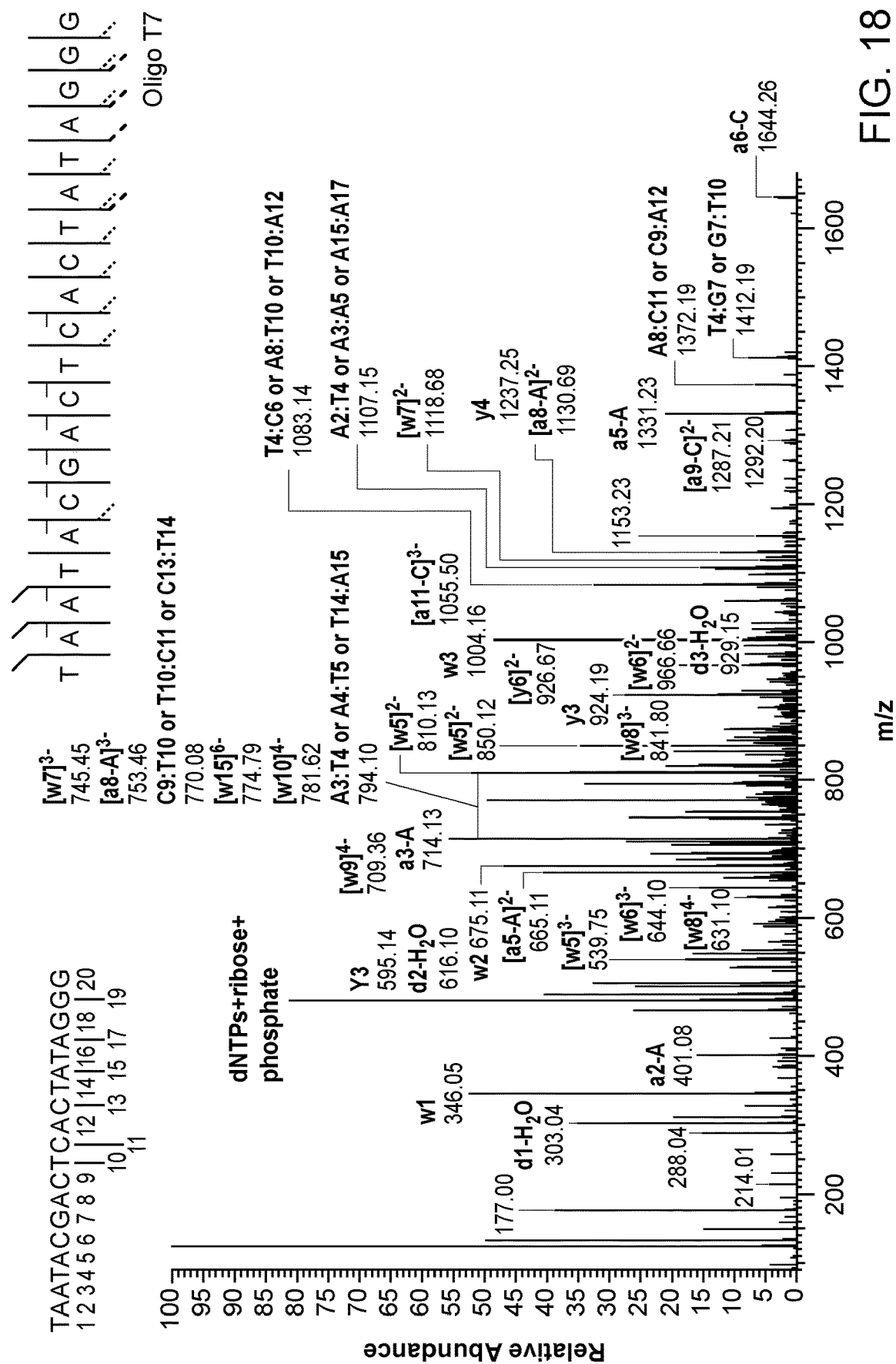
FIG. 18 is a plot showing fragmentation of the [M−8H]$^{8-}$ (m/z 898.0009) precursor of oligo T7 with HCD at 20. Oligo sequences in FIG. 18 are T7 sequences (SEQ ID NO: 3).

Exemplary fragmentation of the $[M-4H]^{4-}$ (m/z 1530.2549) and $[M-8H]^{8-}$ ion precursors of oligonucleotide T7 are shown in FIGS. 15 and 18, respectively. HCD of 20% was used in each case. In FIG. 18, fragmentation at the 3' side (C-O) of T in DNA is often absent; fragmentation at the 5' side (P-O) of T produces strong signals.

TABLE 5

Tests with existing template using commercial oligonucleotide drugs with known sequence and molecular formula

| Name | Sequence | Converted sequence in PMI-Intact | MW calculation Skyline | PMI-Intact |
|---|---|---|---|---|
| Nusinersen | MOErT*MOErC(5me)*MOErA* MOErC(5me)*MOErT*MOErT* MOErT*MOErC(5me)*MOErA* MOErT*MOErA*MOErA*MOErT* MOErG*MOErC(5me)*MOErT* MOErG*MOErG (SEQ ID NO: 15) | DBEBDDD BEDEEDFB DFF (SEQ ID NO: 15) | 7127.2 Da | 7127.20 Da |
| Inotersen | MOErT*MOErC(5me)*MOErT* MOErT*MOErG*G*T*T*A*C(5me)* A*T*G*A*A*MOErA*MOErT* MOErC(5me)*MOErC(5me)*MOErC (5me) (SEQ ID NO: 16) | DBDDFGTT AHATGAA EDBBB (SEQ II NO: 16) | 7183.1 Da | 7183.12 Da |
| Mipomersen | MOErG*MOErC(5me)*MOErC(5me)* MOErT*MOErC(5me)*A*G*T* C(5me)*T*G*C(5me)*T*T*C (5me)* MOErG*MOErC(5me)*MOErA* MOErC(5me)*MOErC(5me) (SEQ ID NO: 17) | FBBDBAGT HTGHTTHF BEBB (SEQ ID NO: 17) | 7177.2 Da | 7177.15 Da |
| AZD4785 (discont'd) | G(cEt)*C(cEt)*T(cEt)*A*T*T* A*G*G*A*G*T*C*T(cEt)*T(cEt)* T(cEt) (SEQ ID NO : 18) | LIJATTAGG AGTCJJJ (SEQ II NO: 18) | 5411.4 Da | 5411.44 Da |

Figures 12A, 12B:
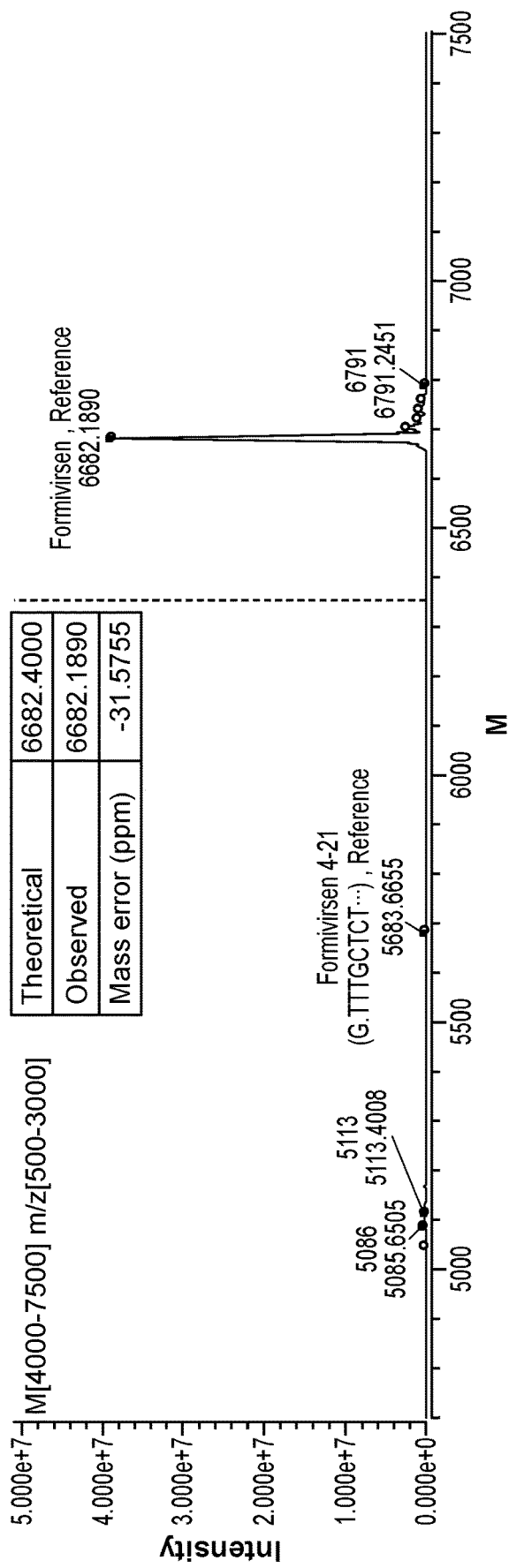
FIG. 12A is a plot showing mass versus intensity of a sample of phosphorothioate (PS) modified oligonucleotide Fomivirsen. Inset table provides the theoretical and observed mass of full-length Fomivirsen and the mass error in ppm.
FIG. 12B is a table showing relative abundance of full-length Fomivirsen (Fomivirsen Reference) and Fomivirsen truncated at nucleotides 6-21, 4-21, and 1-15. Relative abundance of truncation impurities was calculated by intact mass analysis. The sample was 2.22% 6-21 nucleotide truncation product, 0.50% 4-21 nucleotide truncation product, 1.43% 1-15 nucleotide truncation product, and 95.86% Reference.

FIGS. 12A and 12B show that intact mass analysis can be used to calculate the intact mass of Fomivirsen, and shows the percentages of intact Fomivirsen and Fomivirsen truncation products in a sample. See Table 2 for an explanation of codes and modifications.

Example 5: Optimization of Higher-energy Collisional Dissociation (HCD) Collision Energies for Tandem Mass Spectrometry Ions of a particular m/z-ratio coming from the first tandem mass spectrometer (MS1) were selected and then split into smaller fragment ions by higher-energy collisional dissociation (HCD). These fragments were then introduced into the second mass spectrometer (MS2), which in turn separated and detected the fragments according to m/z.

Figure 16:
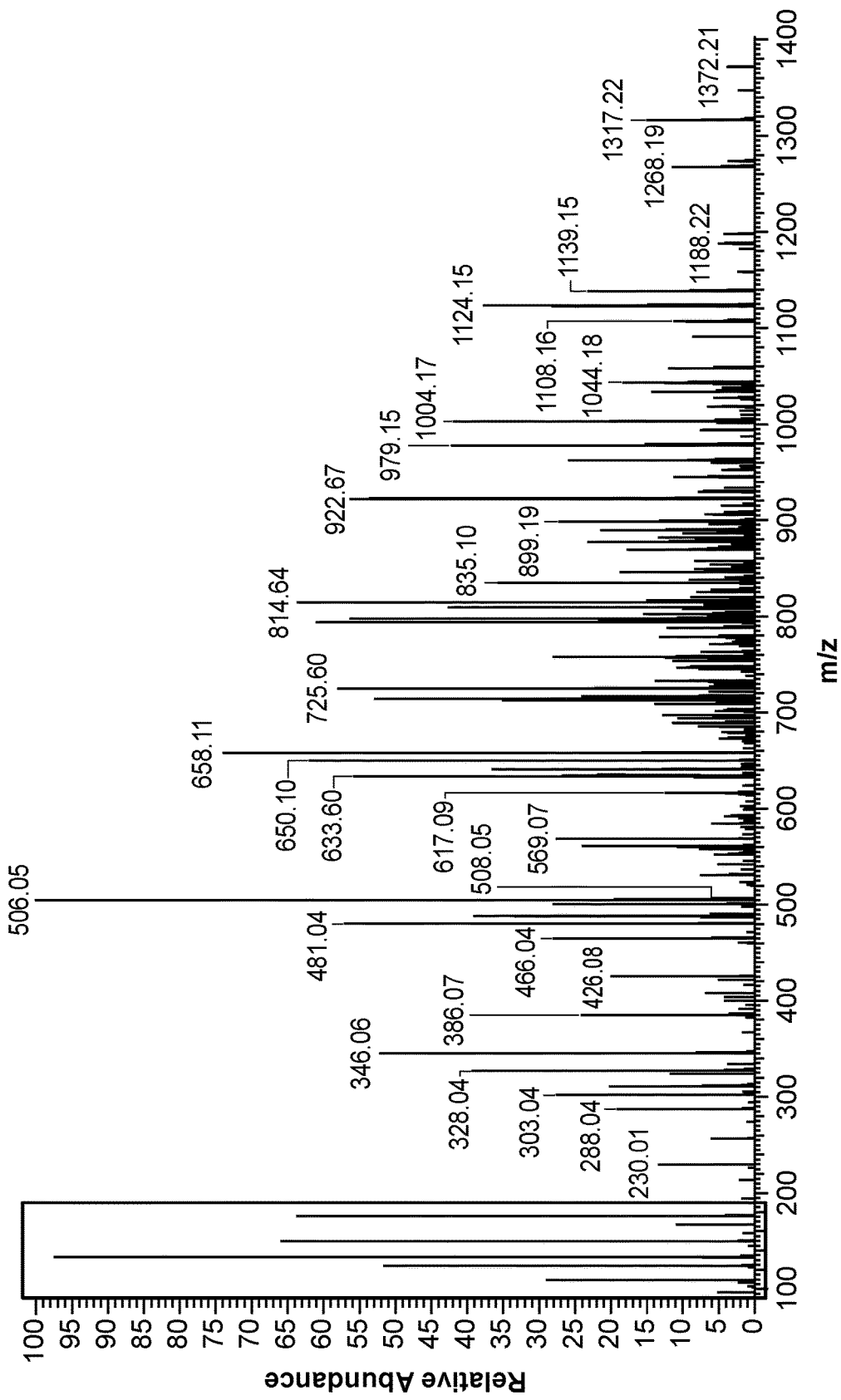
FIG. 16 is a pair of plots showing improved fragmentation efficiency is achieved by nano-flow IPRP-LC-MS/MS of oligo CMV-F.
Figure 16:
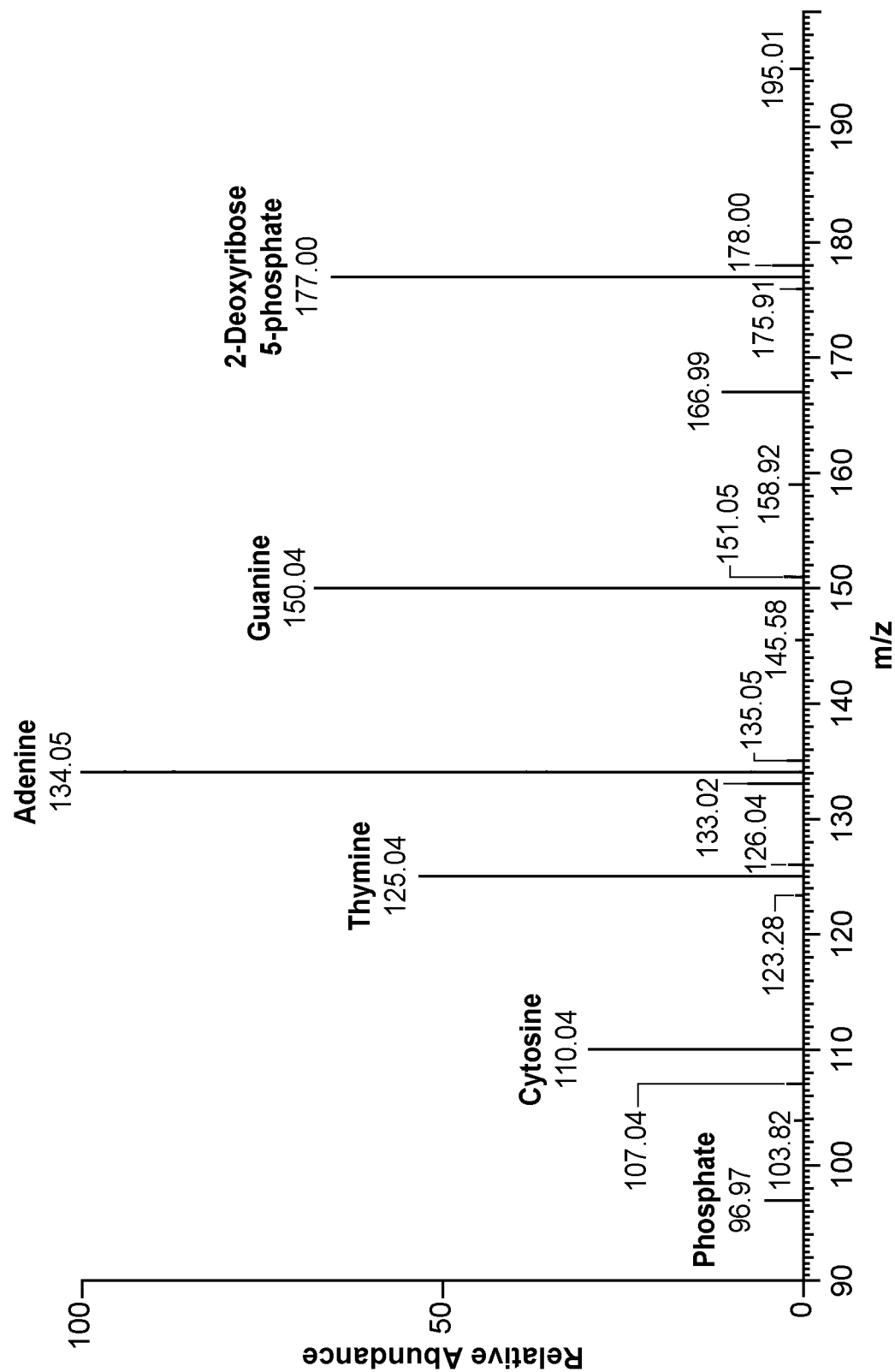
Figure 17:
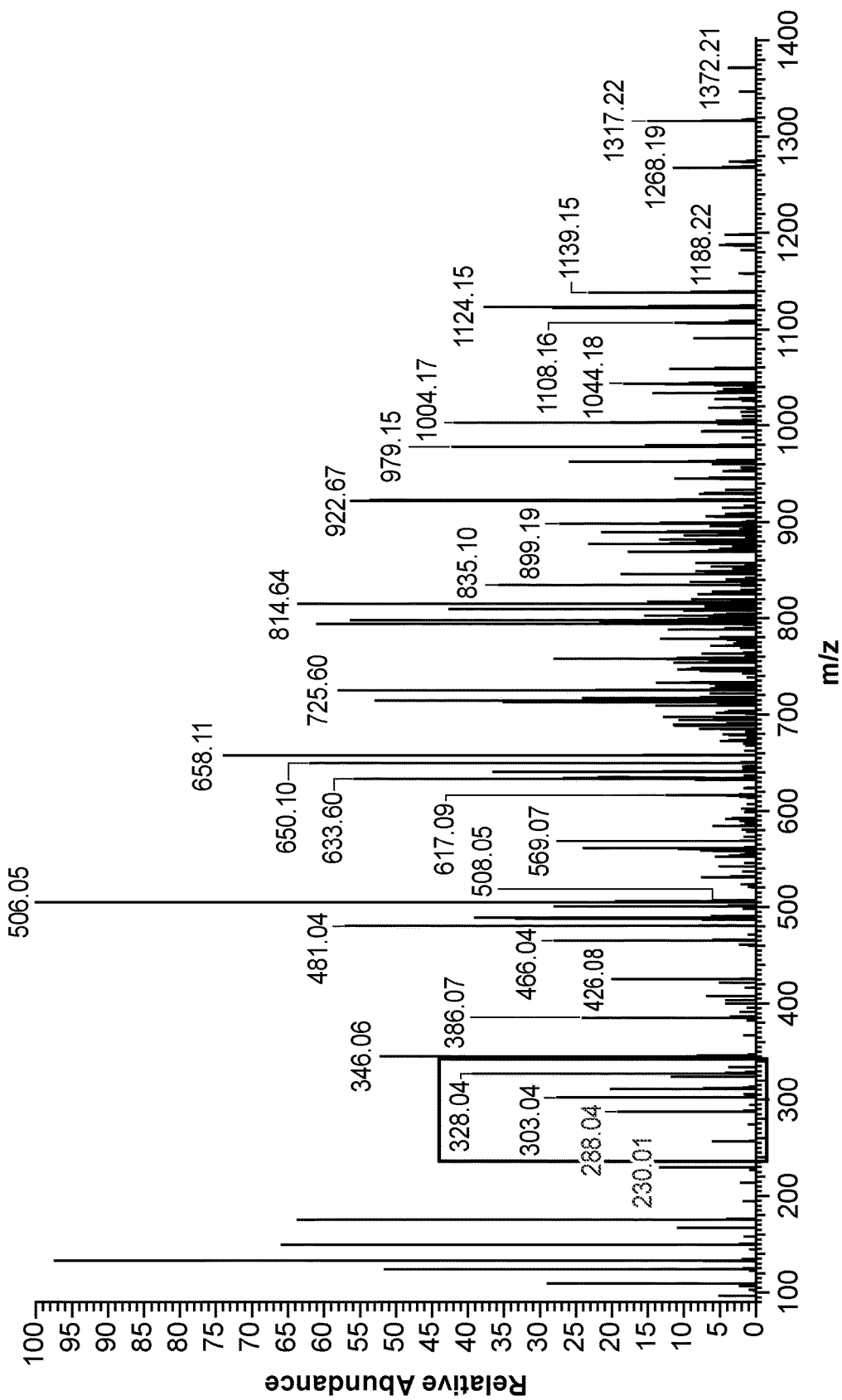
FIG. 17 is a pair of plots showing improved fragmentation efficiency is achieved by nano-flow IPRP-LC-MS/MS of oligo CMV-F.
Figure 17:
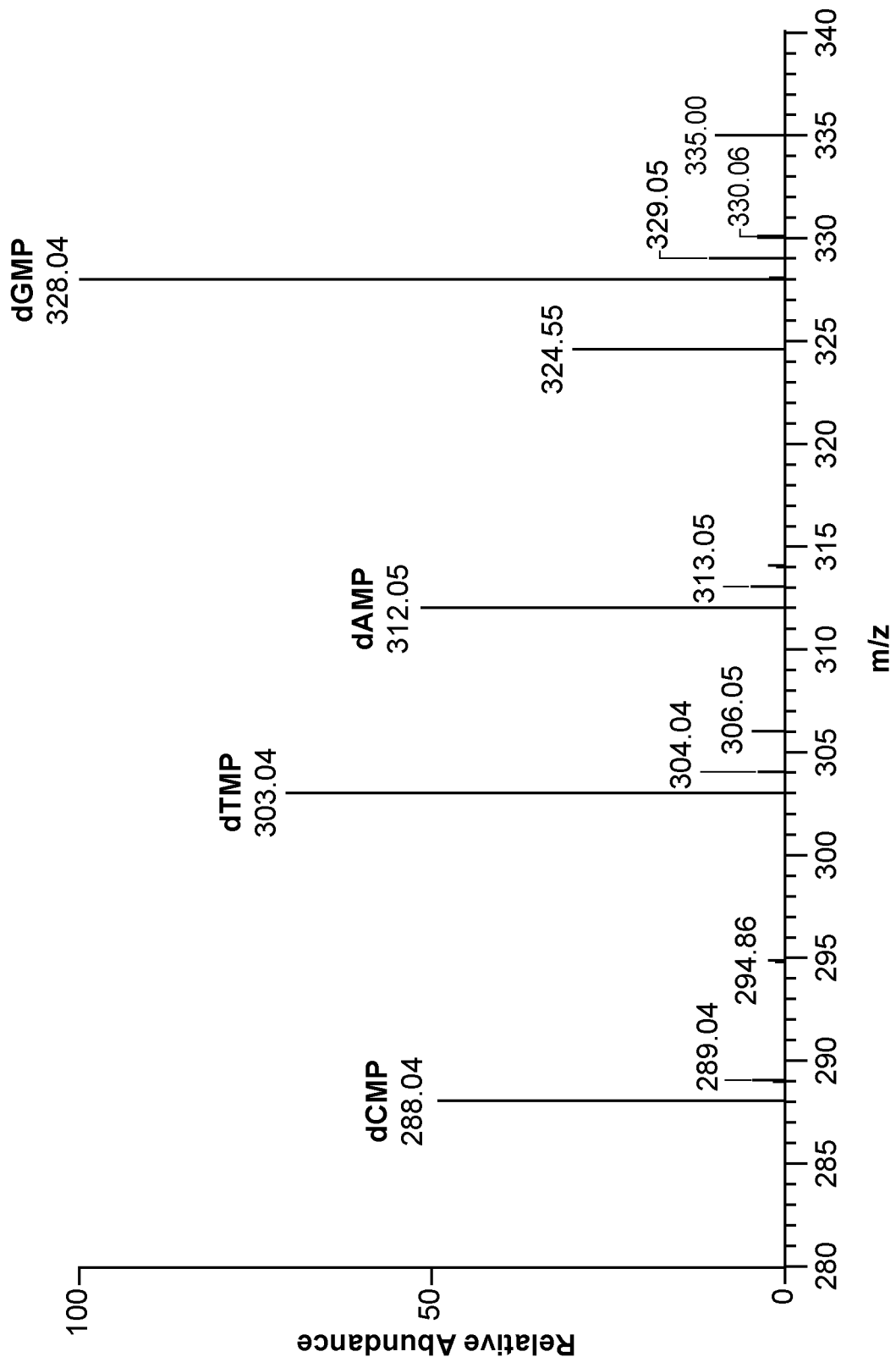

Oligonucleotides fragment along the phosphate backbone produce a set of ions containing the 5' terminus (a-B, b, and d) and another set of ions containing the 3' terminus (w and Nano-flow electrospray ionization (ESI) uses a flow splitter with lower flow rates. A flow was splitter was used to achieve nano-flow electrospray ionization to separate samples. FIGS. 16 and 17 show that fragmentation efficiency can be further improved by nano-flow IP-RPLC-MS/MS.

Example 6: Fragmentation of Phosphorothioate (PS) Modified Oligonucleotides

Figure 19A:
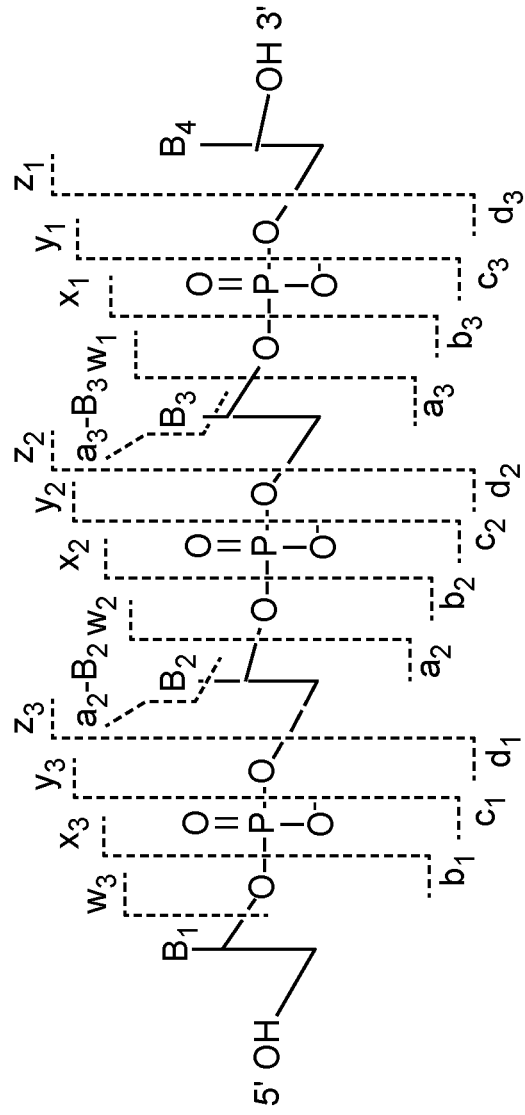
Figure 19B:
Figure 20:
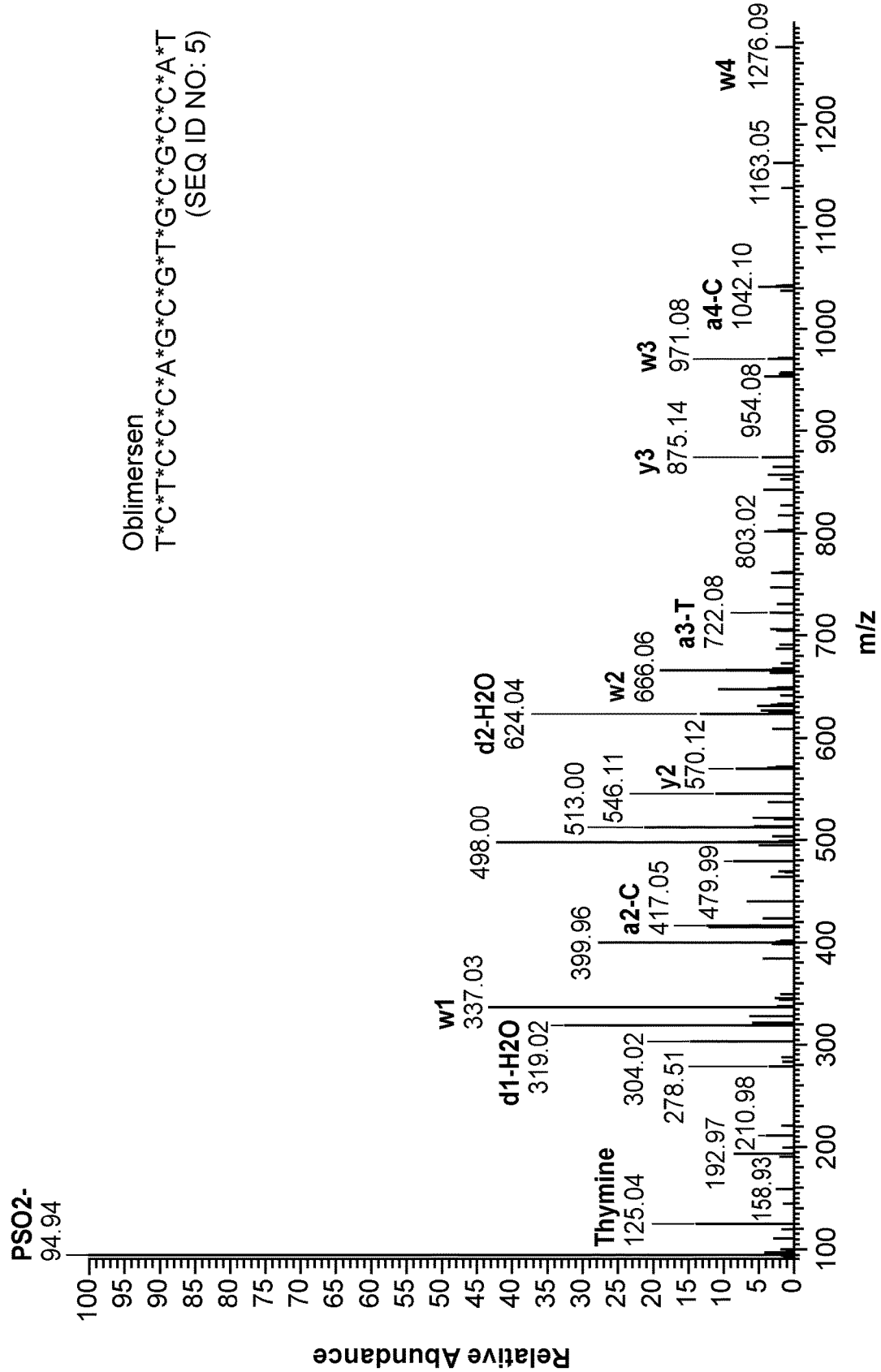
FIG. 20 is a plot showing fragmentation of the fragmentation of the [M−4H]$^{4-}$ (m/z 1419.8799) precursor of the PS-modified oligonucleotide Oblimersen with HCD at 20.

Tandem mass spectrometry (see Example 5) can be used to analyze modified oligonucleotides, as well as unmodified oligonucleotides. FIGS. 19A, 19B and 19C show the calculated masses of Oblimersen fragments. FIG. 20 shows an exemplary mass spectrum of fragmented Oblimersen $[M-4H]^{4-}$ ion precursor (m/z 1419.8799) generated with an HCD of 20%.

What is claimed is:

1. A method of making a composition comprising oligonucleotides of interest with high purity, the method comprising:
 a. synthesizing a population of oligonucleotides of interest, thereby providing a sample comprising the population of oligonucleotides of interest and at least one impurity comprising at least one additional population of oligonucleotides, wherein individual oligonucleotides of interest in the population have identical sequences;
 b. subjecting the sample to liquid chromatography and mass spectrometry, wherein the liquid chromatography comprises Ion-pairing Reversed-Phase Liquid Chromatography (IP-RPLC), and wherein the IP-RPLC comprises a mobile phase comprising a first buffer comprising 40-60 mM Hexafluoroisopropanol (HFIP) and 3-15 mM N,N-Diisopropylethylamine (DIEA) in water and a second buffer comprising 40-60 mM HFIP and 3-15 mM DIEA in acetonitrile, thereby generating at least one mass spectrogram corresponding to the population of oligonucleotides of interest and a mass spectrogram corresponding to the at least one additional population of oligonucleotides;
 c. determining a percentage of total oligonucleotides in the sample corresponding to the population of oligonucleotides of interest; and
 d. selecting a sample comprising a population of the oligonucleotides of interest with high purity for the composition,
 thereby making the composition comprising oligonucleotides of interest with high purity.

2. The method of claim 1, wherein the additional population of oligonucleotides comprises a fragmentation product of or a synthesis byproduct of the oligonucleotides of interest.

3. The method of claim 1, further comprising determining the percentage of total oligonucleotides in the sample corresponding to the at least one additional population of oligonucleotides.

4. The method of claim 1, wherein the oligonucleotides of interest are deoxyribonucleic acids (DNA), ribonucleic acids (RNA), or DNA-RNA hybrids.

5. The method of claim 1, wherein the oligonucleotides of interest are single stranded or double stranded.

6. The method of claim 1, wherein the oligonucleotides of interest comprise a hairpin or stem-loop structure.

7. The method of claim 1, wherein the oligonucleotides of interest are between 15 and 100 nucleotides in length.

8. The method of claim 1, wherein the oligonucleotides of interest are therapeutic oligonucleotides.

9. The method of claim 8, wherein the therapeutic oligonucleotides comprise antisense oligonucleotides (ASO), dsRNAs, siRNAs, aptamers or microRNAs.

10. The method of claim 1, wherein the oligonucleotides of interest comprise at least one modification.

11. The method of claim 10, wherein the at least one modification is at the 5' end, the 3' end, an internal nucleobase, or a combination thereof, of individual oligonucleotides of interest.

12. The method of claim 10, wherein the at least one modification comprises a locked nucleic acid (LNA), a phosphorothioate (PS) linkage, a terminal 5' or 3' phosphate (PO), a 5' methyl (5-Me) modification, a 2'-O-Methyl (2'-O-Me) modification, a 2'-O-methoxyethyl (2'-MOE) modification, a constrained ethyl (cET) nucleoside analog, a polyethylene glycol (PEG) or a combination thereof.

13. The method of claim 1, wherein the mobile phase comprises a first buffer comprising 50 mM HFIP and 5 mM DIEA in water and a second buffer comprising 50 mM HFIP and 5 mM DIEA in acetonitrile.

14. The method of claim 1, wherein the IP-RPLC comprises a column with a mean nominal particle size of 1.7 μm, a median particle pore size of 130 Å, a column length 100 mm and a 2.1 mm inner diameter.

15. The method of claim 1, wherein the mass spectrometry comprises electrospray ionization (ESI).

16. The method of claim 1, wherein the mass spectrometry is tandem mass spectrometry (MS/MS).

17. The method of claim 1, wherein the mass spectrometry is tandem mass spectrometry (MS/MS) and wherein the MS/MS comprises fragmentation of the population of oligonucleotides of interest, the at least one additional population of oligonucleotides, or a combination thereof.

18. The method of claim 17, wherein the fragmentation comprises higher-energy collisional dissociation (HCD) comprising a normalized collisional energy (NCE) of 15% to 35%.

19. The method of claim 1, wherein step (c) comprises determining the intact mass of the oligonucleotides of interest.

20. The method of claim 1, wherein step (c) further comprises determining the intact mass of the at least one additional population of oligonucleotides.

21. The method of claim 1, wherein step (c) comprises determining the structure of the oligonucleotides of interest using mass spectrometry.

22. The method of claim 1, wherein step (c) further comprises determining the structure of the at least one additional population of oligonucleotides.

23. The method of claim 1, wherein at least 90% of the total oligonucleotides in the composition are the oligonucleotide of interest.

24. The method of claim 1, further comprising step (e) adding a pharmaceutically acceptable carrier, diluent or excipient.

25. The method of claim 1, wherein step (d) further comprises discarding or further purifying the sample if the sample is not of high purity.

26. A method of making a composition comprising oligonucleotides of interest, wherein at least 90% of the oligonucleotides in the composition are the oligonucleotide of interest, the method comprising:
  a. synthesizing a population of oligonucleotides of interest, thereby providing a sample comprising the population of oligonucleotides of interest of identical sequence and/or modification, and at least one impurity comprising at least one additional population of oligonucleotides;
  b. subjecting the sample to liquid chromatography and tandem mass spectrometry (MS/MS),
  wherein the liquid chromatography comprises:
    i. hydrophilic interaction liquid chromatography (HILIC) comprising a mobile phase, wherein the mobile phase comprises a first buffer comprising 15 mM ammonium formate or ammonium acetate in 70% acetonitrile (ACN), and a second buffer comprising 15 mM ammonium formate or ammonium acetate in 30% ACN, or
    ii. Ion-pairing Reversed-Phase Liquid Chromatography (IP-RPLC) comprising a mobile phase, wherein the mobile phase comprises a first buffer comprising 50 mM Hexafluoroisopropanol (HFIP) and 5 mM N,N-Diisopropylethylamine (DIEA) in water and a second buffer comprising 50 mM HFIP and 5 mM DIEA in acetonitrile;
  wherein the MS/MS comprises fragmentation of the population of oligonucleotides of interest and the additional population of oligonucleotides in the sample using higher-energy collisional dissociation (HCD) comprising a normalized collisional energy (NCE) of 15% to 35%,
  thereby generating at least one mass spectrogram corresponding to the population oligonucleotides of interest and a mass spectrogram corresponding to the additional population of oligonucleotides;
  c. determining a percentage of total oligonucleotides in the sample corresponding to the population of oligonucleotides of interest; and
  d. selecting a sample comprising a population of the oligonucleotides of interest, wherein at least 90% of the oligonucleotides in the composition are the oligonucleotide of interest, for the composition,
  thereby making the composition comprising oligonucleotides of interest.

27. The method of claim 26, further comprising step (e) adding a pharmaceutically acceptable carrier, diluent or excipient.

28. The method of claim 26, wherein step (d) further comprises discarding or further purifying the sample if less than 90% of the oligonucleotides in the composition are the oligonucleotide of interest.

* * * * *

UNITED STATES PATENT AND TRADEMARK OFFICE
CERTIFICATE OF CORRECTION

| | | |
|---|---|---|
| PATENT NO. | : 12,099,042 B2 | Page 1 of 1 |
| APPLICATION NO. | : 17/161803 | |
| DATED | : September 24, 2024 | |
| INVENTOR(S) | : Huang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 905 days.

Signed and Sealed this
Eighteenth Day of March, 2025

Coke Morgan Stewart
*Acting Director of the United States Patent and Trademark Office*

SEQUENCE LISTING

```
<160> NUMBER OF SEQ ID NOS: 18

<210> SEQ ID NO 1
<211> LENGTH: 17
<212> TYPE: DNA
<213> ORGANISM: Artificial Sequence
<220> FEATURE:
<223> OTHER INFORMATION: M13 Reverse oligo

<400> SEQUENCE: 1
caggaaacag ctatgac                                                    17

<210> SEQ ID NO 2
<211> LENGTH: 25
<212> TYPE: DNA
<213> ORGANISM: Artificial Sequence
<220> FEATURE:
<223> OTHER INFORMATION: TRC-F oligo

<400> SEQUENCE: 2
caaggctgtt agagagataa ttgga                                           25

<210> SEQ ID NO 3
<211> LENGTH: 20
<212> TYPE: DNA
<213> ORGANISM: Artificial Sequence
<220> FEATURE:
<223> OTHER INFORMATION: T7 Oligo

<400> SEQUENCE: 3
taatacgact cactataggg                                                 20

<210> SEQ ID NO 4
<211> LENGTH: 18
<212> TYPE: DNA
<213> ORGANISM: Artificial Sequence
<220> FEATURE:
<223> OTHER INFORMATION: unmodified Oblimersen

<400> SEQUENCE: 4
tctcccagcg tgcgccat                                                   18

<210> SEQ ID NO 5
<211> LENGTH: 18
<212> TYPE: DNA
<213> ORGANISM: Artificial Sequence
<220> FEATURE:
<223> OTHER INFORMATION: oblimersen oligo with modifications
<220> FEATURE:
<221> NAME/KEY: phosphorothioate
<222> LOCATION: (2)..(18)
<223> OTHER INFORMATION: * indicates a phosphorothioate linkage

<400> SEQUENCE: 5
tctcccagcg tgcgccat                                                   18

<210> SEQ ID NO 6
<211> LENGTH: 18
<212> TYPE: DNA
<213> ORGANISM: Artificial Sequence
<220> FEATURE:
<223> OTHER INFORMATION: SP6 oligo

<400> SEQUENCE: 6
atttaggtga cactatag                                                   18
```

```
<210> SEQ ID NO 7
<211> LENGTH: 21
<212> TYPE: DNA
<213> ORGANISM: Artificial Sequence
<220> FEATURE:
<223> OTHER INFORMATION: T3 oligo

<400> SEQUENCE: 7
gcaattaacc ctcactaaag g                                      21

<210> SEQ ID NO 8
<211> LENGTH: 21
<212> TYPE: DNA
<213> ORGANISM: Artificial Sequence
<220> FEATURE:
<223> OTHER INFORMATION: CMV forward primer

<400> SEQUENCE: 8
cgcaaatggg cggtaggcgt g                                      21

<210> SEQ ID NO 9
<211> LENGTH: 21
<212> TYPE: DNA
<213> ORGANISM: Artificial Sequence
<220> FEATURE:
<223> OTHER INFORMATION: Formivirsen oligo
<220> FEATURE:
<221> NAME/KEY: phosphorothioate
<222> LOCATION: (2)..(21)
<223> OTHER INFORMATION: * indicates phosphorothioate linkage

<400> SEQUENCE: 9
gcgtttgctc ttcttcttgc g                                      21

<210> SEQ ID NO 10
<211> LENGTH: 15
<212> TYPE: DNA
<213> ORGANISM: Artificial sequence
<220> FEATURE:
<223> OTHER INFORMATION: polyT nucleotide

<400> SEQUENCE: 10 ttttttttttt ttttt                                            15

<210> SEQ ID NO 11
<211> LENGTH: 20
<212> TYPE: DNA
<213> ORGANISM: Artificial Sequence
<220> FEATURE:
<223> OTHER INFORMATION: poly(T) oligo

<400> SEQUENCE: 11
tttttttttt tttttttttt                                        20

<210> SEQ ID NO 12
<211> LENGTH: 25
<212> TYPE: DNA
<213> ORGANISM: Artificial Sequence
<220> FEATURE:
<223> OTHER INFORMATION: poly(T) oligo

<400> SEQUENCE: 12
tttttttttt tttttttttt ttttt                                  25

<210> SEQ ID NO 13
<211> LENGTH: 30
<212> TYPE: DNA
```

-continued

```
<213> ORGANISM: Artificial Sequence
<220> FEATURE:
<223> OTHER INFORMATION: poly(T) oligo

<400> SEQUENCE: 13
tttttttttt tttttttttt tttttttttt                                    30

<210> SEQ ID NO 14
<211> LENGTH: 35
<212> TYPE: DNA
<213> ORGANISM: Artificial Sequence
<220> FEATURE:
<223> OTHER INFORMATION: poly(T) oligo

<400> SEQUENCE: 14
tttttttttt tttttttttt tttttttttt ttttt                              35

<210> SEQ ID NO 15
<211> LENGTH: 18
<212> TYPE: DNA
<213> ORGANISM: Artificial Sequence
<220> FEATURE:
<223> OTHER INFORMATION: Nusinersen oligo
<220> FEATURE:
<221> NAME/KEY: MOEr
<222> LOCATION: (1)..(18)
<223> OTHER INFORMATION: 2'-O-methoxy-ethyl (MOEr) modification
<220> FEATURE:
<221> NAME/KEY: 5me
<222> LOCATION: (2)..(2)
<223> OTHER INFORMATION: 5-methyl modification
<220> FEATURE:
<221> NAME/KEY: *
<222> LOCATION: (2)..(18)
<223> OTHER INFORMATION: * indicates phosphorothioate linkage
<220> FEATURE:
<221> NAME/KEY: 5me
<222> LOCATION: (4)..(4)
<223> OTHER INFORMATION: 5-methyl modification
<220> FEATURE:
<221> NAME/KEY: 5me
<222> LOCATION: (8)..(8)
<223> OTHER INFORMATION: 5-methyl modification
<220> FEATURE:
<221> NAME/KEY: 5me
<222> LOCATION: (15)..(15)
<223> OTHER INFORMATION: 5-methyl modification

<400> SEQUENCE: 15
tcactttcat aatgctgg                                                 18

<210> SEQ ID NO 16
<211> LENGTH: 20
<212> TYPE: DNA
<213> ORGANISM: Artificial Sequence
<220> FEATURE:
<223> OTHER INFORMATION: Inotersen
<220> FEATURE:
<221> NAME/KEY: MOEr
<222> LOCATION: (1)..(5)
<223> OTHER INFORMATION: 2'-O-methoxy-ethyl (MOEr) modification
<220> FEATURE:
<221> NAME/KEY: *
<222> LOCATION: (2)..(20)
<223> OTHER INFORMATION: * indicates phosphorothioate linkage
<220> FEATURE:
<221> NAME/KEY: 5me
<222> LOCATION: (2)..(2)
<223> OTHER INFORMATION: 5-methyl modification
<220> FEATURE:
<221> NAME/KEY: 5me
<222> LOCATION: (10)..(10)
<223> OTHER INFORMATION: 5-methyl modification
```

```
<220> FEATURE:
<221> NAME/KEY: MOEr
<222> LOCATION: (16)..(20)
<223> OTHER INFORMATION: 2'-O-methoxy-ethyl (MOEr) modification
<220> FEATURE:
<221> NAME/KEY: 5me
<222> LOCATION: (18)..(20)
<223> OTHER INFORMATION: 5-methyl modification

<400> SEQUENCE: 16
tcttggttac atgaaatccc                                                    20

<210> SEQ ID NO 17
<211> LENGTH: 20
<212> TYPE: DNA
<213> ORGANISM: Artificial Sequence
<220> FEATURE:
<223> OTHER INFORMATION: Mipomersen
<220> FEATURE:
<221> NAME/KEY: MOEr
<222> LOCATION: (1)..(5)
<223> OTHER INFORMATION: 2'-O-methoxy-ethyl (MOEr) modification
<220> FEATURE:
<221> NAME/KEY: 5me
<222> LOCATION: (2)..(3)
<223> OTHER INFORMATION: 5-methyl modification
<220> FEATURE:
<221> NAME/KEY: *
<222> LOCATION: (2)..(20)
<223> OTHER INFORMATION: * indicates phosphorothioate linkage
<220> FEATURE:
<221> NAME/KEY: 5me
<222> LOCATION: (5)..(5)
<223> OTHER INFORMATION: 5-methyl modification
<220> FEATURE:
<221> NAME/KEY: 5me
<222> LOCATION: (9)..(9)
<223> OTHER INFORMATION: 5-methyl modification
<220> FEATURE:
<221> NAME/KEY: 5me
<222> LOCATION: (12)..(12)
<223> OTHER INFORMATION: 5-methyl modification
<220> FEATURE:
<221> NAME/KEY: 5me
<222> LOCATION: (15)..(15)
<223> OTHER INFORMATION: 5-methyl modification
<220> FEATURE:
<221> NAME/KEY: MOEr
<222> LOCATION: (16)..(20)
<223> OTHER INFORMATION: 2'-O-methoxy-ethyl (MOEr) modification
<220> FEATURE:
<221> NAME/KEY: 5me
<222> LOCATION: (17)..(17)
<223> OTHER INFORMATION: 5-methyl modification
<220> FEATURE:
<221> NAME/KEY: 5me
<222> LOCATION: (19)..(20)
<223> OTHER INFORMATION: 5-methyl modification

<400> SEQUENCE: 17
gcctcagtct gcttcgcacc                                                    20

<210> SEQ ID NO 18
<211> LENGTH: 16
<212> TYPE: DNA
<213> ORGANISM: Artificial Sequence
<220> FEATURE:
<223> OTHER INFORMATION: AZD4785
<220> FEATURE:
<221> NAME/KEY: cET
<222> LOCATION: (1)..(3)
<223> OTHER INFORMATION: constrained ethyl nucleoside analog
<220> FEATURE:
<221> NAME/KEY: *
<222> LOCATION: (2)..(16)
```

```
<223> OTHER INFORMATION: * indicates phosphorothioate linkage
<220> FEATURE:
<221> NAME/KEY: cET
<222> LOCATION: (14)..(16)
<223> OTHER INFORMATION: constrained ethyl nucleoside analog

<400> SEQUENCE: 18
gctattagga gtcttt                                                            16
```